(12) United States Patent
Yuan

(10) Patent No.: US 6,610,504 B1
(45) Date of Patent: Aug. 26, 2003

(54) METHODS OF DETERMINING SAM-DEPENDENT METHYLTRANSFERASE ACTIVITY USING A MUTANT SAH HYDROLASE

(75) Inventor: Chong-Sheng Yuan, San Diego, CA (US)

(73) Assignee: General Atomics, San Diego, CA (US)

( * ) Notice: Subject to any disclaimer, the term of this patent is extended or adjusted under 35 U.S.C. 154(b) by 0 days.

(21) Appl. No.: 09/546,013

(22) Filed: Apr. 10, 2000

(51) Int. Cl.⁷ .............................. C12Q 1/48; C12Q 1/34
(52) U.S. Cl. ............................................. 435/15; 435/18
(58) Field of Search ..................................... 435/15, 18

(56) References Cited

U.S. PATENT DOCUMENTS

| | | | |
|---|---|---|---|
| 3,464,890 A | 9/1969 | Weichselbaum | 195/66 |
| 3,647,070 A | 3/1972 | Adler | 210/83 |
| 3,780,935 A | 12/1973 | Lucacs | 233/1 A |
| 3,843,443 A | 10/1974 | Fishman | 195/63 |
| 3,852,194 A | 12/1974 | Zine et al. | 210/83 |
| 3,939,123 A | 2/1976 | Matthews et al. | 260/77.5 |
| 4,140,631 A | 2/1979 | Okuda et al. | 210/83 |
| 4,162,355 A | 7/1979 | Tsibris | 526/293 |
| 4,171,412 A | 10/1979 | Coupek | 525/329 |
| 4,175,183 A | 11/1979 | Ayers | 536/57 |
| 4,177,038 A | 12/1979 | Biebricher et al. | 8/192 |
| 4,178,439 A | 12/1979 | Ayers et al. | 536/59 |
| 4,179,402 A | 12/1979 | Kim et al. | 252/431 |
| 4,180,524 A | 12/1979 | Reusser et al. | 585/644 |
| 4,241,537 A | 12/1980 | Wood | 47/77 |
| 4,244,721 A | 1/1981 | Gupta et al. | 65/31 |
| 4,282,287 A | 8/1981 | Giese | 428/407 |
| 4,439,585 A | 3/1984 | Gould et al. | 525/127 |
| 4,477,575 A | 10/1984 | Vogel et al. | 436/170 |
| 4,485,227 A | 11/1984 | Fox | 528/61 |
| 4,542,102 A | 9/1985 | Dattagupta et al. | 435/6 |
| 4,562,157 A | 12/1985 | Lowe et al. | 435/291 |
| 4,569,789 A | 2/1986 | Blattler et al. | 260/112 R |
| 4,569,981 A | 2/1986 | Wenzel et al. | 528/67 |
| 4,681,870 A | 7/1987 | Balint, Jr. et al. | 502/403 |
| 4,762,881 A | 8/1988 | Kauer | 525/54.11 |
| 4,795,699 A | 1/1989 | Tabor et al. | 435/5 |
| 4,803,153 A | 2/1989 | Shibata et al. | 435/2 |
| 4,885,250 A | 12/1989 | Eveleigh et al. | 435/181 |
| 4,894,443 A | 1/1990 | Greenfield et al. | 530/388 |
| 4,908,405 A | 3/1990 | Bayer et al. | 525/61 |
| 4,952,394 A | 8/1990 | Senter | 424/85.91 |
| 4,954,444 A | 9/1990 | Eveleigh et al. | 435/181 |
| 5,137,877 A | 8/1992 | Kaneko et al. | 514/25 |
| 5,292,814 A | 3/1994 | Bayer et al. | 525/243 |
| 5,328,603 A | 7/1994 | Velander et al. | 210/198.2 |
| 5,334,640 A | 8/1994 | Desai et al. | 524/56 |
| 5,349,066 A | 9/1994 | Kaneko et al. | 546/294 |
| 5,364,533 A | 11/1994 | Ogura et al. | 210/645 |
| 5,416,193 A | 5/1995 | Desai | 530/334 |
| 5,451,683 A | 9/1995 | Barrett et al. | 548/302.7 |
| 5,612,474 A | 3/1997 | Patel | 536/27.14 |
| 5,618,528 A | 4/1997 | Cooper et al. | 424/78.3 |
| 5,679,548 A | 10/1997 | Barbas et al. | 435/69.6 |
| 5,834,184 A | 11/1998 | Harada et al. | 435/6 |
| 5,858,675 A | 1/1999 | Hillman et al. | 435/6 |
| 5,859,227 A | 1/1999 | Giordano et al. | 536/24.1 |

FOREIGN PATENT DOCUMENTS

| | | |
|---|---|---|
| DE | 197 57 571 | 6/1999 |
| WO | WO/86 03840 | 7/1986 |
| WO | WO 88/08137 | 10/1988 |
| WO | WO 93/15220 | 8/1993 |
| WO | WO 98/20156 | 5/1998 |

OTHER PUBLICATIONS

Williams et al. (1998) Biochemistry 37:7096–7102.*
Adams and Blumenthal. (1997). *Biochemistry* 36(27): 8284–8292.
Bastin et al. (1996). *Mol Biochem Parasitology* 77:235–239.
Batra, et al. (1993). *Mol Immunol* 30:379–386.
Bendixen, et al. (1994). *Nucl Acids Res* 22:1778–1779.
Benoist and Chambon (1981). *Nature* 290:304–310.
Bokar et al. (1994). *J Biol Chem* 269:17697–17704.
Braunwalder, et al. (1996). *J. Biomol Screening* 1:23–26.
Broach, et al. (1996). *Nature* 384:14–16.
Brown, et al. (1997) *Curr Opin Biotechnol* 8:45–49.
Buchko, et al (1999). *Biochim Biophys Res Commun* 254(1):109–113.
Burbaum, et al. (1997). *Curr Opin Chem Biol* 1:72–78.
Burd and Dreyfuss. (1994). *EMBO J* 13:1197.
Burd and Deyfuss (1994). *Science* 265:615–621.
Casellas and Jeanteur. (1978). *Biochim Biophys Acta* 519(1):243–268.
Chen and Katz (1998). *Bio Techniques* 25(1):22–24.
Cordingley, et al. (1990). *J Biol Chem* 265:9062.
Cwirla, et al. (1990). *Proc Natl Acad Sci USA* 87:6378–6382.
DeWitt, et al. (1993). *Proc Natl Acad Sci USA* 90:6909.
Edwards and Dixon. (1991). *Arch Biochem Biophys* 287(2):372–379.
Fattom, et al. (1992). *Infection & Immun* 60:584–589.
Feng, et al. (1998). *Cur Biol* 8:267–278.
Fernandes (1997). *J Biomol Screening* 2:1.
Geelen, et al. (1995). *Mol Microbiol* 17(2):387–397.
Germino, et al. (1984). *Proc Natl Acad Sci USA* 81:4692.
Geysen, et al. (1984). *Proc Natl Acad Sci USA* 81:3998–4002.
Gloria, et al. (1996). *Cancer,* 78:2300–2306.
Goldmacher, et al. (1992). *Bioconj. Chem* 3:104–107.

(List continued on next page.)

*Primary Examiner*—Rebecca E. Prouty
*Assistant Examiner*—David J. Steadman
(74) *Attorney, Agent, or Firm*—Morrison & Foerster LLP

(57) ABSTRACT

The present invention relates to compositions and methods for assaying the activity of methyltransferases, such as S-adenosylmethionine (SAM)-dependent methyltransferases. The methods can be used for screening for modulators of such methyltransferases, for identifying substrates and for diagnostics. The methods are amenable for use in high throughput formats. Kits for performing the methods are also provided.

17 Claims, No Drawings

OTHER PUBLICATIONS

Gonzalez, et al. (1995). *Biophys J* 69:1272–1280.
Gosnami, et al. (1982). *J Biol Chem* 257:6867–6870.
Grunstein and Hogness. (1975). *Proc Natl Acad Sci USA* 72:3961–3965.
Habig, et al (1974). *J Biol Chem* 249:7130.
Hadd, et al. (1997). *Anal Chem* 69:3407–3412.
Higman and Niles. (1994). *J Biol Chem* 269(21):14982–14987.
Hinderliter, et al. (1998). *Biochim Biophys Acta* 1448(2):227–235.
Houghten, et al. (1985). *Proc Natl Acad Sci USA* 81:5131–5135.
Hutchinson, et al. (1978). *J Biol Chem* 253:6551.
Itoh, et al. (1997). *J Chromatogr B Biomed Sci Appl* 692(1):217–221.
Janssen and Nes. (1992). *J Biol Chem* 267(36):25856–25863.
St.Johnston, et al. (1992). *Proc Natl Acad Sci USA* 89:10979–10983.
Kagan R. and Clarke S. (1994). *Archives of Biochem & Biophys* 310:417–427.
Kane, et al. (1996). *Anal Biochem* 233(2):197–204.
Kang, et al. (1997). *Virus Res* 49(2):147–154.
Klein, et al. (1997). *J Biomol Screening* 2:41–49.
Kolodziej and Young (1991). *Methods Enzymol* 194:508–519.
Kozak (1991). *J Biol Chem* 266:19867–19870.
Kramer et al. (1990). *Cancer Res* 50:3838–3842.
Kuo, et al. (1981). *J Immunol Methods* 43(1):35–47.
Lam, et al. (1991). *Nature* 354:82–84.
Lester, et al. (1996). *J Biol Chem* 271:9460–9465.
Lieberman, et al. (1994). *Genes & Dev* 8:995–1006.
Lowenadler, et al. (1987). *Gene* 58:87.
Lucas, et al. (1998). *J Immunol* 161(7):3776–3780.
Lue, et al. (1987). *Proc Natl Acad Sci USA* 84:8839–8843.
Lynch, et al. (1997). *Anal Biochem* 247:77–82.
Maeji, et al. (1992). *J Immunol Met* 146:83–90.
Maru, et al. (1996). *J Biol Chem* 271:15353.
Mathis (1995). *Clin Chem* 41:1391–1397.
Maxam and Gilbert (1980). *Meth Enzymol* 65:499–560.
McTigue, et al. (1995). *J Mol Biol* 246:21.
Merrifield. (1964). *Biochemistry* 3:1385–1390.
Minarovits et al. (1994). Virology 200:661–667.x.
Mozier, et al. (1988). *J Biol Chem* 263 (10):4527–4531.
Murre, et al. (1989). *Cell* 56:777–783.
Nagai and Thogersen (1987). Methods Enzymol 153:461.
Nagelkerken et al (1997). *Electrophoresis* 18:2684–2698.
Nielsen, et al. (1983). *Proc Natl Acad Sci USA* 80:5198.
Nilsson, et al. (1985). *EMBO J* 4:1075.
Nosaka, et al. (2000). *Cancer Res* 60:1043–1048.
Olah et al. (1994). Anal *Biochem* 221:94–102.
Pakusch, et al (1989). *Arch Biochem Biophys* 271(2):488–494.
Posfai, et al. (1989). *Nucleic Acids Res* 17:2421–2435.
Post, et al. (1999). *Cardiovasc Res* 43:985–991.
Powers, et al. (1989). Biotechnol Bioeng 33:173.
Prickett et al. (1989). *Bio Techniques* 7(6):580–584.
Pu, et al. (1992). *Nucl Acids Res* 20:771–775.
Rogers (1997). *Drug Discov Today* 2:306.
Ross, et al. (1999). *Arch Biochem Biophys* 367(1):9–16.
Rudiger et al. (1997). *Bio Techniques* 23 (1):96–97.
Schroeder, et al. (1996). *J Biomol Screening* 1:75–80.
Schullek, et al. (1997). *Anal Biochem* 246:20–29.
SenGupta et al. (1996). *Proc Natl Acad Sci, USA* 93:8496–8501.
Senter, et al. (1985). *Photochem Photobiol* 42:231–237.
Shapira, et al. (1983). *Gene* 25:71.
Shilo and Weinberg (1981). *Proc Natl Acad Sci USA* 78:6789–6792.
Silverman, et al. (1998). *Curr Opin Chem Biol* 2(3):397–403.
Sittampalam, et al. (1997). *Curr Opin Chem Biol* 1(3):384–391.
Smith and Johnson (1988). *Gene* 7:31–40.
Sterrer, et al. (1997). *J Recept Signal Transduct Res* 17:511–520.
Strauss, et al. (1981). *Gene* 13:75–87.
Syed, et al. (1993). *Biochemistry* 32(9):2242–2247.
Takata and Fujioka. (1992). *Bichemistry* 31(17):4369–4374.
Taylor, et al. (1985). *Nucleic Acids Res* 13:8765–8785.
Tolbert and Lameh. (1998). *J Neurochem* 70:113–119.
Toye, et al. (1990). *Infect Immunity* 58:3909.
Tseng and Verma. (1996). *Gene* 169:287–288.
Tullius, et al. (1987). Meth Enzymol 155:537–558.
Turker and Bestor. (1997). *Mutat Res.* 386:119–130.
Turner, et al. (1998). *Nature Structural Biol* 5:369–376.
Vilbois, et al. (1994). *Eur J Biochem* 222(2):377–386.
Waggoner, et al. (1996). *Hum Pathol* 27:494–502.
Wang, et al. (1990). *Tetrahedron Lett* 31:6493–6496.
Wang et al. (1996). *Gene* 169(1):53–58.
Wang, et al. (1996). *Genes & Dev* 10:3028–3040.
Watson, et al. (1996). *BioTechniques* 21(2): 255–259.
Wellhoner, et al (1991). *J Biol Chem* 266:4309–4314.
Willis, et al. (1989). *Cell Biophys* 15:97–111.
Wu, et al. (1992). *J Gen Microbiol*138:2101–2112.
Xie et al. (1998). *Endocrinology* 139(11):4563–4567.
Yamaguchi, et al. (1998). *Oral Microbiol. Immunol* 13(6):348–354.
Yamamoto, et al. (1980). *Cell* 22:787–797.
Yen, et al. (1989). *Makromol Chem* 190:69–82.
You, et al. (1997). *Chem Biol* 4:969–975.
Yuan, et al (1993). *J Biol Chem* 268:17030–17037.
Yuan, et al (1996). *J Biol Chem* 271:28009–28016.
Zapp et al. (1989). *Nature* 342:714.

\* cited by examiner

METHODS OF DETERMINING SAM-DEPENDENT METHYLTRANSFERASE ACTIVITY USING A MUTANT SAH HYDROLASE

RELATED APPLICATIONS

This application is related to U.S. application Ser. No. 09/347,878 to Chong-Shen Yuan, filed Jul. 6, 1999, now U.S. Pat. No. 6,376,210 entitled "COMPOSITIONS AND METHODS FOR ASSAYING ANALYTES" and U.S. application Ser. No. 09/457,205 to Chong-Shen Yuan, filed Dec. 6, 1999, entitled "COMPOSITIONS AND METHODS FOR ASSAYING ANALYTES." U.S. application Ser. No. 09/457,205 is a continuation-in-part application of U.S. patent application Ser. No. 09/347,878, filed Jul. 6, 1999, now U.S. Pat. No. 6,376,210. The contents of each of these applications is incorporated herein in its entirety.

FIELD OF THE INVENTION

Compositions and methods for assaying the activity of S-adenosylmethionine (SAM)-dependent methyltransferases and for screening for modulators of the activity SAM-dependent methyltransferases are provided. Kits and articles of manufacture that contain the modified enzymes and that can be used in these methods are also provided herein.

BACKGROUND OF THE INVENTION

Of the 3,196 enzymes described in the latest version of Enzyme Nomenclature (Webb, *Enzyme Nomenclature*, Academic Press, San Diego (1992)), about 3% represent species that catalyze the attack of a variety of nitrogen, oxygen, carbon, and sulfur nucleophiles on the methyl group of S-adenosylmethionine (Kagan and Clarke, *Arch. Biochem. Biophys.*, 310(2):417–427 (1994)). These methyltransferases include enzymes that result in the formation of methyl esters, methyl ethers, methyl thioethers, methyl amines, methyl amides and other derivatives on proteins, nucleic acids, polysaccharides, lipids and various small molecules. Among these methyltransferases are S-adenosylmethionine (SAM)-dependent methyltransferases.

Methyltransferase, including SAM-dependent methyltransferase, catalyzed abnormal methylation has been linked to pathological conditions (see, e.g., U.S. Pat. No. 5,876,996). For example, covalent modification of cellular substrates with methyl groups has been implicated in the pathology of cancer and other diseases (Gloria, et al., *Cancer*, 78:2300–2306 (1996)). Cytosine hypermethylation of eukaryotic DNA prevents transcriptional activation (Turker and Bestor, *Mutat. Res.*, 386:119–130 (1997)). $N^6$-methyladenosine is found at internal positions of mRNA in higher eukaryotes (Bokar, et al., *J. Biol. Chem.*, 269:17697–17704 (1994)). Hypermethylated viral DNA is transcribed at higher rates than hypo- or hemimethylated DNA in infected cells (Willis, et al. *Cell. Biophys.*, 15:97–111 (1989)).

In addition, many pathways of small molecule degradation, such as those of neurotransmitters, require methyltransferase activity (U.S. Pat. No. 5,876,996; and Kagan and Clarke, *Arch. Biochem. Biophys.*, 310:417–427 (1994)). Degradation of catecholamines (epinephrine ornorepinephrine) requires phenylethanolamine N-methyltransferase. Hydroxyindole methyltransferase converts N-acetyl-5-hydroxytryptarnine to melatonin in the pineal gland.

In their roles as a rate-limiting step in methyltransferase reactions, SAM-dependent methyltransferases have been identified as targets for psychiatric, antiviral, anticancer and anti-inflammatory drug design (U.S. Pat. No. 5,876,996). For instances, sequence-specific methylation inhibits the activity of the Epstein-Barr virus LMP 1 and BCR2 enhancer-promoter regions (Minarovits et al., *Virology*, 200:661–667 (1994)). 2'-5'-linked oligo(adenylic acid) nucleoside analogues synthesized by interferon-treated mouse L cells act as antiviral agents (Goswarmi, et al., *J. Biol. Chem.*, 257:6867–6870 (1982)). Adenine analog inhibitors of AdoMet-MT decreased nucleic acid methylation and proliferation of leukemia L1210 cells (Kramer et al., *Cancer Res.*, 50:3838–3842 (1990)).

Hence, methyltransferase activity can be associated with certain pathologies and other conditions, and its acitivity used as an indicator of diseases and conditions. Available methods for assessing the activity of methyltransferases, including SAM-dependent methyltransferases, require the use of radioactively labelled reagents and/or sophisticated and expensive analytical equipment such as HPLCs and GC/MS. To fully exploit the diagnostic potential of the methyltransferase activity as a diagnostic aid, more convenient and cost-effective methods for assessing activity are required.

Therefore, it is an object herein to provide quick and simple methods for assaying the methyltransferase, such as SAM-dependent methyltransferase, activity. It is also an object herein to provide for methods for screening for modulators of such methyltransferases, including SAM-dependent methyltransferases.

SUMMARY

Provided herein are methods for assessing the activity of methyltransferases. The methods are exemplified with references to SAM-dependent methyltransferase, but can be applied to any transferase. In particular, methods for assaying the activity of a S-adenosylmethionine (SAM)-dependent methyltransferase are provided. The methods are practiced by contacting the SAM-dependent methyltransferase with a substrate of the methyltransferase in the presence of a methyl donor, such as SAM, whereby a methyl group is transferred from donor, SAM, to a substrate for the methyltransferase. In the instance where SAM is the donor, SAM is converted to S-adenosylhomocysteine (SAH), which is a demethylated donor. The resulting product, in this instance SAH, is contacted with an mutant binding enzyme, in this instance a mutant SAH-binding enzyme, which has binding affinity for SAH (or other product) but has attenuated catalytic activity. The binding between the mutant enzyme and the product, in this instance SAH is detected, and correlated with the amount of product, SAH, which in turn is correlated with the level of activity of the methyltransferase that generated the product.

This reaction, exemplified with reference to SAM-dependent methyltransferase, is summarized as follows:

R is selected from proteins, DNA, RNA, lipids and small molecules.

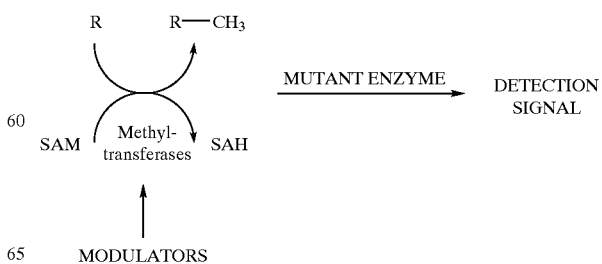

Hence, a reaction scheme, such as the above, can be used to screen for compounds that modulate the activity of the selected methyltransferase. Modulators include inhbitors, which could serve, for example, as anticancer agents, anti-neurodegenerative agents, and anti-inflammatory agents.

Hence performance of the methods provided herein requires a methy donor, and a mutant enzyme that binds to the demethylated donor, but does not catalyze further reaction thereof. Methods of use and preparation of such mutant binding enzymes are described herein and also described and exemplified in copending U.S. application Ser. No. 09/347,878 to Chong-Shen Yuan, filed Jul. 6, 1999, entitled "COMPOSITIONS AND METHODS FOR ASSAYING ANALYTES" and U.S. application Ser. No. 09/457,205 to Chong-Shen Yuan, filed Dec. 6, 1999, entitled "COMPOSITIONS AND METHODS FOR ASSAYING ANALYTES." U.S. application Ser. No. 09/457,205, which are incorporated by reference in their entirety.

Also provided herein, are methods for identifying modulators of methyltransferases. The methods assess methyltransferase activity by detecting binding of a mutant binding enzyme to the demethylated methyl donor in the methyltransferase reaction. The reactions are performed in the presence of a test compound, and any change (relative to a control) in the amoung mutant enzyme-demethylated product form is indicative of an effect of the test compound on the methyltransferase. Typically the control is the amount of binding in the absence of the test compound or comparison with any suitable standard curve prepared for this purpose. Compounds that result in an altered amount of mutant binding enzyme-methyl donor complex compared to a suitable control are selected for further screening.

The exemplified methods are described with reference to SAM-dependent methyltransferase using SAM as the methyl donor, and SAH as the demethylated product that forms a complexewith the mutant enzyme. In an exemplary embodiment the methods for identifying modulators of methyltransferase activity are practiced by contacting the SAM-dependent methyltransferase with a substrate of the methyltransferase in the presence of SAM and a test substance, whereby a methyl group is transferred from SAM to the substrate and SAM is converted to S-adenosylhomocysteine (SAH); contacting the SAH with a mutant SAH-binding enzym that has binding affinity for SAH but has attenuated catalytic activity, and detecting binding between SAH and the mutant SAH-binding enzyme to detect or determine the presence or amount of SAH, whereby the activity of the SAM-dependent methyltransferase is assessed; and comparing the assessed activity of the SAM-dependent methyltransferase with a control.

If the activity measured differs from the activity measured in a control reaction, such as the same reaction performed in the absence of the test compound or a standard curve or other measurement whereby the aunmodulated activity of the methyltransferase can be assessed, then the test substance modulates the activity of the methyltransferase, such as the SAM-dependent methyltransferase.

In certain embodiments, the control is performed by contacting the SAM-dependent methyltransferase with a substrate of the methyltransferase in the presence of SAM, whereby a methyl group is transferred from SAM to the substrate and SAM is converted to S-adenosylhomocysteine (SAH), contacting the SAH with a mutant SAH-binding enzyme that has binding affinity for SAH but has attenuated catalytic activity, and detecting binding between SAH and the mutant SAH-binding enzyme to detect or determine the presence or amount of SAH, whereby the activity of the SAM-dependent methyltransferase is assessed.

Further provided herein are compositions, kits and articles of manufacture to be used in the above assay or screening methods.

The methyltransferases that can be assayed or screened against in the above methods include, but are not limited to, protein methyltransferases, nucleic acid methyltransferases, lipid methyltransferases, polysaccharide methyltransferases and other small molecule methyltransferases. Particularly preferred are SAM-dependent methyltransferases.

The methyltransferase can be isolated from a target cell. Hence in a specific emdobiment, the methyltransferase is a SAM-dependent methyltransferase that is isolated from a target cell, the test substance to be screened for is a therapeutic compound, and the screening assay is used to assess whether the target cell responds to the test substance For use with the SAM-dependent methyl transferase the mutant enzyme binds to the demethylated product SAH. In a preferred embodiment, the mutant SAH-binding enzyme used is a mutant SAH hydrolase, which mutant SAH hydrolase substantially retains its binding affinity or has enhanced binding affinity for SAH but has attenuated catalytic activity. In another preferred embodiment, the assay or screening is used in a high throughput mode, i.e., the activities of a plurality of SAM-dependent methyltransferases are assayed simultaneously and/or a plurality of test substances are screened for simultaneously.

DETAILED DESCRIPTION

A. DEFINITIONS
B. METHODS FOR ASSAYING SAM-DEPENDENT Methyltransferase
  1. SAM-dependent methyltransferase
  2. Mutant SAH-binding enzyme
    a. Nucleic acids encoding SAH-binding enzymes
    b. Selecting and producing mutant SAH-binding enzymes
    c. Mutant SAH hydrolase
C. METHODS FOR ASSESSING THE ACTIVITY OF METHYLTRANSFERASES AND METHODS OF DIAGNOSIS AND DRUG DISCOVERY BASED THEREON
  1. Methods for screening for compounds that modulate that activity of methyltransferases
  2. Methods for screening for methyltransferase modulators for diagnosis and methods for detecting and identifying methyltransferase substrates
  3. High throughput screening (HTS) assays
    a. HTS instrumentation and capabilities
    b. Detection technologies
      1) Radiochemical methods
      2) Non-isotopic detection methods
        a) Colorimetry and luminescence
        b) Resonance energy transfer
        c) Time-resolved fluorescence
        d) Cell-based fluorescence assays
        e) Fluorescence polarization
        f) Fluorescence correlation spectroscopy
    c. Miniaturization
  4. Test Substances Combinatorial libraries
  5. Methods for detecting levels of DNA and RNA methylation
D. LABELLING OF MUTANT SAH-BINDING ENZYMES
  1. Conjugation
    a. Fusion proteins b. Chemical conjugation
1) Heterobifunctional cross-linking reagents
2) Exemplary Linkers
a) Acid cleavable, photocleavable and heat sensitive linkers
b) Other linkers for chemical conjugation
c) Peptide linkers
2. Selection of facilitating agents
a. Protein binding moieties
1) Interaction trap/two-hybrid system
2) Phage-based expression cloning
3) Detection of protein-protein interactions
b. Epitope tags
c. IgG binding proteins
1) pEZZ 18 Protein A gene fusion vector
2) pRIT2T Protein A gene fusion vector
3) The IgG Sepharose 6 fast flow system
d. β-galactosidase fusion proteins
e. Nucleic acid binding moieties
1) DNA binding proteins
2) RNA binding proteins
3) Preparation of nucleic acid binding proteins
4) Assays for identifying nucleic acid binding proteins
a) Mobility shift DNA-binding assay
b) Basic mobility shift assay procedure
c) Competition mobility shift assay
d) Antibody supershift assay
e) Methylation and uracil interference assay
1) Methylation interference assays
2) Uracil interference assay
3) DNase I footprint analysis
4) Screening a λgt11 expression library with recognition-site DNA
5) Rapid separation of protein-bound DNA from free DNA
f. Lipid binding moieties
g. Polysaccharide binding moieties
h. Metal binding moieties
i. Other facilitating agents
1) Peroxidase
2) urease
3) Alkaline phosphatase
4) Luciferase
5) Glutathione S-transferase
6) Defense proteins
7) Fluorescent moieties
E. IMMOBILIZATION OF MUTANT SAH-BINDING ENZYMES
F. SAMPLE COLLECTION
G. EXAMPLES
1. Preparation of mutant SAH hydrolase-encoding nucleic acid
a. Single-strand DNA-based mutagenesis
b. Design of primers for point mutation
c. PCR-based mutagenesis method
d. Identification of substrate trapping SAH hydrolase
2. Large scale overexpression and purification of wild type and mutant forms of SAH hydrolases
a. Purification
b. Storage of the purified SAH hydrolase
c. Assays for enzyme activity
d. Assay for binding affinity (Kd)
3. Preparation of reagents
a. Preparation of fluorophore-labeled Ado and SAH analogs
1) Method 1
2) Method 2
3) Method 3
4) Method 4
b. Coating mutant SAH hydrolase on microtiter well (96 well plate)
c. Preparation of standard samples and chemical reagents
1) Construction of a standard Hcy curve
2) Wild type SAH hydrolase solution
3) Tri-n-butylphosphine (TBP) solution
4) Fluorophore-labeled Ado-Cys solution
5) SAH hydrolase inhibitor solution
6) Multi-enzyme solution
7) Washing solution
4. Assays of Hcy using the mutant SAH enzyme
a. Plasma Hcy assay procedure 1
1) Conversion of Hcy to SAH
2) Removal of remaining Ado and enzyme inhibitor
3) Trapping the formed SAH onto the mutant SAH hydrolase
4) Washing
5) Binding of fluorophore-labeled Ado-Cys to the mutant enzyme
6) Detection of the mutant SAH hydrolase-bound fluorophore-labeled Ado-Cys
b. Alternative Hcy assay
1) Pre-coating SAH on microtiter well
2) Fluorophore-labeled mutant SAH hydrolase
c. Plasma Hcy assay procedure 2
1) Conversion of Hcy to SAH
2) Removal of remaining Ado and enzyme inhibitor
3) Competition binding of SAH to the Mutant SAH hydrolase
4) Detection of the fluorophore-labeled mutant SAH hydrolase bound to the microtiter well A. Definitions Unless defined otherwise, all technical and scientific terms used herein have the same meaning as is commonly understood by one of ordinary skill in the art to which this invention belongs. All patents, applications, published applications and other publications and sequences from GenBank and other data bases referred to herein are incorporated by reference in their entirety.

As used herein, a methyltransferase refers to any enzyme that transfers a methyl group from a methyl donor to a substrate and converts the donor into a demethylated donor, which is then detected and or quantitated by binding to a mutant binding enzyme that in its unmodified form binds to and catalyzes a further reaction thereof. The mutant enzyme binds to the demethylated donor with substantially the same affinity as the wild-type, but has attenuated, typically 50%, more preferably 20%, most preferably 10% or less of wild-type.

As used herein, "S-adenosylmethionine (SAM)-dependent methyltransferase" refers to an enzyme that transfers a methyl group from SAM to a substrate and converts SAM to S-adenosylhomocysteine (SAH). SAM-dependent methyltransferase can transfer a methyl group from SAM to a carbon, an oxygen, a nitrogen or a sulfur atom of a substrate, and the SAM-dependent methyltransferase is thereby further classified as a C-, O-, N-, or S-methyltransferase, respectively. Any such SAM-dependent methyltransferase, including those with conservative amino acid substitutions that do not substantially alter its activity are contemplated herein.

As used herein, "substrate of a SAM-dependent methyltransferase" refers to a substance that receives the methyl group from SAM in a reaction catalyzed by the SAM-dependent methyltransferase. Examples of the substrates of the SAM-dependent methyltransferases include proteins, nucleic acids, lipids, polysaccharides and other small molecules. As used herein, "SAM" is not considered a "substrate of a SAM-dependent methyltransferase."

As used herein, "protein SAM-dependent methyltransferase" refers to an enzyme that transfers a methyl group from SAM to a protein substrate and converts SAM to SAH.

As used herein, "nucleic acid SAM-dependent methyltransferase" refers to an enzyme that transfers a methyl group from SAM to a nucleic acid substrate, such as a DNA or a RNA, and converts SAM to SAH.

As used herein, "lipid SAM-dependent methyltransferase" refers to an enzyme that transfers a methyl group from SAM to a lipid substrate and converts SAM to SAH.

As used herein, "polysaccharide SAM-dependent methyltransferase" refers to an enzyme that transfers a methyl group from SAM to a polysaccharide substrate and converts SAM to SAH.

As used herein, "small molecule SAM-dependent methyltransferase" refers to an enzyme that transfers a methyl group from SAM to a small molecule substrate and converts SAM to SAH.

In all instances the methyltransferases encompass variants and mutants thereof, particularly those with conservative amino acid subtitutions (see, e.g., Table 1, below), that retain the methyltransferring activity.

As used herein, "macromolecule" refers to a molecule that, without attaching to another molecule, is capable of generating an antibody that specifically binds to the macromolecule.

As used herein, "small molecule" refers to a molecule that, without forming homo-aggregates or without attaching to a macromolecule or adjuvant, is incapable of generating an antibody that specifically binds to the small molecule. Preferably, the small molecule has a molecule weight that is about or less than 10,000 daltons. More preferably, the small molecule has a molecule weight that is about or less than 5,000 dalton.

As used herein, "enzyme" refers to a protein specialized to catalyze or promote a specific metabolic reaction. Generally, enzymes are catalysts, but for purposes herein, such "enzymes" include those that would be modified during a reaction. Since the enzymes are modified to eliminate or substantially eliminate catalytic activity, they will not be so-modified during a reaction.

As used herein, "S-adenosylhomocysteine (SAH)-binding enzyme" refers to an enzyme that uses SAH as its co-enzyme, co-factor, or as a substrate. For example, SAH hydrolase is a SAH-binding enzyme. It is intended that SAH-binding enzymes include those conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p.224).

Such substitutions are preferably made in accordance with those set forth in TABLE 1 as follows:

TABLE 1

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, the "amino acids," which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, "a mutant analyte-binding enzyme" (used interchangeably with "modified enzyme" and "substrate trapping enzyme" that substantially retains its binding affinity or has enhanced binding affinity for the analyte or an immediate analyte enzymatic conversion product" refers to a mutant form of an analyte-binding enzyme that retains sufficient binding affinity for the analyte to be detected in the process or method, particularly assay, of interest. Typically this is at least about 10%, preferably at least about 50% binding affinity for the analyte or an immediate analyte enzymatic conversion product, compared to its wildtype counterpart. Preferably, such mutant analyte-binding enzyme retains 60%, 70%, 80%, 90%, 100% binding affinity for the analyte or an immediate analyte enzymatic conversion product compared to its wildtype counterpart, or has a higher binding affinity than its wildtype counterpart. Such mutant analyte-binding enzyme is herein referred to as a "substrate trapping enzyme", i.e., a molecule that specifically binds to a selected analyte or target molecule, but does not catalyze conversion thereof.

As used herein, "a mutant SAH-binding enzyme" (used interchangeably with "modified enzyme" and "SAH trapping enzyme" that substantially retains its binding affinity or has enhanced binding affinity for SAH refers to a mutant form of a SAH-binding enzyme that retains sufficient binding affinity for SAH to be detected in the process or method, particularly assay, of interest. Typically this is at least about 10%, preferably at least about 50% binding affinity for SAH, compared to its wildtype counterpart. Preferably, such mutant SAH-binding enzyme retains 60%, 70%, 80%, 90%, 100% binding affinity for SAH compared to its wildtype counterpart, or has a higher binding affinity than its wildtype counterpart. Such mutant SAH-binding enzyme is herein referred to as a "SAH trapping enzyme", i.e., a molecule that specifically binds to SAH, but does not catalyze conversion thereof.

As used herein, "attenuated catalytic activity" refers to a mutant SAH-binding enzyme that retain sufficiently reduced catalytic activity to be useful as a "pseudo-antibody", i.e, a molecule used in place of an antibody in immunoassay formats. The precise reduction in catalytic activity for use in the assays can be empirically determined for each assay. Typically, the enzyme will retain less than about 50% of one of its catalytic activities or less than 50% of its overall catalytic activities compared to its wildtype counterpart. Preferably, a mutant analyte-binding enzyme retains less than 40%, 30%, 20%, 10%, 1%, 0.1%, or 0.01% of one of its catalytic activities or its overall catalytic activities compared to its wildtype counterpart. More preferably, a mutant SAH-binding enzyme lacks detectable level of one of its catalytic activities or its overall catalytic activities compared to its wildtype counterpart. In instances in which catalytic activity is retained and/or a further reduction thereof is desired, the contacting step can be effected in the presence of a catalysis inhibitor. Such inhibitors, include, but are not limited to, heavy metals, chelators or other agents that bind to a co-factor required for catalysis, but not for binding, and other such agents.

As used herein the term "assessing" is intended to include quantitative and qualitative determination in the sense of obtaining an absolute value for the amount or concentration of SAH present in the sample, and also of obtaining an index, ratio, percentage, visual or other value indicative of the level of SAH in the sample. Assessment may be direct or indirect and the chemical species actually detected need not of course be SAH itself but may for example be a derivative thereof or some further substance.

As used herein, "test substance" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on a SAM-dependent methyltransferase is determined by the disclosed and/or claimed methods herein.

As used herein, "target cell" refers to a cell that expresses a SAM-dependent methyltransferase naturally.

As used herein, "serum" refers to the fluid portion of the blood obtained after removal of the fibrin clot and blood cells, distinguished from the plasma in circulating blood.

As used herein, "plasma" refers to the fluid, noncellular portion of the blood, distinguished from the serum obtained after coagulation.

As used herein, a conjugate refers to the compounds provided herein that include one or more mutant SAH-binding enzymes and one or more facilitating agents. These conjugates include those produced by recombinant means as fusion proteins, those produced by chemical means, such as by chemical coupling, through, for example, coupling to sulfhydryl groups, and those produced by any other method whereby at least one mutant SAH-binding enzyme is linked, directly or indirectly via linker(s) to a facilitating agent.

As used herein, a facilitating agent, is any moiety, such as a protein or effective portion thereof, that promotes or facilitates, for example, preferably:
  i) affinity isolation or purification of the conjugate;
  ii) attachment of the conjugate to a surface;
  iii) detection of the conjugate or complexes containing the conjugate; or
  iv) targeted delivery of the conjugate to a selected tissue or cell.

As used herein, "substantially pure" means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in vitro systems designed to test or use such activities.

As used herein, a "receptor" refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: cell membrane receptors, surface receptors, internalizing receptors, and antibodies and antisera reactive with specific antigenic determinants, drugs, polynucleotides, nucleic acids, peptides, cofactors, lectins, sugars, polysaccharides, cells, cellular membranes, and organelles.

As used herein, "antibody" includes antibody fragments, such as Fab fragments, which are composed of a light chain and the variable region of a heavy chain.

As used herein, "humanized antibodies" refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, "production by recombinant means" refers to production methods that use recombinant nucleic acid methods that rely on well known methods of molecular biology for expressing proteins encoded by cloned nucleic acids.

As used herein, "substantially identical" to a product means sufficiently similar so that the property of interest is sufficiently unchanged so that the substantially identical product can be used in place of the product.

As used herein, "equivalent," when referring to two sequences of nucleic acids means that the two sequences in question encode the same sequence of amino acids or equivalent proteins. It also encompasses those that hybridize under conditions of moderate, preferably high stringency, whereby the encoded protein retains desired properties.

As used herein, when "equivalent" is used in referring to two proteins or peptides, it means that the two proteins or peptides have substantially the same amino acid sequence with only conservative amino acid substitutions [see, e.g., Table 1, above] that do not substantially alter the activity or function of the protein or peptide.

When "equivalent" refers to a property, the property does not need to be present to the same extent [e.q., two peptides can exhibit different rates of the same type of enzymatic activity], but the activities are preferably substantially the same. "Complementary," when referring to two nucleic acid molecules, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: "stringency of hybridization" in determining percentage mismatch is as follows:

1) high stringency: 0.1×SSPE, 0.1% SDS, 65° C.;
2) medium stringency: 0.2×SSPE, 0.1% SDS, 50° C. (also referred to as moderate stringency); and
3) low stringency: 1.0×SSPE, 0.1% SDS, 50° C.

It is understood that equivalent stringencies may be achieved using alternative buffers, salts and temperatures.

The term "substantially" identical or homologous or similar varies with the context as understood by those skilled in the relevant art and generally means at least 70%, preferably means at least 80%, more preferably at least 90%, and most preferably at least 95% identity.

As used herein, a "composition" refers to any mixture of two or more products or compounds. It may be a solution, a suspension, liquid, powder, a paste, aqueous, non-aqueous or any combination thereof.

As used herein, a "combination" refers to any association between two or more items.

As used herein, "fluid" refers to any composition that can flow. Fluids thus encompass compositions that are in the form of semi-solids, pastes, solutions, aqueous mixtures, gels, lotions, creams and other such compositions.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship. of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.,* 266:19867–19870 (1991)) can be inserted immediately 5' of the start codon and may enhance expression. The desirability of (or need for) such modification may be empirically determined.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "replication" refers to a process of DNA-dependent DNA synthesis where the DNA molecule is duplicated to give identical copies.

As used herein, "transcription" refers to a process of DNA-dependent RNA synthesis.

As used herein, "recombination" refers to a reaction between homologous sequences of DNA. The critical feature is that the enzymes responsible for recombination can use any pair of homologous sequences as substrates, although some types of sequences may be favored over others. Recombination allows favorable or unfavorable mutations to be separated and tested as individual units in new assortments.

As used herein, "DNA structure maintenance" refers to DNA sequences, through binding to proteins, that maintain the DNA molecule in particular structures such as chromatids, chromatins or chromosomes.

As used herein, "DNA polymerase" refers to an enzyme that synthesizes DNA using a DNA as the template. It is intended to encompass DNA polymerase with conservative amino acid substitutions that do not substantially alter its activity.

As used herein, "DNA-dependent RNA polymerase" or "transcriptase" refers to an enzyme that synthesizes RNA using a DNA as the template. It is intended to encompass DNA-dependent RNA polymerase with conservative amino acid substitutions that do not substantially alter its activity.

As used herein, "DNAase" refers to an enzyme that attacks bonds in DNA. It is intended to encompass DNAase with conservative amino acid substitutions that do not substantially alter its activity.

As used herein, "DNA ligase" refers to an enzyme that catalyses the formation of a phosphodiester bond to link two adjacent bases separated by a nick in one strand of double helix of DNA. It is intended to encompass DNA ligase with conservative amino acid substitutions that do not substantially alter its activity.

As used herein, "DNA topoisomerase" refers to an enzyme that can change the linking number of DNA. It is intended to encompass DNA topoisomerase with conservative amino acid substitutions that do not substantially alter its activity.

As used herein, "DNA transposase" refers to an enzyme that is involved in insertion of a transposon at a new site. It is intended to encompass DNA transposase with conservative amino acid substitutions that do not substantially alter its activity.

As used herein, "Transposon" refers to a DNA sequence that is able to replicate and insert one copy at a new location in the genome.

As used herein, "DNA kinase" refers to an enzyme that phosphorylates DNA. It is intended to encompass DNA kinase with conservative amino acid substitutions that do not substantially alter its activity.

As used herein, "restriction enzyme" refers to an enzyme that recognizes specific short sequences of DNA and cleave the duplex at the recognition site or other site. It is intended to encompass a restriction enzyme with conservative amino acid substitutions that do not substantially alter its activity.

As used herein, "rRNA" or "ribosomal RNA" refers to the RNA components of the ribosome, a compact ribonucleoprotein particle that assembles amino acids into proteins.

As used herein, "mRNA" or "messenger RNA" refers to the RNA molecule that bears the same sequence of the DNA coding strand and is used as the template in protein synthesis.

As used herein, "tRNA" or "transfer RNA" refers to the RNA molecule that carries amino acids to the ribosome for protein synthesis.

As used herein, "reverse transcription" refers to the RNA-dependent DNA synthesis.

As used herein, "RNA splicing" refers to the removal of introns and joining of exons in RNA so that introns are spliced out and exons are spliced together.

As used herein, "RNA-dependent DNA polymerase" or "reverse transcriptase" refers to an enzyme that synthesizes DNA using a RNA as the template. It is intended to encompass a RNA-dependent DNA polymerase with conservative amino acid substitutions that do not substantially alter its activity.

As used herein, "RNA-dependent RNA polymerase" refers to an enzyme that synthesizes RNA using a RNA as the template. It is intended to encompass a RNA-dependent RNA polymerase with conservative amino acid substitutions that do not substantially alter its activity.

As used herein, "RNA ligase" refers to an enzyme that catalyses the formation of a phosphodiester bond to link two adjacent bases separated by a nick in one strand of RNA. It is intended to encompass a RNA ligase with conservative amino acid substitutions that do not substantially alter its activity.

As used herein, "RNA maturase" refers to an enzyme that catalyses the removal of intron in the RNA splicing. It is intended to encompass a RNA maturase with conservative amino acid substitutions that do not substantially alter its activity.

As used herein, "luminescence" refers to the detectable EM radiation, generally, UV, IR or visible EM radiation that is produced when the excited product of an exergic chemical process reverts to its ground state with the emission of light.

Chemiluminescence is luminescence that results from a chemical reaction. Bioluminescence is chemiluminescence that results from a chemical reaction using biological molecules or synthetic versions or analogs thereof as substrates and/or enzymes.

As used herein, "bioluminescence," which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein (luciferase) that is an oxygenase that acts on a substrate luciferin (a bioluminescence substrate) in the presence of molecular oxygen and transforms the substrate to an excited state, which upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives, for example, bacterial luciferin or firefly luciferase.

As used herein, "luciferase" refers to oxygenases that catalyze a light emitting reaction. For instance, bacterial luciferases catalyze the oxidation of flavin mononucleotide [FMN] and aliphatic aldehydes, which reaction produces light. Another class of luciferases, found among marine arthropods, catalyzes the oxidation of Cypridina [Vargula] luciferin, and another class of luciferases catalyzes the oxidation of Coleoptera luciferin.

Thus, luciferase refers to an enzyme or photoprotein that catalyzes a bioluminescent reaction [a reaction that produces bioluminescence]. The luciferases, such as firefly and Renilla luciferases, that are enzymes which act catalytically and are unchanged during the bioluminescence generating reaction. The luciferase photoproteins, such as the aequorin photoprotein to which luciferin is non-covalently bound, are changed, such as by release of the luciferin, during bioluminescence generating reaction. The luciferase is a protein that occurs naturally in an organism or a variant or mutant thereof, such as a variant produced by mutagenesis that has one or more properties, such as thermal stability, that differ from the naturally-occurring protein. Luciferases and modified mutant or variant forms thereof are well known. For purposes herein, reference to luciferase refers to either the photoproteins or luciferases.

As used herein, "peroxidase" refers to an enzyme that catalyses a host of reactions in which hydrogen peroxide is a specific oxidizing agent and a wide range of substrates act as electron donors. It is intended to encompass a peroxidase with conservative amino acid substitutions that do not substantially alter its activity. Peroxidases are widely distributed in nature and are produced by a wide variety of plant species. The chief commercially available peroxidase is horseradish peroxidase.

As used herein, "urease" refers to an enzyme that catalyses decomposition of urea to form ammonia and carbon dioxide. It is intended to encompass an urease with conservative amino acid substitutions that do not substantially alter its activity. Urease is widely found in plants, animals and microorganisms.

As used herein, "alkaline phosphatases" refers to a family of functionally related enzymes named after the tissues in which they predominately appear. Alkaline phosphatases carry out hydrolase/transferase reactions on phosphate-containing substrates at a high pH optimum. It is intended to encompass an alkaline phosphatases with conservative amino acid substitutions that do not substantially alter its activity.

As used herein, "glutathione S-transferase" refers to an ubiquitous family of enzymes with dual substrate specificities that perform important biochemical functions of xenobiotic biotransformation and detoxification, drug metabolism, and protection of tissues against peroxidative damage. The basic reaction catalyzed by glutathione S-transferase is the conjugation of an electrophile with reduced glutathione (GSH) and results in either activation or deactivation/detoxification of the chemical. It is intended to encompass a glutathione S-transferase with conservative amino acid substitutions that do not substantially alter its activity.

As used herein, high-throughput screening (HTS) refers to processes that test a large number of samples, such as samples of diverse chemical structures against disease targets to identify "hits" (see, e.g., Broach et al., High throughput screening for drug discovery, *Nature*, 384:14–16 (1996); Janzen et al., High throughput screening as a discovery tool in the pharmaceutical industry, Lab Robotics Automation, 8261–265 (1996); Fernandes, *J. Biomol. Screening*, 2:1 (1997); Burbaum et al., New technologies for high-throughput screening, *Curr. Opin. Chem. Biol.*, 1:72–78 (1997)). HTS operations are highly automated and computerized to handle sample preparation, assay procedures and the subsequent processing of large volumes of data.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.*, 11:1726 (1972)).

For clarity of disclosure, and not by way of limitation, the detailed description is divided into the subsections that follow.

B. METHODS FOR ASSAYING METHYLTRANSFERASES

Provided herein are method for assaying the activity of methyltransferases. The activities of particular methyl transferases can be associated with various conditions and diseases. Hence, these methods can be used to diagnose or detect such conditions and diseases. The particular disease or condition that is diagnosed is dependent upon the methyltransferase with which the methyl donor functions, and further the selected substrate. Different types of methyltransferases react with different types of substrates, and particular methyltransferases may have specific substrates. By assessing the activity of the methyltransferase in a sample, such as a body tissue or body fluid sample, the level of the activity can be correlated with a particular disease or disorder. In addition, the presence or absence of a particular substrate in a body tissue or body fluid sample may be assessed by selecting a particular methyltransferase specific for the substrate and assessing the activity of the methyltransferase that is contacted with a biological sample, such as a body tissue or fluid. The level of activity of the methyltransferase is indicative of the presence and amount of the substrate present in the sample.

In addition, the ability to assess the activity of methyltransferase, proivdes a means to screen for compounds that modulate the activity of a methyltransferase. Compounds that modulate the activity of a methyltransferase would be candidates for therapeutic agents for treatments of diseases in which altered methyltransferase activity play a role. The methyltransferase can play either a direct or indirect role in the condition or disease.

As noted, these methods are described with reference to SAM-dependent methyltransferases, but can be practiced with other transferases and their cognate methyl donors.

In particular embodiments, provided herein are methods for assaying the activity of a S-adenosylmethionine (SAM)-dependent methyltransferase by contacting the SAM-dependent methyltransferase with a substrate of the methyltransferase in the presence of SAM, whereby a methyl group is transferred from SAM to the substrate and SAM is converted to S-adenosylhomocysteine (SAH); contacting the resulting SAH with a mutant SAH-binding enzyme that has binding affinity for SAH but has attenuated catalytic activity; and detecting binding between SAH and the mutant SAH-binding enzyme to detect or determine the presence or amount of SAH, whereby the activity of the SAM-dependent methyltransferase is assessed. In performing the methods, all reagents may be added simultaneously, or preferably the substrate is first added and the mutant binding enzyme added subsequently. Preferably the reactions are performed sequentially without purifying or isolating the SAH.

In a preferred embodiment, the assay is conducted in a high throughput mode, i.e., the activities of a plurality of SAM-dependent methyltransferases are assayed simultaneously. For example, the assay can be conducted in a multi-well (e.g., 24-, 48-, 96-, or 384- or higher density well), chip or array format. In other embodiments, the assay is conducted on a point of care device.

Also provided herein are kits for assaying the activity of a SAM-dependent methyltransferase. The comination contains a substrate of the methyltransferase to be assayed; SAM; a mutant SAH-binding enzyme that retains at least substantially its binding affinity for SAH but has attenuated catalytic activity; and reagents for detecting binding between SAH and the SAH-binding enzyme. Preferably, the reagent for detecting binding between SAH and the SAH-binding enzyme is a labelled SAH, a labelled mutant SAH-binding enzyme, or a derivative or an analog thereof. The kit can also include instructions for assaying the activity of a SAM-dependent methyltransferase. Each component in the kit may be suitably packaged for storage and use thereof; each component will be formulated in a suitable composition for use in the methods.

1. SAM-dependent Methyltransferase

Any SAM-dependent methyltransferase can be assayed by the methods provided herein. A variety of SAM-dependent methyltransferases are known (see generally Kagan and Clarke, *Arch. Biochem. Biophys.*, 310(2): 417–427 (1994); and Webb, *Enzyme Nomenclature, Academic Press, San Diego* (1992)).

Protein-methyltransferases

In a specific embodiment, the SAM-dependent methyltransferase to be assayed is a protein methyltransferase. Protein methyltransferases include, but but are not limited to, a protein carboxyl methyltransferase (Syed et al., *Biochemistry*, 32(9):2242–7 (1993)) or a protein (arginine) N-methyltransferase (Casellas and Jeanteur, *Biochim. Biophys. Acta*, 519(1):243–54 (1978); and Casellas and Jeanteur, *Biochim. Biophys. Acta*, 519(1):255–68 (1978)), such as an isoaspartyl O-methyltransferase, a Γ-glutamyl O-methyltransferase and an isoprenylcysteine O-methyltransferase.

Nucleic Acid Methyltransferases

SAM-dependent methyltransferases to be assayed include nucleic acid methyltransferases, including but are not limited to, a DNA methyltransferase, such as a DNA $m^5C$ methyltransferase or a DNA $m^6A$ methyltransferase (Posfai et al., *Nucleic Acids Res.,* 17:2421–2435 (1989); and Lauster et al., *J. Mol. Biol.,* 206:313–321 (1989)), which preferaby include an amino acid consensus sequence of hh(D/S)(L/P) FXGXG (Lauster et al., *J. Mol. Biol.,* 206:313–321 (1989)), where h is a hydrophobic amino acid residue (Wu et al., *J. Gen. Microbiol.,* 138:2101–2112 (1992)).

Further examples of SAM-dependent DNA methyltransferases that can be assayed include, but are not limited to, Pvull DNA (cytosine-N4)-methyltransferase (Adams and Blumenthal, *Biochemistry* 36(27):8284–92 (1997)), Kpnl DNA methyltransferase (Finta et al., *Gene* 164(1):65–9 (1995)), EcoKl methyltransferase (Powell et al., *Nucleic Acids Res.,* 23(6):967–74 (1995)), EcoP15 DNA methyltransferase (Ahmad and Rao, *Gene,* 142(1):67–71 (1994)), EcoK methyltransferase (Powell et al., *J. Mol. Biol.,* 234(1): 60–71 (1993)), phage T4 Dam DNA-[N6-adenine]-methyltransferase (Kossykh et al., *Nucleic Acids Res.,* 21(20):4659–62 (1993)), Dam methyltransferase from *Escherichia coli* (Wenzel and Guschlbauer, *Nucleic Acids Res.,* 21(19):4604–9 (1993)), Hhal DNA methyltransferase (Cheng et al., *Cell,* 74(2):299–307 (1993); and O'Gara et al., *J. Mol. Biol.,* 287(2):201–9 (1999)), and EcoRII methyltransferase (Som and Friedman, *J. Biol. Chem.,* 266(5): 2937–45 (1991)).

Also contempalted are RNA methyltransferases, including, but not limited to, mRNA, a rRNA and tRNA methyltransferases, such as the vaccinia virus mRNA (guanine-7-)methyltransferase (Higman and Niles, *J. Biol. Chem.,* 269(21):14982–7 (1994)), which include, for example, rRNA G methyltransferase, a rRNA N6 A methyltransferase and a rRNA N6,N6 A methyltransferase. The tRNA methyltransferase include, tRNA C5 U methyltransferase, tRNA N1 G methyltransferase and tRNA N2,N2 G methyltransferase.

Lipid Methyltransferases

Lipid methyltransferases include, but are not limited to, DHPB O-methyltransferase, DHHB O-methyltransferase, UbiG O-methyltransferase, phosphatidylethanolamine methyltransferase (Zawad and Sulser, *Eur. J. Biochem.,* 124(1–2):157–60 (1986)), phospholipid methyltransferase, cyclopropane fatty acid synthase, delta 24-sterol-C-methyltransferase (Shi et al., *J. Biol. Chem.,* 271(16):9384–9 (1996)), and delta 24(25)-sterol methyltransferase (Janssen and Nes, *J. Biol. Chem.,* 267(36):25856–63 (1992)).

Polysaccharide Methyltransferases

Polysaccharide methyltransferases that can be assayed by the methods herein include, but are not limited to, a NodS, which is an SAM-dependent methyltransferase that methylates chitooligosaccharides deacetylated at the non-reducing end (Geelen et al., *Mol. Microbiol.,* 17(2):387–97 (1995)).

Small Molecule Methyltransferases

Small molecule methyltransferase that can be assayed include, but are not limited to, small molecule O-methyltransferases, small molecule N-methyltransferases, a small molecule S-methyltransferases and porphyrin precursor C-methyltransferases. These include an N-acetylserotonin O-methyltransferase (Itoh et al., *J. Chromatogr. B. Biomed. Sci. Appl.,* 692(1):217–21 (1997)), a catechol O-methyltransferase (Vilbois et al., *Eur. J. Biochem.,* 222(2):377–86 (1994); and Yu, *Can. J. Biochem. Cell. Biol.,* 62(10):964–9 (1984)), a caffeic acid O-methyltransferase (Edwards and Dixon, *Arch. Biochem. Biophys.,* 287(2): 372–9 (1991); and Poeydomenge et al., *Plant Cell Physiol.,* 105(2):749–50 (1994)), a caffeoyl-coenzyme A O-methyltransferase (Pakusch et al., *Arch. Biochem. Biophys.,* 271(2):488–94 (1989)), an O-demethyl puromycin O-methyltransferase, a hydroxyneurosporene O-methyltransferase, a myo-inositol O-methyltransferase, a carminomycin O-methyltransferase, a tetracenomycin 3-O-methyltransferase, a tetracenomycin 8-O-methyltransferase, a midamycin O-methyltransferase, or an erythromycin biosynthesis O-methyltransferase.

Others include small molecule N-methyltransferases, such as a phenylethanolamine N-methyltransferase, a glycine N-methyltransferase, a guanidinoacetate N-methyltransferase (Takata and Fujioka, *Biochemistry,* 31 (17):4369–74 (1 992)), a histamine N-methyltransferase, or a diphthamide N-methyltransferase.

Small molecule S-methyltransferases incude a thioether S-methyltransferase (Mozier et al., *J. Biol. Chem.,* 263(10): 4527–31 (1988)), a thiopurine methyltransferase (VanLoon et al., *Biochem. Pharmacol.,* 44(4):775–85 (1992)), or a L-methionine S-methyltransferase (Pimenta et al., *Plant Physiol.,* 118(2):431–8 (1998); and James et al., *J. Biol. Chem.,* 270(38):22344–50 (1995)).

Other examples include, porphyrin precursor C-methyltransferase, such as a magnesium protoporphyrin IX methyltransferase (Hinchigeri et al., *FEBS Lett.,* 407(3): 337–42 (1997); Gibson et al., *FEBS Lett.,* 352(2):127–30 (1994); and Bollivar et al., *J. Bacteriol.,* 176(17):5290–6 (1994)); an uroporphyrinogen III methyltransferase (Leustek et al., *J. Biol. Chem.,* 272(5):2744–52 (1997); De Mot et al., *Gene,* 150(1):199–200 (1994); Robin et al., *J. Bacteriol.,* 173(15):4893–6 (1991); and Blanche et al., *J. Bacteriol.,* 173(15):4637–45 (1991)), a precorrin-2 methyltransferase (Thibaut et al., *J. Bacteriol.,* 172(11):6245–51 (1990)) or a precorrin-3 methyltransferase.

Further examples of small molecule methyltransferases that can be assayed include a salicylic acid carboxyl methyltransferase (Ross et al., *Arch. Biochem. Biophys.,* 367(1): 9–16 (1999)), a sialate-8-O-methyltransferase (Kelm et al., *Eur. J. Biochem.,* 251(3):874–84 (1998)), an isoeugenol O-methyltransferase (Wang et al., *Arch Biochem. Biophys.,* 349(1):153–60 (1998); and Wang et al., *Plant Physiol.,* 114(1):213–21 (1997)), a scoulerine-9-O-methyltransferase (Takeshita et al., *Plant Cell Physiol.,* 36(1):29–36 (1995)), a norcoclaurine 6-O-methyltransferase (Sato et al., *Eur. J. Biochem.,* 225(1):125–31 (1994)), an isoliquiritigenin 2'-O-methyltransferase (Maxwell et al., *Arch. Biochem. Biophys.,* 293(1):158–66 (1992)), a N-acylneuraminate 8-O-methyltransferase (Bergwerff et al., *Biochimie.,* 74(1):25–37 (1992)), a nucleolar 2'-O-methyltransferase (Segal and Eichler, *Arch. Biochem. Biophys.,* 275(2):334–43 (1989)), a macrocin O-methyltransferase (Bauer et al., *J. Biol. Chem.,* 263(30):15619–25 (1988)), a 3-methylquercetin 7-O-methyltransferase (Khouri et al., *Arch. Biochem. Biophys.,* 265(1):1–7 (1988)), a nicotinic acid-N-methyltransferase (Upmeier et al., *Arch. Biochem. Biophys.,* 262(2):445–54 (1988)), an avitexin 2"-O-rhamnoside 7-O-methyltransferase (Knogge and Weissenbock, *Eur. J. Biochem.,* 140(1):1 13–8 (1984)), a demethylmycophenolic acid O-methyltransferase (Muth and Nash, *Antimicrob. Agents Chemother.,* 8(3):321–7 (1975)), a cycloartenol methyltransferase (Wojciechowski et al., *Biochem. J.,* 136 (2):405–12 (1973)) and a loganic acid methyltransferase (Madyastha et al., *J. Biol. Chem.,* 248(7):2497–501 (1973)).

In a specific embodiment, the SAM-dependent methyltransferase to be assayed include at least one of the following amino acid consensus sequences (see generally Kagan and Clarke, *Arch. Biochem. Biophys.,* 310(2):417–427 (1994)):

motif I ((V/I/L)(L/V)(D/E)(V/I)G(G/C)G(T/P)G);

motif II ((P/G)(Q/T),(F/Y/A)DA(I/V/Y)(F/I)(C/V/L));

and motif III (LL(R/K)PGG(R/I/L)(L/I)(L/F/I/V)(I/L)).

In a preferred embodiment, the SAM-dependent methyltransferase incudes all the motifs I, II and III in the order of N'-I-II-III-C', the distance between the last amino acid residue of motif I and the first amino acid residue of motif II is from about 36 to about 90 amino acid residues, and the distance between the last amino acid residue of motif II and the first amino acid residue of motif III is from about 12 to about 38 amino acid residues.

In another preferred embodiment, the SAM-dependent methyltransferase only incudes the motif I. In another preferred embodiment, the SAM-dependent methyltransferase includes only the motifs I and III.

A preferred SAM-dependent methyltransferase is that having the amino acid sequence set forth in SEQ ID No. 2 or conservative variant thereof, and that is encoded by the sequence of nucleotides set forth in SEQ ID No. 1 or degenerate variants thereof (see, also, U.S. Pat. No. 5,876, 996 (SEQ ID NOs:1–2).

In another specific embodiment, the SAM-dependent methyltransferase with the following GenBank accession Nos. can be assayed: AW102461 (S-adenosyl-L-methionine:trans-caffeoyl-CoA 3-O-methyltransferase); AW102353 (S-adenosyl-L-methionine:trans-caffeoyl-CoA 3-O-methyltransferase; AW102160 (S-adenosyl-L-methionine:delta24-sterol-C-methyltransferase; AW102098 (S-adenosyl-L-methionine:delta24-sterol-C-methyltransferase; AW067623 (Sugar beet leaf S-adenosyl-L-methionine:trans-caffeoyl-CoA 3-O-methyltransferase); AF133053 (*Clarkia breweri* S-adenosyl-L-methionine:salicyclic acid carboxyl methyltransferase (SAMT); AW030960 (Tomato callus, S-adenosyl-methionine-sterol-C-methyltransferase); A1965359 (S-adenosyl-methionine-sterol-C-methyltransferase); AF137380 (*Arabidopsis thaliana* methionine S-methyltransferase); AF137023 (*Wollastonia biflora* methionine S-methyltransferase); Al939180 (S-adenosyl-L-methionine:transcaffeoyl-CoA-3-O-methyltransferase); Al938893 (S-adenosyl-L-methionine:trans-caffeoyl-CoA 3-O-methyltransferase); Al938529 (S-adenosyl-Methionine-sterol-C-methyltransferase; Al900873 (S-adenosyl-L-methionine:delta24-sterol-C-methyltransferase); Al822803 (S-adenosyl-L-methionine:trans-caffeoyl-CoA 3-O-methyltransferase); Al731031 (Cotton fiber *gossypium hirsutum* S-adenosyl-L-methionine:delta24-sterol-C-methyltransferase); Al727730 (Cotton fiber *gossypium hirsutum* S-adenosyl-L-methionine:delta24-sterol-C-methyltransferase); Al726950 (Cotton fiber *gossypium hirsutum* S-adenosyl-L-methionine:delta24-sterol-C-methyltransferase); AF144079 (*Zea mays* S-adenosyl-L-methionine:L-methionine S-methyltransferase); X87099 (*V.planifolia* S-adenosyl-L-methionine:caffeic acid 3-O-methyltransferase); Al496629 (S-adenosyl-L-methionine:delta24-sterol-C-methyltransferase; Al496365 (S-adenosyl-L-methionine:trans-caffeoyl-CoA 3-O-methyltransferase); Al494842 (S-adenosyl-L-methionine:delta24-sterol-C-methyltransferase); Al494713 (S-adenosyl-L-methionine:trans-caffeoyl-CoA 3-O-methyltransferase); Al443130 (S-adenosyl-L-methionine:trans-caffeoyl-CoA 3-O-methyltransferase); Al440769 (S-adenosyl-L-methionine:delta24-sterol-C-methyltransferase); Al438020 (S-adenosyl-L-methionine:trans-caffeoyl-CoA 3-O-methyltransferase); AF053766 (*Nicotiana tabacum* S-adenosyl-methionine cycloartenol-C24-methyltransferase); U81312 (*Nicotiana tabacum* S-adenosyl-methionine-sterol-C-methyltransferase); U20736 (*Medicago sativa* S-adenosyl-L-methionine:trans-caffeoyl-CoA 3-O-methyltransferase); AF045570 (*Zea mays* (S)-adenosyl-L-methionine:delta24-sterol methyltransferase); U63734 (*Arabidopsis thaliana* s-adenosyl-L-methionine-dependent uroporphyrinogen III methyltransferase (UPM1); AA680506 (*Trypanosoma brucei* S-adenyl-L-methionine-delta-(24)-sterol-L-methyltransferase); U71400 (*Arabidopsis thaliana* S-adenosyl-methionine-sterol-C-methyltransferase); U71108 (*Nicotiana tabacum* S-adenosyl-methionine-sterol-C-methyltransferase); U71107 (*Nicotiana tabacum* S-adenosyl-methionine-sterol-C-methyltransferase); L22203 (*Stellaria longipes* S-adenosyl-L-methionine:trans-caffeoyl-CoA 3-O-methyltransferase); D29809 (*Coptis japonica* S-adenosyl-L-methionine:scoulerine 9-O-methyltransferase); M63853 (*Medicago sativa* S-adenosyl-L-methionine:caffeic acid 3-O-methyltransferase); U43683 (*Glycine max* S-adenosyl-L-methionine:delta24-sterol-C-methyltransferase); U05002 (*Paracoccus denitrificans* S-adenosyl-L-methionine uroporphyrinogen III methyltransferase (nirE)); U19911 (*Zinnia elegans* S-adenosyl-L-methionine:caffeic acid 3-O-methyltransferase); M62874 (*Methanobacterium ivanovii* S-adenosyl-L-methionine:uroporphyrinogen III methyltransferase (CORA)); L40031 (*Arabidopsis thaliana* S-adenosyl-L-methionine:trans-caffeoyl-Coenzyme A 3-O-methyltransferase); U13151 (*Zinnia elegans* S-adenosyl-L-methionine:trans-caffeoyl-CoA 3-O-methyltransferase (CCoAOMT)); M62881 (*Bacillus megaterium* S-adenosy-L-methionine:uroporphyrinogen III methyltransferase (COBA)).

In still another specific embodiment, the SAM-dependent methyltransferase listed in the following Table 2 can be assayed (see, Table I of Kagan and Clarke, *Arch. Biochem. Biophys.*, 310(2):417–427 (1994)).

TABLE 2

| | Exemplary Methyltransferases | | | | | |
|---|---|---|---|---|---|---|
| | Enzyme | Gene[a] | EC Number | Organism | Motifs[b] | Accession[c] |
| Protein carboxyl MTases | Isoaspartyl O-MT | PIMT | 2.1.1.77 | human | I, II, III | A33404 |
| | Isoaspartyl O-MT | PIMT | 2.1.1.77 | bovine | I, II, III | A34242 |
| | Isoaspartyl O-MT | PIMT | 2.1.1.77 | mouse | I, II, III | M60320 |
| | Isoaspartyl O-MT | PIMT | 2.1.1.77 | rat | I, II, III | D11475 |
| | Isoaspartyl O-MT | PIMT | 2.1.1.77 | wheat | I, II, III | L07941 |
| | Isoaspartyl O-MT | pcm | 2.1.1.77 | *E. coli* | I, II, III | M63493 |

TABLE 2-continued

Exemplary Methyltransferases

| | Enzyme | Gene[a] | EC Number | Organism | Motifs[b] | Accession[c] |
|---|---|---|---|---|---|---|
| | λ-Glutamyl O-MT | cheR | 2.1.1.80 | E. coli | I, II, III | M13463 |
| | λ-Glutamyl O-MT | cheR | 2.1.1.80 | S. typhimurium | I, II, III | J02757 |
| | λ-Glutamyl O-MT | frzF | 2.1.1.80 | M. xanthus | I, II, III | M35200 |
| | Isoprenylcysteine O-MT | STE14 | 2.1.1.100 | yeast | nd | L15442 |
| Small molecule O-MTases | Acetylserotonin O-MT | HOMT | 2.1.1.4 | human | I, II, III | M83779 |
| | Acetylserotonin O-MT | HOMT | 2.1.1.4 | bovine | I, II, III | J02671 |
| | Acetylserotonin O-MT | HOMT | 2.1.1.4 | chicken | I, II, III | X62309 |
| | Catechol O-MT | COMT | 2.1.1.6 | human | I, II, III | M65212 |
| | Catechol O-MT | COMT | 2.1.1.6 | rat | I, II, III | M60754 |
| | Caffeic acid O-MT | (CAOMT) | 2.1.1.68 | maize | I, II, III | M73235 |
| | Caffeic acid O-MT | (CAOMT) | 2.1.1.68 | alfalfa | I, II, III | M63853 |
| | Caffeic acid O-MT | (CAOMT) | 2.1.1.68 | aspen | I, II, III | X62096 |
| | Caffeoyl CoA O-MT | (CCOMT) | 2.1.1.104 | parsley | I, II, III | M69184 |
| | O-Demethyl puromycin O-MT | dmpM | 2.1.1.38 | S. alboniger | I, II, III | M74560 |
| | Hydroxyneurosporene O-MT | crtF | | R. capsulatus | I, II, III | S04408 |
| | Myo-inositol O-MT | ImtI | 2.1.1.39/40 | M. crystallinum | I, II, III | M87340 |
| | Carminomycin O-MT | dnrK | | S. peucetius | I, II, III | L13453 |
| | Tetracenomycin 3-O-MT | tcmN | | S. glaucesens | I, II, III | M80674 |
| | Tetracenomycin 8-O-MT | tcmO | | S. glaucesens | I, II, III | M80674 |
| | Midamycin O-MT | mdmC | | S. mycarofaciens | I, II, III | M93958 |
| | Erythromycin biosynthesis O-MT | eryG | | S. erythraea | I, II, III | S18533 |
| Small molecule N-MTases | Phenylethanolamine N-MT | PNMT | 2.1.1.28 | human | I, II, III | J03280 |
| | Phenylethanolamine N-MT | PNMT | 2.1.1.28 | bovine | I, II, III | M36706 |
| | Phenylethanolamine N-MT | PNMT | 2.1.1.28 | rat | I, II, III | X14211 |
| | Phenylethanolamine N-MT | PNMT | 2.1.1.28 | mouse | I, II, III | L12687 |
| | Glycine-N-MT | GNMT | 2.1.1.20 | rabbit | I, II, III | D13307 |
| | Glycine-N-MT | GNMT | 2.1.1.20 | pig | I, II, III | D13308 |
| | Glycine-N-MT | GNMT | 2.1.1.20 | rat | I, II, III | X06150 |
| | Guanidinoacetate N-MT | (GANMT) | 2.1.1.2 | rat | I, II, III | J03588 |
| | Histamine N-MT | HNMT | 2.1.1.8 | rat | I, II, III | D10693 |
| | Diphthamide N-MT | DPH5 | 2.1.1.98 | yeast | nd | M83375 |
| Small molecule S-MTase | Thioether S-MT | (TSMT) | 2.1.1.96 | mouse | I, II, III | M88694 |
| Porphyrin precursor C-MTases | Precorrin-2-MT | cobI | | P. denitrificans | I | M59301 |
| | Precorrin-3 MT | cobF | | P. denitrificans | I, III | M59301 |
| | Precorrin-3 MT | cobJ | | P. denitrificans | I, III | M59301 |
| | Precorrin-3 MT | cobL | | P. denitrificans | I, II, III | M59301 |
| | Precorrin-3 MT | cobM | | P. denitrificans | I, III | M59301 |
| | Uroporphyrinogen III MT | cobA | 2.1.1.107 | B. megatarium | I, II, III | M62881 |
| | Uroporphyrinogen III MT | UMT | 2.1.1.107 | M. ivanovvii | I, III | M62874 |
| | Uroporphyrinogen III MT | UMT | 2.1.1.107 | Pseudomonas sp. | I, III | M32223 |
| | Uroporphyrinogen III MT | cysG | 2.1.1.107 | E. coli | I, II, III | P11098 |
| | Uroporphyrinogen III MT | cysG | 2.1.1.107 | S. typhimurium | I, II, III | P25924 |
| | Magnesium protoporphyrin MT | bchH | 2.1.1.11 | R. capsulatus | nd | M74001 |
| Lipid MTases | DHPB O-MT | COQ3 | 2.1.1.64 | rat | I, II, III | L20427 |
| | DHHB O-MT | COQ3 | 2.1.1.64 | yeast | I, II, III | M73270 |
| | UbiG O-MT | ubiG | | E. coli | I, II, III | M87509 |
| | Phosphatidylethanolamine MT | PEM1 | 2.1.1.17 | yeast | nd | M16987 |
| | Phosphatidylethanolamine MT | pmtA | 2.1.1.71 | R. spharoides | I, II, III | L07247 |
| | Phosphatidylethanolamine MT | PEM2 | 2.1.1.71 | yeast | nd | M16987 |
| | Phosphatidylethanolamine MT | pmtA | 2.1.1.71 | R. spharoides | I, II, III | L07247 |
| | Phospholipid MT | PEM2 | 2.1.1.71 | yeast | nd | M16988 |
| | Cyclopropane fatty acid synthase | cfa | 2.1.1.79 | E. coli | I, II, III | M98330 |
| RNA MTases | tRNA C5 U MT | trmA | 2.1.1.35 | E. coli | nd | M57568 |
| | tRNA N1 G MT | trmD | 2.1.1.31 | E. coli | II, III | X01818 |
| | tRNA N2, N2 G MT | trm1 | 2.1.1.32 | yeast | nd | M17193 |
| | rRNA G MT | grm | 2.1.1.51/52 | M. purpurea | nd | M55520 |
| | rRNA G MT | grm | 2.1.1.51/52 | S. tenebrarius | nd | S17717 |
| | rRNA G MT | grm | 2.1.1.51/52 | M. rosea | nd | M55521 |
| | rRNA MT | sgm | | S. zionensis | nd | S49806 |
| | rRNA MT | lmrB | | S. lincolnensis | III | X62867 |
| | rRNA MT | kamB | | S. tenebrarius | nd | M64625 |
| | rRNA MT | kamC | | S. hirsuta | nd | M64626 |
| | rRNA MT | carb | | S. thermotolerans | I | M16503 |
| | rRNA N6 A MT | lrm | 2.1.1.48 | S. lividans | I | JS0635 |
| | rRNA N6 A MT | ERMA | 2.1.1.48 | C. diphtheriae | I, III | X51472 |
| | rRNA N6 A MT | ermA | 2.1.1.48 | S. aureus | I, III | A25101 |
| | rRNA N6 A MT | ermBC | 2.1.1.48 | E. coli | I, III | B27739 |
| | rRNA N6 A MT | ermBP | 2.1.1.48 | C. perfringens | I, III | M77169 |
| | rRNA N6 A MT | ermC | 2.1.1.48 | S. aureus | I | M19652 |
| | rRNA N6 A MT | ermCd | 2.1.1.48 | C. diphtheriae | I | M36726 |
| | rRNA N6 A MT | ermD | 2.1.1.48 | B. licheniformis | I | M29832 |
| | rRNA N6 A MT | ermE | 2.1.1.48 | S. erythaeus | I | M11200 |

TABLE 2-continued

Exemplary Methyltransferases

| Enzyme | Gene[a] | EC Number | Organism | Motifs[b] | Accession[c] |
|---|---|---|---|---|---|
| rRNA N6 A MT | ermF | 2.1.1.48 | B. fragilis | I | A25157 |
| rRNA N6 A MT | ermG | 2.1.1.48 | B. sphaericus | I, III | M15332 |
| rRNA N6 A MT | ermJ | 2.1.1.48 | B. anthracis | I | L08389 |
| rRNA N6 A MT | ermK | 2.1.1.48 | B. licheniformis | I | B42473 |
| rRNA N6 A MT | ermM | 2.1.1.48 | S. epidermidis | I, III | A24497 |
| rRNA N6 A MT | ermR | 2.1.1.48 | L. reuteri | I, III | M64090 |
| rRNA N6 A MT | ermSF | 2.1.1.48 | S. fraediae | I, III | M19269 |
| rRNA N6, N6 A MT | ksgA | | E. coli | I | X06536 |

[a]Nonstandard gene designations in parentheses.
[b]nd, not detected.
[c]Accession numbers are from the Genbank/EMBL release 77 (Roman type), NBRF PIR release 36 (italicized type), and Swissprot release 24 (underlined).

2. The Mutant Binding Enzyme

Any mutant analyte-binding enzyme that substantially retains its binding affinity or has enhanced binding affinity for the demethylated product, such as SAH, but that has attenuated catalytic activity can be used to bind to the demethylated product in the methods herein. The amount of demethylated product is proportional to the activity of the methyltransferase.

Mutant SAH-binding Enzyme

Any mutant SAH-binding enzyme that has binding affinity for SAH but has attenuated catalytic activity can be used for assaying the activity of a SAM-dependent methyltransferase.

Mutant enzymes having the desired specificity can be prepared using routine mutagenesis methods. Residues to mutate can be identified by systematically mutating residues to different residues, and identifying those that have the desired reduction in catalytic activity and retention of binding activity for a particular substrate. Alternatively or additionally, mutations may be based upon predicted or known 3-D structures of enzymes, including predicted affects of various mutations (see, e.g., Turner et al., *Nature Structural Biol,* 5:369–376 (1998); Ault-Richié et al., *J. Biol. Chem.,* 269:31472–31478 (1994); Yuan et al., *J. Biol. Chem.,* 271:28009–28016 (1996); Williams et al., *Biochemistry,* 37:7096 (1998); Steadman et al., *Biochemistry,* 37:7089–7095 (1998); Finer-Moore et al., *J. Mol. Biol,* 276:113–129 (1998); Strop et al., *Protein Sci.,* 6:2504–2511 (1997); Finer-Moore et al., *Biochemistry,* 35:5125–5136 (1996); Schiffer et al., *Biochemistry,* 34:16279–16287 (1995); Costi et al., *Biochemistry,* 35:3944–3949 (1996); Graves et al., *Biochemistry,* 31:15–21 (1992); and Carreras et al., *Biochemistry,* 31:6038–6044 (1992)). Such predictions can be made by those of skill in the art of computational chemistry. Hence, for any selected enzyme, the mutations need to inactivate catalytic activity but retain binding activity can be determined empirically.

a. Nucleic Acids Encoding SAH-binding Enzymes

Nucleic acids encoding SAH-binding enzymes can be obtained by methods known in the art. Known nucleic acid sequences of SAH-binding enzymes can be used in isolating nucleic acids encoding SAH-binding enzymes from natural or other sources. Alternatively, complete or partial nucleic acids encoding SAH-binding enzymes can be obtained by chemical synthesis according to the known sequences or obtained from commercial or other sources.

Eukaryotic cells and prokaryotic cells can serve as a nucleic acid source for the isolation of nucleic acids encoding SAH-binding enzymes. The DNA can be obtained by standard procedures known in the art from cloned DNA (e.g., a DNA "library"), chemical synthesis, cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, New York; Glover, D. M. (ed.), 1985, DNA Cloning: A Practical Approach, MRL Press, Ltd., Oxford, U.K. Vol. I, II.). Clones derived from genomic DNA can contain regulatory and intron DNA regions in addition to coding regions; clones derived from cDNA or RNA contain only exon sequences. Whatever the source, the gene is generally molecularly cloned into a suitable vector for propagation of the gene.

In the molecular cloning of the gene from cDNA, cDNA can be generated from totally cellular RNA or mRNA by methods that are known in the art. The gene can also be obtained from genomic DNA, where DNA fragments are generated (e.g., using restriction enzymes or by mechanical shearing), some of which will encode the desired gene. The linear DNA fragments can then be separated according to size by standard techniques, including but not limited to, agarose and polyacrylamide gel electrophoresis and column chromatography.

Once the DNA fragments are generated, identification of the specific DNA fragment containing all or a portion of the SAH-binding enzymes gene can be accomplished in a number of ways.

A preferred method for isolating a SAH-binding enzyme gene is by the polymerase chain reaction (PCR), which can be used to amplify the desired SAH-binding enzyme sequence in a genomic or cDNA library or from genomic DNA or cDNA that has not been incorporated into a library. Oligonucleotide primers which hybridize to the SAH-binding enzyme sequences can be used as primers in PCR.

Additionally, a portion of the SAH-binding enzyme (of any species) gene or its specific RNA, or a fragment thereof, can be purified (or an oligonucleotide synthesized) and labeled, the generated DNA fragments may be screened by nucleic acid hybridization to the labeled probe (Benton and Davis, *Science,* 196:180 (1977); and Grunstein and Hogness, *Proc. Natl. Acad. Sci. U.S.A.,* 72:3961 (1975)). Those DNA fragments with substantial homology to the probe will hybridize. The SAH-binding enzyme nucleic acids can be also identified and isolated by expression cloning using, for example, anti-SAH-binding enzyme antibodies for selection.

Alternatives to obtaining the SAH-binding enzyme DNA by cloning or amplification include, but are not limited to, chemically synthesizing the gene sequence itself from the known SAH-binding enzyme nucleotide sequence or making cDNA to the mRNA which encodes the SAH-binding enzyme. Any suitable method known to those of skill in the art may be employed.

Once a clone has been obtained, its identity can be confirmed by nucleic acid sequencing (by methods known in the art) and comparison to known SAH-binding enzyme sequences. DNA sequence analysis can be performed by techniques known in the art, including but not limited to, the method of Maxam and Gilbert (Maxam and Gilbert, *Meth. Enzymol.*, 65:499–560 (1980)), the Sanger dideoxy method (Sanger et al., *Proc. Natl. Acad. Sci. U.S.A.*, 74:5463 (1977)), the use of T7 DNA polymerase (Tabor and Richardson, U.S. Pat. No. 4,795,699), use of an automated DNA sequenator (e.g., Applied Biosystems, Foster City, Calif.).

Nucleic acids which are hybridizable to a SAH-binding enzyme nucleic acid, or to a nucleic acid encoding a SAH-binding enzyme derivative can be isolated, by nucleic acid hybridization under conditions of low, high, or medium stringency (Shilo and Weinberg, *Proc. Natl. Acad. Sci. USA*, 78:6789–6792 (1981)).

b. Selecting and Producing Mutant SAH-binding Enzymes

Once nucleic acids encoding the SAH-binding enzymes are obtained, these nucleic acids can be mutagenized and screened and/or selected for SAH-binding enzymes that substantially retain their binding affinity or have enhanced binding affinity for SAH but have attenuated catalytic activity. Insertional, deletional or point mutation(s) can be introduced into nucleic acids encoding the SAH-binding enzymes. Techniques for mutagenesis known in the art can be used, including, but not limited to, in vitro site-directed mutagenesis (Hutchinson et al., *J. Biol. Chem.*, 253:6551 (1978)), use of TAB® linkers (Pharmacia), mutation-containing PCR primers, etc. Mutagenesis can be followed by phenotypic testing of the altered gene product.

Site-directed mutagenesis protocols can take advantage of vectors that provide single stranded as well as double stranded DNA, as needed. Generally, the mutagenesis protocol with such vectors is as follows. A mutagenic primer, i.e., a primer complementary to the sequence to be changed, but including one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

Information regrading to the structural-function relationship of the SAH-binding enzymes can be used in the mutagenesis and selection of SAH-binding enzymes that substantially retain their binding affinity or have enhanced binding affinity for SAH but have attenuated catalytic activity. For example, mutants can be made in the enzyme's binding site for its co-enzyme, co-factor, a non-analyte substrate, or in the mutant enzyme's catalytic site, or a combination thereof.

Once a mutant SAH-binding enzyme with desired properties, i.e., substantially retaining its binding affinity or having enhanced binding affinity for SAH but has attenuated catalytic activity, is identified, such mutant SAH-binding enzyme can be produced by any methods known in the art including recombinant expression, chemical synthesis or a combination thereof. Preferably, the mutant SAH-binding enzyme is obtained by recombinant expression.

For recombinant expression, the mutant SAH-binding enzyme gene or portion thereof is inserted into an appropriate cloning vector for expression in a particular host cell. A large number of vector-host systems known in the art may be used. Possible vectors include, but are not limited to, plasmids or modified viruses, but the vector system must be compatible with the host cells used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini. If, however, the complementary restriction sites used to fragment the DNA are not present in the cloning vector, the ends of the DNA molecules can be enzymatically modified. Alternatively, a desired site can be produced by ligating sequences of nucleotides (linkers) onto the DNA termini; these ligated linkers can include specific oligonucleotides encoding restriction endonuclease recognition sequences. Recombinant molecules can be introduced into host cells via transformation, transfection, infection, electroporation, etc., so that many copies of the gene sequence are generated.

In an alternative method, the desired gene can be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated mutant SAH-binding enzyme gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

The nucleotide sequence coding for a mutant SAH-binding enzyme or a functionally active analog or fragment or other derivative thereof, can be inserted into an appropriate expression vector, e.g., a vector which contains the necessary elements for the transcription and translation of the inserted protein-coding sequence. The necessary transcriptional and translational signals can also be supplied by the native mutant SAH-binding enzyme gene and/or its flanking regions. A variety of host-vector systems can be utilized to express the protein-coding sequence. These systems include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, suitable transcription and translation elements can be used.

The methods previously described for the insertion of DNA fragments into a vector can be used to construct expression vectors containing a chimeric gene containing appropriate transcriptional/translational control signals and the protein coding sequences. These methods can include in vitro recombinant DNA and synthetic techniques and in vivo recombinants (genetic recombination). Expression of a nucleic acid sequence encoding a mutant SAH-binding enzyme or peptide fragment can be regulated by a second nucleic acid sequence so that the mutant SAH-binding enzyme or peptide is expressed in a host transformed with the recombinant DNA molecule. For example, expression of a mutant SAH-binding enzyme can be controlled by a promoter/enhancer element as is known in the art. Promoters which can be used to control a mutant SAH-binding enzyme expression include, but are not limited to, the SV40 early promoter region (Bernoist and Chambon, *Nature*, 290:304–310 (1981)), the promoter contained in the 3' long terminal repeat of Rous sarcoma virus (Yamamoto, et al., *Cell*, 22:787–797 (1980)), the herpes thymidine kinase promoter (Wagner et al., *Proc. Natl. Acad. Sci. U.S.A.*, 78:1441–1445 (1981)), the regulatory sequences of the metallothioneine gene (Brinster et al., *Nature*, 296:39–42 (1 982)); prokaryotic expression vectors such as the β-lactamase promoter (Villa-Kamaroff, et al., *Proc. Natl. Acad. Sci. U.S.A.*, 75:3727–3731 (1978)), or the tac promoter (DeBoer, et al., *Proc. Natl. Acad. Sci. U.S.A.*, 80:21–25 (1983)); see also "Useful proteins from recombinant bacteria" in *Scientific American*, 242:74–94 (1980)); promoter elements from yeast or other fungi such as the Gal 4 promoter, the ADC (alcohol dehydrogenase) promoter, PGK (phosphoglycerol kinase) promoter, alkaline phosphatase promoter, and certain animal transcriptional control regions.

For example, a vector can be used that contains a promoter operably linked to a nucleic acid encoding a mutant SAH-binding enzyme, one or more origins of replication, and, optionally, one or more selectable markers (e.g., an antibiotic resistance gene).

In a specific embodiment, an expression construct is made by subcloning a mutant SAH-binding enzyme coding sequence into the EcoRI restriction site of each of the three pGEX vectors (Glutathione S-Transferase expression vectors; see, e.g., Smith and Johnson, *Gene* 7:31–40 (198)). This allows for the expression of a mutant SAH-binding enzyme product from the subclone in the correct reading frame.

Expression vectors containing a mutant SAH-binding enzyme gene inserts can be identified by any method known to those of skill in the art, including the following three general approaches: (a) nucleic acid hybridization, (b) presence or absence of "marker" gene functions, and (c) expression of inserted sequences. In the first approach, the presence of a mutant SAH-binding enzyme gene inserted in an expression vector can be detected by nucleic acid hybridization using probes containing sequences that are homologous to an inserted mutant SAH-binding enzyme gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a mutant SAH-binding enzyme gene in the vector. For example, if the mutant SAH-binding enzyme gene is inserted within the marker gene sequence of the vector, recombinants containing the mutant SAH-binding enzyme insert can be identified by the absence of the marker gene function. In the third approach, recombinant expression vectors can be identified by assaying the mutant SAH-binding enzyme product expressed by the recombinant. Such assays can be based, for example, on the physical or functional properties of the mutant SAH-binding enzyme in in vitro assay systems, e.g., binding with anti-mutant SAH-binding enzyme antibody.

Once a particular recombinant DNA molecule is identified and isolated, several methods known in the art can be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain can be chosen which modulates the expression of the inserted sequences, or modifies and processes the gene product in the specific fashion desired. Expression from certain promoters can be elevated in the presence of certain inducers; thus, expression of the genetically engineered mutant SAH-binding enzyme can be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in appropriate animal cells can be used to ensure "native" glycosylation of a heterologous protein. Furthermore, different vector/host expression systems can effect processing reactions to different extent.

c. Mutant SAH Hydrolase

In a specific embodiment, the mutant SAH-binding enzyme used is a mutant SAH hydrolase, which mutant SAH hydrolase substantially retains its binding affinity or has enhanced binding affinity for SAH but has attenuated catalytic activity. In a preferred embodiment, the attenuated catalytic activity of the mutant SAH is caused by mutation (s) in the mutant SAH hydrolase's binding site for $NAD^+$ or $NADP^+$ or mutation(s) in the mutant SAH hydrolase's catalytic site, or a combination thereof.

Desirably the mutant SAH hydrolase has attenuated 5'-hydrolytic activity but substantially retains its 3'-oxidative activity. For example, the mutant SAH hydrolase can include a sequence of amino acids encoded by the sequence of nucleotides set forth in SEQ ID No. 4 but with one or more mutations selected from Phe 302 to Ser (F302S), Lys 186 to Ala (K186A), His 301 to Asp (H301D), His353 to Ser (H353S), Arg 343 to Ala (R343A), Asp 190 to Ala (D 190A), Phe 82 to Ala (F82A), Thr157 to Leu (T157L), Cys195 to Asp (C195D), Asn181 to Asp (N181D), and deletion of Tyr 432 (Δ432). Another suitable mutant SAH hydrolase includes the sequence of amino acids set forth in SEQ ID No. 4 except that Arg431 is replaced by Ala (R431A) and Lys 426 is replaced by Arg (K426R). It is contemplated that enzymes encoded by nucleic acids that hybridize, particularly under high stringency conditions, to nucleic acid moleucle of SEQ ID No. 4, can be used. Such molecules are tested for the ability to specifically bind to SAH with sufficient affinity to result in detectable complexes from which the amount of SAH can be determined.

Other examples of mutant SAH hydrolases, includ those described in U.S. patent application Ser. No. 09/347,878, filed Jul. 6, 1999, can be used in the above assays. In particular, the nucleic acid molecules containing sequences of nucleotides with the following GenBank accession Nos. can be used to obtaining nucleic acid molecules that encode mutant SAH hydrolases that quantitatively bind to SAH, but do not catalyze hydrolysis thereof: AF129871 (*Gossypium hirsutum*); AQ003753 (*Cryptosporidium parvum*); AF105295 (*Alexandrium fundyense*); AA955402 (*Rattus norvegicus*); AA900229 (*Rattus norvegicus*); AA874914 (*Rattus norvegicus*); AA695679 (*Drosophila melanogaster* ovary); AA803942 (*Drosophila melanogaster* ovary; AI187655 (*Manduca sexta* male antennae); U40872 (*Trichomonas vaginalis*); AJ007835 (*Xenopus Laevis*); AF080546 (*Anopheles gambiae*); AI069796 (*T. cruzi* epimastigote); Z97059 (*Arabidopsis thaliana*); AF059581 (*Arabidopsis thaliana*); U82761 (*Homo sapiens*); AA754430 (*Oryza sativa*); D49804 (*Nicotiana tabacum*); D45204 (*Nicotiana tabacum*); X95636 (*D.melanogaster*); T18277 (endosperm *Zea mays*); R75259 (Mouse brain); Z26881 (*C.roseus*); X12523 (*D. discoideum*); X64391 (*Streptomyces fradiae*); W21772 (Maize Leaf); AH003443 (*Rattus norvegicus*); U14963 (*Rattus norvegicus*); U14962 (*Rattus norvegicus*); U14961 (*Rattus norvegicus*); U14960 (*Rattus norvegicus*); U14959 (*Rattus norvegicus*); U14937 (*Rattus norvegicus*); U14988 (*Rattus norvegicus*); U14987 (*Rattus norvegicus*); U14986 (*Rattus norvegicus*); U14985 (*Rattus norvegicus*); U14984 (*Rattus norvegicus*); U14983 (*Rattus norvegicus*); U14982 (*Rattus norvegicus*); U14981 (*Rattus norvegicus*); U14980 (*Rattus norvegicus*); U14979 (*Rattus norvegicus*); U14978 (*Rattus norvegicus*); U14977 (*Rattus norvegicus*); U14976 (*Rattus norvegicus*); U14975 (*Rattus norvegicus*); L32836 (*Mus musculus*); L35559 (*Xenopus laevis*); Z19779 (Human foetal Adrenals tissue); L23836 (*Rhodobacter capsulatus*); M15185 (Rat); L11872 (*Triticum aestivum*); M19937 (Slime mold (*D.discoideum*); M80630 (*Rhodobacter capsulatus*).

To perform the methods herein in one embodiment, the SAH is contacted with the mutant SAH hydrolase in the presence of a labelled SAH or a derivative or an analog thereof, whereby the amount of the labeled SAH bound to the mutant SAH hydrolase is inversely related to the amount of the SAH produced in the methyltransferase reaction. The activity of the methyltransferase will be proportional to the amount of SAH produced. In a preferred embodiment, the labelled SAH derivative or analog is fluorescenctly labelled.

In another preferred embodiment, the mutant SAH hydrolase is a labelled mutant SAH hydrolase. More preferably, the labelled mutant SAH hydrolase is a fluorescence-labelled mutant SAH hydrolase.

C. METHODS FOR ASSESSING THE ACTIVITY OF METHYLTRANSFERASES AND METHODS OF DIAGNOSIS AND DRUG DISCOVERY BASED THEREON

As described, methods for assessing the activity of methyltransferases, such as SAM-dependent methyltransferases are provided. These methods have particular applicabilty in assays for drug screening in which compounds that alter the activity of the methyltransferases are identified and selected as candidate compounds. These assays may also be used methods for diagnosing disorders in which the activity of a particular methyltransferase can be correlated with a particular disorder or predispostion therefor. These assays may also be used in methods of diagnosis in which the presence of particular methyltransferase substrates associated with a condition (or absence thereof) are identified.

1. Methods for Screening for Compounds that Modulate that Activity of Methyltransferases Provided herein are methods for identifying modulators of a methyltransferase. In practicing these methods, the methyltransferase is contacted with a methyl-donor-dependent methyltransferase with a substrate of the methyltransferase in the presence of the methyl donor under conditions whereby a methyl group is transferred from the donor to the substrate to produce a demethylated donor. The methylated donor is contacted with a mutant binding enzyme that has binding affinity for demethylated donor, but has attenuated or absent catalytic activity. The binding is detected generally by detecting the formation of the complex. Formation of the complex is indicative of methyltransferase activity. The amount of complex formed can be correlated with the amount of methyltransferase in the-reaction that produced the demethylated donor, and thereby the methyltransferase activity. The methyltransferase activity can be assessed by comparing the amount of binding of demethylated donor in the test reaction to a control reaction in which a known amount of the methyltransferase is used, or against a standard curve produced using a variety of known methyltransferase concentrations. The standard curve or other control may be run simultaneously or may be run before or after the test reaction. If necessary or desired, the results may also be normalized by running a control in which there is no enzyme and also a saturating level of enzyme.

For drug and compound screening, the test reaction, preferably is run in the presence and absence of the test compound. If there is a difference between the activity of the methyltransferase in the presence of a test compound and in the absence thereof, the compound is selected as a candidate compund. Typically, a difference is assessed using standard methods for assessing statistically significant differences, including running a plurality of tests for each test compound. Again, these methods are preferably performed in a high throughput format, typically a solid phase format where the mutant binding enzyme is immobilized on a solid support, so that a variety of compounds can be tested simulataneously.

The reactions may be run individually, or, preferrably a plurality of test reactions are run simultaneously. The reactions may be homogeneous, or may be run in a solid state format, such as by linking the mutant binding enzyme (or a plurality thereof, which may be the same or different) to a solid support, such as a silicon or other flat surface appropriately derivatizied. The mutant binding enzymes are produced as described herein and also as described in copending U.S. application Ser. No. 09/347,878 and U.S. application Ser. No. 09/457,205.

As exemplified herein, a preferred methyltransferase is a SAM-dependent methyltransferase and its donor SAM. The resulting demethylated donor is SAH, which can be detected with any of a variety of mutant SAH binding enzymes, described herein and in the above-noted co-pending applications. In particular, SAM-dependent methyltransferase activity is detected by contacting the SAM-dependent methyltransferase with a substrate of the methyltransferase in the presence of SAM and a test substance, whereby a methyl group is transferred from SAM to the substrate and SAM is converted to S-adenosylhomocysteine (SAH), contacting the SAH with a mutant SAH-binding enzyme that has binding affinity for SAH but has attenuated catalytic activity, and detecting binding between SAH and the mutant SAH-binding enzyme to detect or determine the presence or amount of SAH. These results are compared to a control in which a known amount(s) of a SAM-dependent methyltransferase are used. A difference in activity from the activity measured measured in the presence of a test substance or compound indicates that the substance or compound modulates the activity of the SAM-dependent methyltransferase and is a candidate or lead compound.

Provided herein are methods for identifying a modulator of a S-adenosylmethionine (SAM)-dependent methyltransferase, which method comprises: a) contacting the SAM-dependent methyltransferase with a substrate of the methyltransferase in the presence of SAM, whereby a methyl group is transferred from SAM to the substrate and SAM is converted to S-adenosylhomocysteine (SAH), contacting the SAH with a mutant SAH-binding enzyme that has binding affinity for SAH but has attenuated catalytic activity, and detecting binding between SAH and the mutant SAH-binding enzyme to detect or determine the presence or amount of SAH, whereby the activity of the SAM-dependent methyltransferase is assessed; b) contacting the SAM-dependent methyltransferase with a substrate of the methyltransferase in the presence of SAM and a test substance, whereby a methyl group is transferred from SAM to the substrate and SAM is converted to S-adenosylhomocysteine (SAH), contacting the SAH with a mutant SAH-binding enzyme that has binding affinity for SAH but has attenuated catalytic activity, and detecting binding between SAH and the mutant SAH-binding enzyme to detect or determine the presence or amount of SAH, whereby the activity of the SAM-dependent methyltransferase is assessed; and c) comparing the activity of the SAM-dependent methyltransferase assessed in steps a) and b), whereby the activity measured in step a) differs from the activity measured in step b) indicates that the test substance modulates the activity of the SAM-dependent methyltransferase.

In comparing the activity of a SAM-dependent methyltransferase in the presence and absence of a test substance to assess whether the test substance is a modulator of the SAM-dependent methyltransferase, it is unnecessary to assay the activity in parallel, although such parallel measurement is preferred. It is possible to measure the activity of the SAM-dependent methyltransferase at one time point and compare the measured activity to a historical value of the activity of the SAM-dependent methyltransferase. For instance, one can measure the activity of the SAM-dependent methyltransferase in the presence of a test substance and compare with historical value of the activity of the SAM-dependent methyltransferase measured previously in the absence of the test substance, and vice versa. This can be accomplished, for example, by providing the activity of the SAM-dependent methyltransferase on an insert or pamphlet provided with a kit for conducting the assay.

Preferably, the SAM-dependent methyltransferase to be screened against is isolated from a target cell. More preferably, the test substance to be screened for is a therapeutic compound, and whereby a difference of the SAM-dependent methyltransferase measured in the presence and in the absence of the test substance indicates whether the target cell responds to the test substance.

Also provided for herein is a combination for identifying a modulator of the activity of a SAM-dependent methyltransferase, which combination comprises: a) a SAM-dependent methyltransferase; b) a substrate of the methyltransferase to be assayed; c) SAM; d) a mutant SAH-binding enzyme that retains at least substantially its binding affinity for SAH but has attenuated catalytic activity; and e) reagents for detecting binding between SAH and the SAH-binding enzyme. Preferably, the reagent for detecting binding between SAH and the SAH-binding enzyme comprises a labelled SAH, a labelled mutant SAH-binding enzyme, or a derivative or an analog thereof.

Any SAM-dependent methyltransferases, including those described herein, can be used to identify modulators thereof. Any mutant SAH-binding enzyme, which has binding affinity for SAH but has attenuated catalytic activity, including the ones described in U.S. patent application Ser. No. 09/347,878, filed Jul. 6, 1999, can be used in the screening assays. Preferably, the mutant SAH-binding enzyme used is a mutant SAH hydrolase, which mutant SAH hydrolase substantially retains its binding affinity or has enhanced binding affinity for SAH but has attenuated catalytic activity.

Additionally provided herein is a kit comprising the above-described combination. Preferably, the kit further comprises instructions for identifying a modulator of the activity of a SAM-dependent methyltransferase. Typically the kit can include, besides appropriate packaging, including vials and test tubes, compositions containing the the methyltransferase, the mutant binding enzyme that binds to the demethylated donor, such as SAH, optionally controls, such as known compound antagonists, inhibitors or agonists of the methyltransferase.

2. Methods for Screening for Methyltransferase Modulators for Diagnosis

The above-described methods may be adapted for use in methods of diagnosis that can be correlated with methyltransferase activity, methods for identifying or detecting substrantes for a methyltransferase, or any other method or assay in which a methyltransferase activity can be measured and correlated with a particular parameter or component of te systsem.

a. Methods of Diagnosis by Detecting Methyltransferase Activity

Hence, diseases, such as certain cancers, in which increased or altered methylation patterns are observed, (see, e.g., Nosaka et al. (2000) *Cancer Res.* 60:1043–1048; Sanchez-Cespedes et al. (2000) *Cancer Res.* 60:892–895; and Toyata et al. (2000) *Electrophoresis* 21:321–333), aging associated disorders and conditions, such as cardiovascular diseases (see, e.g., Post et al. (1999) *Cadriovasc. Res.* 43:985–991; Fricker (1999) *Cell* 99:247–257) can potentially be diagnosed by correlating a methyltransferase activity and/or level thereof with the presence or absence of a disorder or indicative of a disorder. As discussed herein, levels of methylation of nucleic acids may also be indicative of certain conditions or diseases and such levels can be measured by the methods herein (see, below "Methods for detecting levels of DNA and RNA methylation").

b. Methods of Diagnosis by Detecting and Identifying Substrates and Methods of Identifying Substrates The methods herein may be adapted for detecting the presence and amount of a substrate for a methyltransferase. If such substrate is indicative of a disease, disorder, condition or absence thereof, the methods can be used for such diagnosis. For example, a body fluid or other test sample can be tested by contacting it with a methyltransferase; the amount of demethylated donor is indicative of the presence of the substrate in the sample.

In addition, the methods can be used to identify substrates by testing compounds and looking for production of the demethylated donor.

3. High Throuthput Screening Assays

Although the above-described assay can be conducted using a single SAM-dependent methyltransferase, and/or a single test substance in one assay, the assay preferably is conducted in a high throughput screening mode, i.e., a plurality of the SAM-dependent methyltransferases are screened and/or a plurality of test substances are screened simultaneously (See generally, *High Throughput Screening: The Discovery of Bioactive Substances* (Devlin, Ed.) Marcel Dekker, 1997; Sittampalam et al., *Curr. Opin. Chem. Biol.,* 1(3):384–91 (1997); and Silverman et al., *Curr. Opin. Chem. Biol.,* 2(3):397–403 (1998)). For example, the assay can be conducted in a multi-well (e.g., 24-, 48-, 96-, or 384-well), chip or array format.

High-throughput screening (HTS) is the process of testing a large number of diverse chemical structures against disease targets to identify "hits" (Sittampalam et al., *Curr. Opin. Chem. Biol.,* 1(3):384–91 (1997)). Current state-of-the-art HTS operations are highly automated and computerized to handle sample preparation, assay procedures and the subsequent processing of large volumes of data. Each one of these steps requires careful optimization to operate efficiently and screen 100–300,000 compounds in a 2–6 month period. Hence a modern HTS operation is a multidisciplinary field involving analytical chemistry, biology, biochemistry, synthesis chemistry, molecular biology, automation engineering and computer science (Fernandes, *J. Biomol. Screening,* 2:1 (1997)).

a. HTS Instrumentation and Capabilities

In general, the instrumentation used in HTS assays should be accurate, reliable and easily amenable to automation. Analytical methods should be robust and reproducible, with stable reagents and signal responses. Signal-to-noise (S/N) ratios should be large enough to generate signal windows (Sittampalam et al., *J. Biomol. Screening,* 2:159–169 (1997)) that allow reliable detection of "hits". Equally important are assays with "mix and measure" protocols, which are easier to automate then analytical methods with complex separation steps such as centrifugation, washing and filtration. This is particularly true as the industry moves toward ultra-HTS assays which will screen over 1000,000 compounds per day (Hook, *Drug Discov. Tech.,* 1:287–294 (1996)). Another advantage of "mix and measure" assays is that binding measurements are made under equilibrium conditions (without washing, filtration etc.), and are therefore useful for investigating low affinity interactions (Braunwalder et al., *J. Biomol. Screening,* 1:23–26 (1996)).

b. Detection Technologies

Detection technologies employed in high-throughput screens depend on the type of biochemical pathway being investigated (Sittampalam et al., *Curr. Opin. Chem. Biol.,* 1(3):384–91 (1997)).

1) Radiochemical Methods

Although filtration-based receptor binding assays have been used extensively in the past (to separate the bound and free radiolabeled ligand), the scintillation proximity assay (SPA) has become the standard assay in many HTS operations, mainly because it does not require a separation step, and can be easily automated (Braunwalder et al., *J. Biomol. Screening,* 1:23–26 (1996); Cole, *Methods Enzymol,* 275:310–328 (1996); Cook, *Drug Discov. Tech.,* 1:287–294 (1996); Kahl et al., *J. Biomol. Screening,* 2:33–40 (1997); Lerner et al., *J. Biomol. Screening,* 1:135–143 (1996); Baker et al., *Anal. Biochem.,* 239:20–24 (1996); Baum et al., *Anal. Biochem.,* 237:129–134 (1996); Sullivan et al., *J. Biomol. Screening,* 2:19–23 (1997); De Serres et al., *Ana. Biochem.,* 233:228–233 (1996); Sonatore et al., *Anal. Biochem.,* 240:289–297 (1996); Chen et al., *J. Biol. Chem.,* 271:25308–25315 (1996); Patel et al., *Biochem. Biophys. Res. Commun.,* 221:821–825 (1996); and Fox, *Pharm. Forum,* 6:1–3 (1996)). SPA can also be easily adapted to a variety of enzyme assays (Lerner et al., *J. Biomol. Screening,* 1:135–143 (1996); Baker et al., *Anal Biochem.,* 239:20–24 (1996); Baum et al., *Anal. Biochem.,* 237:129–134 (1996); and Sullivan et al., *J. Biomol. Screening,* 2:19–23 (1997)) and protein-protein interaction assays (Braunwalder et al., *J. Biomol. Screening,* 1:23–26 (1996); Sonatore et al., *Anal. Biochem.,* 240:289–297 (1996); and Chen et al., *J. Biol. Chem.,* 271:25308–25315 (1996)).

One version of SPA utilizes polyvinyltoluene (PVT) microspheres or beads (~5 $\mu$m diameter, density ~1.05 g/cm$^3$) into which a scintillant has been incorporated (Hook, *Drug Discov. Tech.,* 1:287–294 (1996)). When a radiolabeled ligand is captured on the surface of the bead, the radioactive decay occurs in close proximity to the bead, and effectively transfers energy to the scintillant, which results in light emission. When the radiolabel is displaced or inhibited from binding to the bead, it remains free in solution and is too distant from the scintillant for efficient energy transfer. Energy from radioactive decay is dissipated into the solution, which results in no light emission from the beads. Hence the bound and free radiolabel can be detected without the physical separation required in filtration assays.

The ideal isotopes for labeling ligands used in SPA assays are $^3$H and $^{125}$I. This is because the β particles from $^3$H have a relatively short pathlength, about 1.5 $\mu$M, which easily fulfills the distance requirement for SPA. The Auger electrons emitted by $^{125}$I, which travel between approximately 1 $\mu$m and 17.6 $\mu$m in aqueous media, also satisfy this distance requirement.

SPA can also be carried out in scintillating microplates (Braunwalder et al., *J. Biomol. Screening,* 1:23–26 (1996); Fox, *Pharm. Forum,* 6:1–3 (1996); and Harris et al., *Anal. Biochem.,* 243:249–256 (1996)), in which the scintillant is directly incorporated into the plastic, or is coated on the inner surface of the wells. These plates are commercially available. For example, Flashplate® is from NEN™ Life Science Products (Boston, Mass.) in which the scintillant is coated on the inner surface of the wells. The Scinitstrip® plate is from WallacOy (Turku, Finland) which is made by incorporating the scintillant into the entire plastic. A more recent development is the Cytostar-T™ (Amerisham Life Sciences, Cardiff, Wales) scintillating microplates (Fox, *Pharm. Forum,* 6:1–3 (1996) which were specially designed for cell-based proximity assays. Scintillant is incorporated into the base plate of microtiter plates and can also detect additional isotopes such as $^{14}$C, $^{45}$Ca, $^{35}$S, and $^{33}$P.

2) Non-isotopic Detection Methods a) Colorimetry and Luminescence

Colorimetric and luminescence detection methods have significant advantages for HTS laboratories, particularly in light of the cost, safety and disposal issues associates with radiochemical methods. Since luminescence methods can be as sensitive as radioactive methods, with low detection limits, these techniques are being used increasingly in HTS assays (Brown et al., *Curr. Opin. Biotechnol,* 8:45–49 (1997); Glazer, *BioRadiations,* 98:4–8 (1997); Czarnik, *Chem. Biol.,* 2:423–428 (1995); Wang et al., *Tetrahedron Lett.,* 31:6493–6496 (1991); Mathis, *Clin. Chem.,* 41:1391–1397 (1995); Kolb et al., *J. Biomol. Screening,* 1:203–210 (1996); Gonzalez et al., *Biophys. J.,* 69:1272–1280 (1995); Schroeder et al., *J. Biomol. Screening,* 1:75–80 (1996); Waggoner et al., *Hum. Pathol,* 27:494–502 (1996); Jameson et al., *Methods Enzymol.,* 246:283–300 (1995); Lundblad et al., *Mol. Endocrinol.,* 10:607–612 (1996); Checovich et al., *Nature,* 375:254–256 (1995); Levine et al., *Anal. Biochem.,* 247:83–88 (1997); Jolley, *J. Biomol. Screening,* 1:33–38 (1996); Schade et al., *Anal. Biochem.,* 243:1–7 (1996); Lynch et al., *Anal. Biochem.,* 247:77–82 (1997); Sterrer et al., *J. Recept. Signal*

Transduct Res., 17:511–520 (1997); Rigler, *J. Biotechnol.*, 41:177–186 (1995); Rauer et al., *Biophys. Chem.*, 58:3–12 (1996); Sarubbi et al., *Anal. Biochem.*, 237:70–75 (1996); Rose et al., *Network Science*, 2(9):1–12 (1996); Dhundale et al., *J. Biomol. Screening*, 1:115–118 (1996); Suto et al., *J. Biomol. Screening*, 2:7–9 (1997); Bronstein et al., *Anal. Biochem.*, 219:169–181 (1994); Hastings, *Gene*, 173:5–11 (1996); Lehel et al., *Anal. Biochem.*, 244:340–346 (1997); Kolb et al., *J. Biomol. Screening*, 1:85–88 (1996); Bran et al., *J. Biomol. Screening*, 1:43–45 (1996); Rizzuto et al., *Curr. Biol.*, 6:183–188 (1996)). Glazer (Glazer, *BioRadiations*, 98:4–8 (1997)) and Czarnik (Czarnik, *Chem. Biol*, 2:423–428 (1995)) and the Fluorescent Chemosensors and Biosensors Database on the World Wide Web URL; http://biomednet.com/fluoro/have reviewed the utility and need for fluorescence-based techniques for biological applications, which can be easily extended to HTS assays.

b) Resonance Energy Transfer

Resonance energy transfer (RET) between a fluorophore and chromophore was one of the earliest methods developed for HTS. For example, a peptide substrate for an HIV protease was synthesized with EDANS (as the amino terminus) as the donor fluorophore, and DABCYL (at the carboxyl terminus) as the acceptor chromophore (Wang et al., *Tetrahedron Lett.*, 31:6493–6496 (1991)). Energy transfer from EDANS to DABCYL in the intact peptide resulted in quenching of EDANS fluorescence.

c) Time-resolved Fluorescence

A new homogeneous time-resolved fluorescence (HTRF) technology has been described (Mathis, *Clin. Chem.*, 41:1391–1397 (1995)). The assay utilizes fluorescence energy transfer between two fluorophores (an europium cryptate and a 105 kDa phycobiliprotein, allophycocyanin) as labels. The Eu-trisbipyridine cryptate (TBP-EU$^{3+}$, $\lambda_{ex}$= 337 nm) has two bipyridyl groups that harvest light and channel it to the caged Eu$^{3+}$. It has a long fluorescence, lifetime and nonradiatively transfers the energy to allophycocyanin when the two labels are in close proximity (>50% transfer efficiency at a donor-acceptor distance of 9.5 nm). The resulting fluorescence of allophycocyanin $\lambda_{em}$=665 nm) retains the long lifetime of the donor TBP)-EU$^{3+}$, allowing time-resolved measurement. These labels and their spectroscopic characteristics are very stable in biological media.

d) Cell-based Fluorescence Assays

An interesting fluorescence resonance energy transfer (FRET) procedure for sensing voltage across cell membranes has been described recently (Gonzalez et al., *Biophys. J.*, 69:1272–1280 (1995)). The technique uses membrane permeable, anionic oxonols which rapidly locate on the inner or outer membrane surface depending on polarization state of the membrane. FRET occurs between fluorescein-labeled WGA and the oxonols bound to the other surface of the membrane at a resting negative potential. As a positive potential, the oxonols are relocated to the inner membrane surface, and the FRET is greatly reduced.

Many fluorescence intensity measurements, including FRET, can be easily configured on a new instrument specifically designed for cell-based HTS assays in 96-well plates called FLIPr (Schroeder et al., *J. Biomol. Screening*, 1:75–80 (1996)). FLIPR utilizes a water-cooled argon ion laser (5 watt) or a xenon arc lamp and a semiconfocal optical system with a charge-coupled device (CCD) camera to illuminate and image the entire plate. The spatial resolution of the optics is ~200 μm at the cell plane. The plate chamber temperature can be controlled precisely, and a 96-well pipettor head is integrated into the instrument. These features allow accurate measurements of cellular biochemistry in confluent layers of cells at the bottom of plates. FLIPR software can rapidly quantify transient fluorescence signals in intact cells that are growing attached to the bottom of the well. HTS assays involving intracellular calcium, pH and membrane potential measurements have been designed using this instrument (Waggoner et al., *Hum. Pathol.*, 27:494–502 (1996)).

e) Fluorescence Polarization

Another technique that has gained popularity recently is fluorescence polarization or anisotropy (Jameson et al., *Methods Enzymol.*, 246:283–300 (1995); Lundblad et al., *Mol. Endocrinol.*, 10:607–612 (1996); Checovich et al., *Nature*, 375:254–256 (1995); Levine et al., *Anal. Biochem.*, 247:83–88 (1997); Jolley, *J. Biomol. Screening*, 1:33–38 (1996); Schade et al., *Anal. Biochem.*, 243:1–7 (1996); and Lynch et al., *Anal. Biochem.*, 247:77–82 (1997)). When fluorescently labeled molecules in solution are illuminated with plane-polarized light, the emitted fluorescence will be in the same plane provided the molecules remain stationary. Since all molecules tumble as a result of collisional motion, depolarization phenomenon is proportional to the rotational relaxation time ($\mu$) of the molecule, which is defined by the expression 3 ηV/RT. At constant viscosity (η) and temperature (T) of the solution, polarization is directly proportional to the molecular volume (V) (R is the universal gas constant). Hence changes in molecular volume or molecular weight due to binding interactions can be detected as a change in polarization. For example, the binding of a fluorescently labeled ligand to its receptor will result in significant changes in measured fluorescence polarization values for the ligand. Once again, the measurements can be made in a "mix and measure" mode without physical separation of the bound and free ligands. The polarization measurements are relatively insensitive to fluctuations in fluorescence intensity when working in solutions with moderate optical intensity.

f) Fluorescence Correlation Spectroscopy

Fluorescence correlation spectroscopy (FCS) has been recently described for HTS applications (Sterrer et al., *J. Recept. Signal Transduct Res.*, 17:511–520 (1997); Rigler, *J. Biotechnol.*, 41:177–186 (1995); and Rauer et al., *Biophys. Chem.*, 58:3–12 (1996)). FCS measures time-dependent and spontaneous fluctuations in fluorescence intensities in very small volumes (nanoliters). These fluctuations usually result from Brownian motion associated with chemical reactions, diffusion or the flow of fluorescently labeled molecules. The average fluctuation is proportional to the square foot of N, where N is the average number of molecules in the volume. Since Brownian diffusion is directly affected by molecular interactions, FCS is an excellent tool to measure binding interactions (Brown et al., *Curr. Opin. Biotechnol*, 8:45–49 (1997)). Using powerful lasers and autocorrelation techniques, sensitive measurements (at concentrations of ~$10^{-12}$M) can be made in solution and in cellular compartments.

c. Miniaturization

Several factors are fueling efforts to increase the speed of HTS and decrease the volume of individual reactions within an HTS format (Silverman et al., *Curr. Opin. Chem. Biol.*, 2(3):397–403 (1998)). Split-bead synthesis, or other similar approaches to combinatorial chemistry, dramatically increases the number of compounds that can be produced in a library but do so at the cost of quantity of material.

One approach involves reducing the well size and increasing the density of the assay plate but retaining the overall assay format used in current 96-well based HTS. Densities of 6,500 assays in a 10 cm array have been reported to cell-free enzyme based assays (Schullek et al., *Anal. Biochem.*, 246:20–29 (1997)) and for ligand binding in cell based assays (You et al., *Chem. Biol*, 4:969–975 (1997)). This approach of miniaturizing existing formats significantly increases the number of assays per plate and the overall throughput of the screen but is intrinsically limited by the physical constraints of delivering small volumes to wells, and of detecting responses in a sensitive and timely manner.

Another approach uses glass chips containing microchannels in which reagents, target proteins and compounds are herded by electrokinetic flow controlled by electric potentials applied at the ends of the channels (Hadd et al., *Anal. Chem.*, 69:3407–3412 (1997)). A related approach attains the high-throughput of chemical synthesis and activity assessment by parallel arrays of three-dimensional channels in which flow is controlled by miniature hydrostatic actuators (Rogers, *Drug Discov. Today*, 2:306 (1997)). These approaches provide significant reduction in the volume of assays and a corresponding savings in reagent costs over conventional HTS. In addition, with further development in parallel processing in multiple chips, the number of assays performed in a given period of time can increase dramatically.

HTS methods are well known, and any such method, with or without modification for use in the methods herein, can be used in the screening assays provided herein to identify modulators of methyltransferases, particularly SAM-dependent methyltransferases (Janzen et al., The 384-well plate: pros and cons, *J. Biomol. Screening*, 1:63–64 (1996); Lutz, et al., Experimental design for high-throughput screening, *Drug Discov. Tech.*, 1:277–286 (1996); Klein, et al., Recombinant microorganisms as tools for high throughput screening for non antibiotic compounds, *J. Biomol. Screening*, 2:41–49 (1997); Webb, et al., Transcription-specific assay for quantifying mRNA: A potential replacement for reporter gene assays, *J. Biomol. Screening*, 1:119–121 (1996); Charych, et al., Direct colorimetric detection of receptor-ligand interaction by a polymerized bilayer assembly, *Science*, 261:585–588 (1993); Charych, et al., A 'litmus test' for molecular recognition using artificial membranes, *Chem. Biol*, 3:113–120 (1996); Spevak, et al., Carbohydrates in an acidic multivalent assembly: nanomolar P-selectin inhibitors, *J. Med. Chem.*, 38:1018–1020 (1996); Allen, et al., Atomic force microscopy in analytical biotechnology, *Trends Biotechnol.*, 15:101–105 (1997); Troy, et al., Scanning force microscopy helps in the design of cancer drugs, *Biophoton Int.*, 9/10:52–53 (1996); Paborsky, et al., A nickel chelate microtiter plate assay for six histidine-containing proteins, *Anal. Biochem.*, 234:60–65 (1996); Weiss-Wichert, et al., A new analytical device based on gated ion channels: A peptide channel biosensor, *J. Biomol. Screening*, 2:11–18 (1997); Brecht, et al., Transducer-based approaches for parallel binding assays in HTS, *J. Biomol. Screening*, 1:191–201 (1996); Tyagi, et al., Molecular beacons: probes that fluoresce upon hybridization, *Nat. Biotechnol.*, 14:303–308 (1996); Heller, et al., Discovery and analysis of inflammatory disease-related genes using cDNA microarrays, *Proc. Natl. Acad. Sci. USA*, 94:2150–2155 (1997); Nicolaou, et al., Radiofrequency encoded combinatorial chemistry, *Angew Chem. Int. Ed.*, 34:2289–2291 (1995); Fitzgerald, et. al., Direct characterization of solid phase resin-bound molecules by mass spectrometry, *Bioorg. Med. Chem. Lett.*, 6:979–982 (1996); Chu, et al., Affinity capillary electrophoresis-mass spectrometry for screening combinatorial libraries, *J. Am. Chem. Soc.*, 118:7827–7835 (1996); and Evans, et al., Affinity-based screening of combinatorial libraries using automated, serial-column chromatography, *Nat. Biotechnol.*, 14:504–507 (1996)).

4. Test Substances

Any test substance can be tested in the above methods for identification of compounds and methyltransferase substrates. Sources of such substances, include, but are not limited to, combinatorial libraries. Such libraries can be screened, for example, to identify compounds that moduluate, i.e., agonize or antagonize, that activity of a SAM-dependent methyltransferase.

a. Combinatorial Libraries

Methods for synthesizing combinatorial libraries and characteristics of such combinatorial libraries are known in the art (See generally, *Combinatorial Libraries: Synthesis, Screening and Application Potential* (Cortese Ed.) Walter de Gruyter, Inc., 1995; Tietze and Lieb, *Curr. Opin. Chem. Biol.*, 2(3):363–71 (1998); Lam, *Anticancer Drug Des.*, 12(3):145–67 (1997); Blaney and Martin, *Curr. Opin. Chem. Biol.*, 1(1):54–9 (1997); and Schultz and Schultz, *Biotechnol. Prog.*, 12(6):729–43 (1996)).

Methods and strategies for generating diverse libraries, primarily peptide- and nucleotide-based oligomer libraries, have been developed using molecular biology methods and/or simultaneous chemical synthesis methodologies (see, e.g., Dower et al., *Annu. Rep. Med. Chem.*, 26:271–280 (1991); Fodor et al., *Science*, 251:767–773 (1991); Jung et al., *Angew. Chem. Ind. Ed. Engl.*, 31:367–383 (1992); Zuckerman et al., *Proc. Natl. Acad. Sci. USA*, 89:4505–4509 (1992); Scott et al., *Science*, 249:386–390 (1990); Devlin et al., *Science*, 249:404–406 (1990); Cwirla et al., *Proc. Natl. Acad. Sci. USA*, 87:6378–6382 (1990); and Gallop et al., *J. Medicinal Chemistry*, 37:1233–1251 (1994)). The resulting combinatorial libraries potentially contain millions of compounds and that can be screened to identify compounds that exhibit a selected activity.

The libraries fall into roughly three categories: fusion-protein-displayed peptide libraries in which random peptides or proteins are presented on the surface of phage particles or proteins expressed from plasmids; support-bound synthetic chemical libraries in which individual compounds or mixtures of compounds are presented on insoluble matrices, such as resin beads (see, e.g., Lam et al., *Nature*, 354:82–84 (1991)) and cotton supports (see, e.g., Eichler et al., *Biochemistry* 32:11035–11041 (1993)); and methods in which the compounds are used in solution (see, e.g., Houghten et al., *Nature*, 354:84–86 (1991); Houghten et al., *BioTechniques*, 313:412–421 (1992); and Scott et al., *Curr. Opin. Biotechnol*, 5:40–48 (1994)). There are numerous examples of synthetic peptide and oligonucleotide combinatorial libraries. The present direction in this area is to produce combinatorial libraries that contain non-peptidic small organic molecules. Such libraries are based on either a basis set of monomers that can be combined to form mixtures of diverse organic molecules or that can be combined to form a library based upon a selected pharmacophore monomer.

Either a random or a deterministic combinatorial library can be screened by the presently disclosed and/or claimed screening methods. In either of these two libraries, each unit of the library is isolated and/or immobilized on a solid support. In the deterministic library, one knows a priori a particular unit's location on each solid support. In a random library, the location of a particular unit is not known a priori although each site still contains a single unique unit.

For example, a combinatorial library with deterministic sequences, such as the library generated by the multipin technique originated by Geysen et al., *Proc. Natl. Acad. Sci. USA*, 81:3998–4002 (1984), the library generated by the tea bag technique originated by Houghten et al., *Proc. Natl. Acad. Sci. USA*, 81:5131–5135 (1985) and the library generated by the microchip fabrication technique, is screened. In other emodiments, a random combinatorial library is screened such as, a random peptide library such as a library of active sites of proteins or a random polynucleotides.

Sources of combinatorial libraries and methods for generating them include those set forth in Table 3 (see, Schultz et al. *Biotechnol. Prog.*, 12(6):729–43 (1996)).

TABLE 3

Combinatorial Library Technologies

| Co. | technology |
|---|---|
| ABI/Perkin Elmer (Norwalk, CT) | micromachining |
| Affymax Corp. (Santa Clara, CA) | photolithographic combinatorial chemistry |
| Ariad Pharmaceutical (Cambridge, MA) | |
| Cambridge Antibody Technologies (Cambridge, England) | phage system for antibodies |
| Chiron (Emeryville, CA) | multipin chemistry, Mimotopes-robotic synthesizers |
| CuraGen Corp. (Branford, CT) | modularization of DNA, analysis steps, micromachining, microfluidics, PCR |
| Combion, Inc. (Redwood City, CA) | in situ synthesis, Chem-Jet (ink-jet method) |
| David Sarnoff Research Center (Princeton, NJ) | array hybridization (MicroLab) |
| GeneTrace, Inc. (Menlow Park, CA) | time-of-flight mass spectroscopy reads array of 1000 cells/in.$^2$ |
| Genosensor Consortium (The Woodlands, TX) | CCD cameras, flow through devices |
| Gilead Sciences, Inc. (Foster City, CA) | aptamers |
| Houghten Pharmaceuticals, Inc. (San Diego, CA) | tea bag technique, rapid identification of peptide leads |
| Hyseq, Inc. (Sunnyvale, CA) | format 3 methods, array-of-arrays, statistical analysis |
| ISIS Pharmaceuticals, Inc. (Carlsbad, CA) | |
| Molecular Tool, Inc. (Baltimore, MD) | micromachining, microfluidics, microcapillary, electrophoresis, gene bit analysis |
| Nanogen (San Diego, CA) | individually controlled electrophoretic gradients on a chip |
| NeXagen, Inc. (Boulder, CO) | SELEX (Systematic evolution of ligands by exponential enrichment) |
| Perceptive Biosystems (Farmington, MA) | solubilized targets to more closely mimics in vivo conditions |
| Pharmacopeia, Inc. (Princeton, NJ) | tags from arylethers that can be distinguished by gas chromatography; up to 10 different compounds can be identified by 40 tags |
| 3-Dimensional Pharmaceuticals | directed diversity (R) process |
| Vysis (Naperville, IL) | genosensor-based, comparative genome hybridization (CHG) |

Other combinatorial libraries can be used in the screening for a modulator of a SAM-dependent methyltransferase (for such libraries, see, e.g., Bartel, et al., Isolation of New Ribozymes from a Large Pool of Random Sequences, *Science*, 261:1411–1418 (1993); Baumbach, et al., Protein Purification Using Affinity Ligands Deduced from Peptide Libraries, *BioPharm*, (May):24–35 (1992); Bock, et al., Selection of Single-Stranded DNA Molecules That Bind and Inhibit Human Thrombin, *Nature*, 355:564–566 (1992); Borman, S., Combinatorial chemists focus on samll molecules molecular recognition, and automation, *Chem. Eng. News*, 2(12):29 (1996); Boublik, et al., Eukaryotic Virus Display: Engineering the Major Surface Glycoproteins of the Autographa California Nuclear Polyhedrosis Virus (ACNPV) for the Presentation of Foreign Proteins on the Virus Surface, *Bio/Technology*, 13:1079–1084 (1995); Brenner, et al., Encoded Combinatorial Chemistry, *Proc. Natl. Acad Sci. U.S.A.*, 89:5381–5383 (1992); Caflisch, et al., Computational Combinatorial Chemistry for De Novo Ligand Design: Review and Assessment, *Perspect. Drug Discovery Des.*, 3:51–84 (1995); Cheng, et al., Sequence-Selective Peptide Binding with a Peptido-A,B-trans-steroidal Receptor Selected from an Encoded Combinatorial Library; *J. Am. Chem. Soc.*, 118:1813–1814 (1996); Chu, et al., Affinity Capillary Electrophoresis to Identify the Peptide in A Peptide Library that Binds Most Tightly to Vancomycin, *J. Org. Chem.*, 58:648–652 (1993); Clackson, et al., Making Antibody Fragments Using Phage Display Libraries, *Nature*, 352:624–628 (1991); Combs, et al., Protein Structure-Based Combinatorial Chemistry: Discovery of Non-Peptide Binding Elements to Src SH3 Domain, *J. Am. Chem. Soc.*, 118:287–288 (1996); Cwirla, et al., Peptides On Phage: A Vast Library of Peptides for Identifying Ligands, *Proc. Natl. Acad. Sci. U.S.A.*, 87:6378–6382 (1990); Ecker, et al., Combinatorial Drug Discovery: Which Method will Produce the Greatest Value?, *Bio/Technology*, 13:351–360 (1995); Ellington, et al., In Vitro Selection of RNA Molecules That Bind Specific Ligands, *Nature*, 346:818–822 (1990); Ellman, J. A., Variants of Benzodiazephines, *J. Am. Chem. Soc.*, 114:10997 (1992); Erickson, et al., The Proteins; Neurath, H., Hill, R. L., Eds.: Academic: New York, 1976; pp. 255–257; Felici, et al., *J. Mol. Biol.*, 222:301–310 (1991); Fodor, et al., Light-Directed, Spatially Addressable Parallel Chemical Synthesis, *Science*, 251:767–773 (1991); Francisco, et al., Transport and Anchoring of Beta-Lactamase to the External Surface of E. Coli., *Proc. Natl. Acad. Sci. U.S.A.*, 89:2713–2717 (1992); Georgiou, et al., Practical Applications of Engineering Gram-Negative Bacterial Cell Surfaces, *TIBTECH*, 11:6–10 (1993); Geysen, et al., Use of peptide synthesis to probe viral antigens for epitopes to a resolution of a single amino acid, *Proc. Natl. Acad. Sci. U.S.A.*, 81:3998–4002 (1984); Glaser, et al., Antibody Engineering by Condon-Based Mutagenesis in a Filamentous Phage Vector System, *J. Immunol.*, 149:3903–3913 (1992); Gram, et al., In vitro selection and affinity maturation of antibodies from a naive combinatorial immunoglobulin library, *Proc. Natl. Acad. Sci.*, 89:3576–3580 (1992); Han, et al., Liquid- Phase Combinatorial Synthesis, *Proc. Natl. Acad. Sci. U.S.A.*, 92:6419–6423 (1995); Hoogenboom, et al., Multi-Subunit Proteins on the Surface of Filamentous Phage: Methodologies for Displaying-Antibody (Fab) Heavy and Light Chains, *Nucleic Acids Res.*, 19:4133–4137 (1991); Houghten, et al., General Method for the Rapid Solid-Phase Synthesis of Large Numbers of Peptides: Specificity of Antigen-Antibody Interaction at the Level of Individual Amino Acids, *Proc. Natl. Acad. Sci. U.S.A.*, 82:5131–5135 (1985); Houghten, et al., The Use of Synthetic Peptide Combinatorial Libraries for the Determination of Peptide Ligands in Radio-Receptor Assays—Opiod-Peptides, *Bioorg. Med. Chem. Lett.*, 3:405–412 (1993); Houghten, et al., Generation and Use of Synthetic Peptide Combinatorial Libraries for Basic Research and Drug Discovery, *Nature*, 354:84–86 (1991); Huang, et al., Discovery of New Ligand Binding Pathways in Myoglobin by Random Mutagenesis, *Nature Struct. Biol.*, 1:226–229 (1994); Huse, et al., Generation of a Large Combinatorial Library of the Immunoglobulin Repertoire In Phage Lambda, *Science*, 246:1275–1281 (1989); Janda, K. D., New Strategies for the Design of Catalytic Antibodies, *Biotechnol. Prog.*, 6:178–181 (1990); Jung, et al., Multiple Peptide Synthesis Methods and Their Applications, Angew. Chem. Int. Ed. Engl., 31:367–486 (1992); Kang, et al., Linkage of Recognition and Replication Functions By Assembling Combinatorial Antibody Fab Libraries Along Phage Surfaces, Proc. Natl. Acad. Sci. U.S.A., 88:4363–4366 (1991a); Kang, et al., Antibody Redesign by Chain Shuffling from Random Combinatorial Immunoglobulin Libraries, Proc. Natl. Acad. Sci. U.S.A., 88:11120–11123 (1991b); Kay, et al., An M13 Phage Library Displaying Random 38-Amino-Acid-Peptides as a Source of Novel Sequences with Affinity to Selected Targets Genes, Gene, 128:59–65 (1993); Lam, et al., A new type of synthetic peptide library for identifying ligand-binding activity, Nature, 354:82–84 (1991) (published errata apear in Nature, 358:434 (1992) and Nature, 360:768 (1992); Lebl, et al., One Bead One Structure Combinatorial Libraries, Biopolymers (Pept. Sci., 37:177–198 (1995); Lerner, et al., Antibodies without Immunization, Science, 258:1313–1314 (1992); Li, et al., Minimization of a Polypeptide Hormone, Science, 270:1657–1660 (1995); Light, et al., Display of Dimeric Bacterial Alkaline Phosphatase on the Major Coat Protein of Filamentous Bacteriophage, Bioorg. Med. Chem. Lett., 3:1073–1079 (1992); Little, et al., Bacterial Surface Presentation of Proteins and Peptides: An Alternative to Phage Technology?, Trends Biotechnol., 11:3–5 (1993); Marks, et al., By-Passing Immunization. Human Antibodies from V-Gene Libraries Displayed on Phage, J. Mol. Biol., 222:581–597 (1991); Matthews, et al., Substrate Phage: Selection of Protease Substrates by Monovalent Phage Display, Science, 260:1113–1117 (1993); McCafferty, et al., Phage Enzymes: Expression and Affinity Chromatography of Functional Alkaline Phosphatase on the Surface of Bacteriophage, Protein Eng., 4:955–961 (1991); Menger, et al., Phosphatase Catalysis Developed Via Combinatorial Organic Chemistry, J. Org. Chem., 60:6666–6667 (1995); Nicolaou, et al., Angew. Chem. Int. Ed. Engl., 34:2289–2291 (1995); Oldenburg, et al., Peptide Ligands for A Sugar-Binding Protein Isolated from a Random Peptide Library, Proc. Natl. Acad. Sci. U.S.A., 89:5393–5397 (1992); Parmley, et al., Antibody-Selectable Filamentous fd Phage Vectors: Affinity Purification of Target Genes, Genes, 73:305–318 (1988); Pinilla, et al., Synthetic Peptide Combinatorial Libraries (SPCLS)—Identification of the Antigenic Determinant of Beta-Endorphin Recognized by Monoclonal Antibody-3E7, Gene, 128:71–76 (1993); Pinilla, et al., Review of the Utility of Soluble Combinatorial Libraries, Biopolymers, 37:221–240 (1995); Pistor, et al., Expression of Viral Hemegglutinan On the Surface of E. Coli., Klin. Wochenschr., 66:110–116 (1989); Pollack, et al., Selective Chemical Catalysis by an Antibody, Science, 234:1570–1572 (1986); Rigler, et al., Fluorescence Correlations, Single Molecule Detection and Large Number Screening: Applications in Biotechnology, J. Biotechnol., 41:177–186 (1995); Sarvetnick, et al., Increasing the Chemical Potential of the Germ- Line Antibody Repertoire, Proc. Natl. Acad. Sci. U.S.A., 90:4008–4011 (1993); Sastry, et al., Cloning of the Immunological Repertiore in Escherichia Coli for Generation of Monoclonal Catalytic Antibodies: Construction of a Heavy Chain Variable Region-Specific cDNA Library, Proc. Natl. Acad. Sci. U.S.A., 86:5728–5732 (1989); Scott, et al., Searching for Peptide Ligands with an Epitope Library, Science, 249:386–390 (1990); Sears, et al., Engineering Enzymes for Bioorganic Synthesis: Peptide Bond Formation, Biotechnol. Prog., 12:423–433 (1996); Simon, et. al., Peptides: A Modular Approach to Drug Discovery, Proc. Natl. Acad. Sci. U.S.A., 89:9367–9371 (1992); Still, et al., Discovery of Sequence-Selective Peptide Binding by Synthetic Receptors Using Encoded Combinatorial Libraries, Acc. Chem. Res., 29:155–163 (1996); Thompson, et al., Synthesis and Applications of Small Molecule Libraries, Chem. Rev., 96:555–600 (1996); Tramontano, et al., Catalytic Antibodies, Science, 234:1566–1570 (1986); Wrighton, et al., Small Peptides as Potent Mimetics of the Protein Hormone Erythropoietin, Science, 273:458–464 (1996); York, et al., Combinatorial mutagenesis of the reactive site region in plasminogen activator inhibitor I, J. Biol. Chem., 266:8595–8600 (1991); Zebedee, et al., Human Combinatorial Antibody Libraries to Hepatitis B Surface Antigen, Proc. Natl. Acad. Sci. U.S.A., 89:3175–3179 (1992); Zuckerman, et al., Identification of Highest-Affinity Ligands by Affinity Selection from Equimolar Peptide Mistures Generated by Robotic Synthesis, Proc. Natl. Acad. Sci. U.S.A., 89:4505–4509 (1992)).

5. Methods for Detecting Levels of DNA and RNA Methylation

DNA methylation is among the mechanisms for regulating gene expression. DNA methylation is associated with DNA mismatch repair, DNA stability and structure and gene transcription. RNA methylation is related to RNA stability, splicing and translation. Hypermethylation and hypomethylation of nucleic acids are known to be causative or related to a variety of diseases, including cancer, neurodegenerative diseases and arteriosclerosis. For example, DNA hypomethylation is increased in breast carcinomas, and potentially plays a role in tumor development. Global DNA methylation status is a biological marker for certain neoplasms. CpG hypermethylation is associated with gene silencing in cancer. This epigenetic event is genetically accepted as a stochastic process in tumor cells resulting from aberrant DNA methyltransferase activities. Therefore measurement of global and also specific or local patters of DNA or RNA methylation is of clinical diagnostic use.

Determination of DNA and RNA methylation has heretofore proven cumbersome. Available methods include radioimmunoassays and HPLC-based assays that require use of either radioactive labels or HPLC after hydrolysis. These assays are complicated, require multiple steps and have low throughput.

The methods for assessing methylase activity provided herein can be used to determine levels of DNA and RNA methylation. This can be achieved, for example, by isolating nucleic acid using sequence-specific probes. The nucleic acid can be randomly or specifically fragmented, such as by restriction endonuclease digestion (complete or partial). The isolated nucleic acid can be incubated with a methyltransferase, such as nucleotide base transferase, including one or more of O-6-methylguanine DNA methyltransferase, (cytosine-5-)DNA methyltransferase and adenine-N6 DNA methyltransferase, to methylate unmethylated positions in the nucleic acid in the presence of a methyl donor, such as SAM, to produce the demethylated donor, such as SAH. The demethylated donor is quantitated as described herein. The amount of the demethylated donor is stoichiometrically correlated with the amount of transferred methyl groups, which is related to the amount of unmethylated positions on the nucleic acid sample. The amounts determined can be compared to controls, such as nucleic acid obtained from healthy donors (i.e. individuals not afflicted with the disease being diagnosed) or with previously determined standards, or with a standard curve. These assays can be automated by performing a plurality of such reactions simultaneously, preferably in a multiwell format or array format containing, typically at least 96 samples or higher multiples thereof.

D. LABELLING OF MUTANT SAH-BINDING ENZYMES

Conjugates, such as fusion proteins and chemical conjugates, of the mutant SAH-binding enzyme with a protein or peptide fragment (or plurality thereof) that functions, for example, to facilitate affinity isolation or purification of the mutant enzyme, attachment of the mutant enzyme to a surface, or detection of the mutant enzyme are provided. The conjugates can be produced by chemical conjugation, such as via thiol linkages, but are preferably produced by recombinant means as fusion proteins. In the fusion protein, the peptide or fragment thereof is linked to either the N-terminus or C-terminus of the mutant enzyme. In chemical conjugates the peptide or fragment thereof may be linked anywhere that conjugation can be effected, and there may be a plurality of such peptides or fragments linked to a single mutant enzyme or to a plurality thereof.

1. Conjugation

Conjugation can be effected by any method known to those of skill in the art. As described below, conjugation can be effected by chemical means, through covalent, ionic or any other suitable linkage.

a. Fusion Proteins

Fusion proteins are proved herein. A fusion protein contains: a) one or a plurality of mutant SAH-binding enzymes and b) at least one protein or peptide fragment that facilitates, for example: i) affinity isolation or purification of the fusion protein; ii) attachment of the fusion protein to a surface; iii) detection of the fusion protein; or iv) targeted delivery of the conjugate to a selected tissue or cell, or any combination thereof.

The facilitating agent is selected to perform the desired purpose, such as (i)–(iv), and is linked a mutant SAH-binding enzyme such that the resulting conjugate retains the mutant SAH-binding enzyme property and also processes the property(ies) of the facilitating agent. For example, the facilitating agent can be protein or peptide fragment, such as a protein binding peptide, including but not limited to an epitope tag or an IgG binding protein, a nucleotide binding proteins, such as a DNA or RNA binding protein, a lipid binding protein, a polysaccharide binding protein, and a metal binding protein or fragments thereof that possess the requisite desired facilitating activity.

Such facilitating agents can be designed, screened or selected according to the methods known in the art. The screening or selection process begin, for example, with nucleic acid encoding a particular protein or peptide to be used in the fusion protein, and screened or selected for its specific binding partner. Alternatively, the screening or selection process can start with a specific molecule that can be used in the subsequent isolation/purification, attachment or detection, and screen or select for a particular protein or peptide sequence to be used in the fusion protein that can specifically bind to the pre-selected molecule.

The conventional technique of random screening of natural products can be used in screening and selecting a protein or peptide sequence and its specific binding partner. In addition, numerous strategies can be used for preparing proteins having new binding specificities. These new approaches generally involve the synthetic production of large numbers of random molecules followed by some selection procedure to identify the molecule of interest. For example, epitope libraries have been developed using random polypeptides displayed on the surface of filamentous phage particles. The library is made by synthesizing a repertoire of random oligonucleotides to generate all combinations, followed by their insertion into a phage vector. Each of the sequences is separately cloned and expressed in phage, and the relevant expressed peptide can be selected by finding those phage that bind to the particular target. The phages recovered in this way can be amplified and the selection repeated. The sequence of the peptide is decoded by sequencing the DNA (See e.g., Cwirla et al., *Proc. Natl. Acad. Sci., USA,* 87:6378–6382 (1990); Scott et al., *Science,* 249:386–390 (1990); and Devlin et al., *Science,* 249:404–406 (1990).

Another approach involves large arrays of peptides that are synthesized in parallel and screened with acceptor molecules labelled with fluorescent or other reporter groups. The sequence of any effective peptide can be decoded from its address in the array (See e.g., Geysen et al., *Proc. Natl. Acad. Sci., USA,* 81:3998–4002 (1984); Maeji et al., *J. Immunol. Met.,* 146:83–90 (1992); and Fodor et al., *Science,* 251:767–775 (1991).

Combinatorial approaches can also be employed. For example, in one exemplary approach, combinatorial libraries of peptides are synthesized on resin beads such that each resin bead contains about 20 pmoles of the same peptide. The beads are screened with labeled acceptor molecules and those with bound acceptor are searched for by visual inspection, physically removed, and the peptide identified by direct sequence analysis (Lam et al., *Nature,* 354:82–84 (1991)). Another useful combinatory method for identification of peptides of desired activity is that of Houghten et al. (see, e.g., *Nature,* 354:84–86 (1991)). For hexapeptides of the 20 natural amino acids, 400 separate libraries are synthesized, each with the first two amino acids fixed and the remaining four positions occupied by all possible combinations. An assay, based on competition for binding or other activity, is then used to find the library with an active peptide. Twenty new libraries are then synthesized and assayed to determine the effective amino acid in the third position, and the process is reiterated in this fashion until the active hexapeptide is defined.

b. Chemical Conjugation

To effect chemical conjugation herein, the targeting agent is linked via one or more selected linkers or directly to the targeted agent. Chemical conjugation must be used if the targeted agent is other than a peptide or protein, such a nucleic acid or a non-peptide drug. Any means known to those of skill in the art for chemically conjugating selected moieties may be used.

1) Heterobifunctional Cross-linking Reagents

Numerous heterobifunctional cross-linking reagents that are used to form covalent bonds between amino groups and thiol groups and to introduce thiol groups into proteins, are known to those of skill in this art (see, e.g., the PIERCE CATALOG, ImmunoTechnology Catalog & Handbook, 1992–1993, which describes the preparation of and use of such reagents and provides a commercial source for such reagents; see, also, e.g., Cumber et al. (1992) *Bioconjugate Chem.* 3':397–401; Thorpe et al. (1987) *Cancer Res.* 47:5924–5931; Gordon et al. (1987) *Proc. Natl. Acad Sci.* 84:308–312; Walden et al. (1986) *J. Mol. Cell Immunol.* 2:191–197; Carlsson et al. (1978) *Biochem. J.* 173: 723–737; Mahan et al. (1987) *Anal. Biochem.* 162:163–170; Wawryznaczak et al. (1992) *Br. J. Cancer* 66:361–366; Fattom et al. (1992) *Infection & Immun.* 60:584–589). These reagents may be used to form covalent bonds between the mutant analyte binding enzyme and the facilitating agent. These reagents include, but are not limited to:

N-succinimidyl-3-(2-pyridyldithio)propionate (SPDP; disulfide linker); sulfosuccinimidyl 6-[3-(2-pyridyldithio) propionamido]hexanoate (sulfo-LC-SPDP); succinimidyloxycarbonyl-α-methyl benzyl thiosulfate (SMBT, hindered disulfate linker); succinimidyl 6-[3-(2-pyridyidithio)propionamido]hexanoate (LC-SPDP); sulfosuccinimidyl 4-(N-maleimidomethyl)cyclohexane-1-carboxylate (sulfo-SMCC); succinimidyl 3-(2-pyridyldithio)butyrate (SPDB; hindered disulfide bond linker); sulfosuccinimidyl 2-(7-azido-4-methylcoumarin-3-acetamide) ethyl-1,3'-dithiopropionate (SAED); sulfosuccinimidyl 7-azido-4-methylcoumarin-3-acetate (SAMCA); sulfosuccinimidyl 6-[alpha-methyl-alpha-(2-pyridyldithio)toluamido]hexanoate (sulfo-LC-SMPT); 1,4-di-[3'-(2'-pyridyidithio)propionamido]butane (DPDPB); 4-succinimidyloxycarbonyl-α-methyl-α-(2-pyridylthio) toluene (SMPT, hindered disulfate linker); sulfosuccinimidyl6[α-methyl-α-(2-pyridyidithio) toluamido]hexanoate (sulfo-LC-SMPT); m-maleimidobenzoyl-N-hydroxysuccinimide ester (MBS); m-maleimidobenzoyl-N-hydroxysulfosuccinimide ester (sulfo-MBS); N-succinimidyl(4-iodoacetyl)aminobenzoate (SIAB; thioether linker); sulfosuccinimidyl(4-iodoacetyl) amino benzoate (sulfo-SIAB); succinimidyl4(p-maleimidophenyl)butyrate (SMPB); sulfosuccinimidyl4-(p-maleimidophenyl)butyrate (sulfo-SMPB); azidobenzoyl hydrazide (ABH).

Other heterobifunctional cleavable cross-linkers include, N-succinimidyl (4-iodoacetyl)-aminobenzoate; sulfosuccinimydil(4-iodoacetyl)-aminobenzoate; 4-succinimidyl-oxycarbonyl-a-(2-pyridyidithio)-toluene; sulfosuccinimidyl-6-[a-methyl-a-(pyridyldithiol)-toluamido]hexanoate; N-succinimidyl-3-(-2-pyridyldithio)-proprionate; succinimidyl 6[3(-(-2-pyridyidithio)-proprionamido]hexanoate; sulfosuccinimidyl 6[3(-(-2-pyridyldithio)-propionamido]hexanoate; 3-(2-pyridyldithio)-propionyl hydrazide, Ellman's reagent, dichlorotriazinic acid, S-(2-thiopyridyl)-L-cysteine. Further exemplary bifunctional linking compounds are disclosed in U.S. Pat. Nos. 5,349,066, 5,618,528, 4,569,789, 4,952,394, and 5,137,877.

2) Exemplary Linkers

Any linker known to those of skill in the art for preparation of conjugates may be used herein. These linkers are typically used in the preparation of chemical conjugates; peptide linkers may be incorporated into fusion proteins.

Linkers can be any moiety suitable to associate a the mutant SAH-binding enzyme and the facilitating agent. Such linkers and linkages include, but are not limited to, peptidic linkages, amino acid and peptide linkages, typically containing between one and about 60 amino acids, more generally between about 10 and 30 amino acids,chemical linkers, such as heterobifunctional cleavable cross-linkers, including but are not limited to, N-succinimidyl (4-iodoacetyl)-aminobenzoate, sulfosuccinimydil (4-iodoacetyl)-aminobenzoate, 4-succinimidyl-oxycarbonyl-a-(2-pyridyldithio)toluene, sulfosuccinimidyl-6-[a-methyl-a-(pyridyidithiol)-toluamido]hexanoate, N-succinimidyl-3-(-2-pyridyldithio)-proprionate, succinimidyl 6[3(-(-2-pyridyldithio)-proprionamido]hexanoate, sulfosuccinimidyl 6[3(-(-2-pyridyldithio)-propionamido] hexanoate, 3-(2-pyridyldithio)-propionyl hydrazide, Ellman's reagent, dichlorotriazinic acid, and S-(2-thiopyridyl)-L-cysteine. Other linkers include, but are not limited to peptides and other moieties that reduce stearic hindrance between the mutant analyte binding enzyme and the facilitating agent, intracellular enzyme substrates, linkers that increase the flexibility of the conjugate, linkers that increase the solubility of the conjugate, linkers that increase the serum stability of the conjugate, photocleavable linkers and acid cleavable linkers.

Other exemplary linkers and linkages that are suitable for chemically linked conjugates include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid diihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. (1993) Molecular Immunol. 30:379–386). In some embodiments, several linkers may be included in order to take advantage of desired properties of each linker.

Chemical linkers and peptide linkers may be inserted by covalently coupling the linker to the mutant SAH-binding enzyme and the facilitating agent. The heterobifunctional agents, described below, may be used to effect such covalent coupling. Peptide linkers may also be linked by expressing DNA encoding the linker and TA, linker and targeted agent, or linker, targeted agent and TA as a fusion protein. Flexible linkers and linkers that increase solubility of the conjugates are contemplated for use, either alone or with other linkers are also contemplated herein.

a) Acid Cleavable, Photocleavable and Heat Sensitive Linkers

Acid cleavable linkers, photocleavable and heat sensitive linkers may also be used, particularly where it may be necessary to cleave the targeted agent to permit it to be more readily accessible to reaction. Acid cleavable linkers include, but are not limited to, bismaleimideothoxy propane; and adipic acid dihydrazide linkers (see, e.g., Fattom et al. (1992) Infection & Immun. 60:584–589) and acid labile transferrin conjugates that contain a sufficient portion of transferrin to permit entry into the intracellular transferrin cycling pathway (see, e.g., Welhöner et al. (1991) J. Biol. Chem. 266:4309–4314).

Photocleavable linkers are linkers that are cleaved upon exposure to light (see, e.g., Goldmacher et al. (1992) Bioconj. Chem. 3:104–107, which linkers are herein incorporated by reference), thereby releasing the targeted agent upon exposure to light. Photocleavable linkers that are cleaved upon exposure to light are known (see, e.g., Hazum et al. (1981) in Pept., Proc. Eur. Pept. Symp., 16th, Brunfeldt, K (Ed), pp. 105–110, which describes the use of a nitrobenzyl group as a photocleavable protective group for cysteine; Yen et al. (1989) Makromol. Chem 190:69–82, which describes water soluble photocleavable copolymers, including hydroxypropylmethacrylamide copolymer, glycine copolymer, fluorescein copolymer and methylrhodamine copolymer; Goldmacher et al. (1992) Bioconj. Chem. 3:104–107, which describes a cross-linker and reagent that undergoes photolytic degradation upon exposure to near UV light (350 nm); and Senter et al. (1985) Photochem. Photobiol 42:231–237, which describes nitrobenzyloxycarbonyl chloride cross linking reagents that produce photocleavable linkages), thereby releasing the targeted agent upon exposure to light. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are useful in connection with diagnostic protocols in which it is desirable to remove the targeting agent to permit rapid clearance from the body of the animal.

b) Other Linkers for Chemical Conjugation

Other linkers, include trityl linkers, particularly, derivatized trityl groups to generate a genus of conjugates that provide for release of therapeutic agents at various degrees of acidity or alkalinity. The flexibility thus afforded by the ability to preselect the pH range at which the therapeutic agent will be released allows selection of a linker based on the known physiological differences between tissues in need of delivery of a therapeutic agent (see, e.g., U.S. Pat. No. 5,612,474). For example, the acidity of tumor tissues appears to be lower than that of normal tissues.

c) Peptide Linkers

The linker moieties can be peptides. Peptide linkers can be employed in fusion proteins and also in chemically linked conjugates.. The peptide typically a has from about 2 to about 60 amino acid residues, for example from about 5 to about 40, or from about 10 to about 30 amino acid residues. The length selected will depend upon factors, such as the use for which the linker is included.

The proteinaceous ligand binds with specificity to a receptor(s) on one or more of the target cell(s) and is taken up by the target cell(s). In order to facilitate passage of the chimeric ligand-toxin into the target cell, it is presently preferred that the size of the chimeric ligand-toxin be no larger than can be taken up by the target cell of interest. Generally, the size of the chimeric ligand-toxin will depend upon its composition. In the case where the chimeric ligand toxin contains a chemical linker and a chemical toxin (i.e., rather than proteinaceous one), the size of the ligand toxin is generally smaller than when the chimeric ligand-toxin is a fusion protein. Peptidic linkers can conveniently be can be encoded by nucleic acid and incorporated in fusion proteins upon expressed in a host cell, such as $E.$ $coli.$ Peptide linkers are advantageous when the facilitating agent is proteinaceous. For example, the linker moiety can be a flexible spacer amino acid sequence, such as those known in single-chain antibody research. Examples of such known linker moieties include, but are not limited to, peptides, such as $(Gly_m Ser)_n$ and $(Ser_m Gly)_n$, in which n is 1 to 6, preferably 1 to 4, more preferably 2 to 4, and m is 1 to 6, preferably 1 to 4, more preferably 2 to 4, enzyme cleavable linkers and others.

Additional linking moieties are described, for example, in Huston et al., Proc. Natl. Acad. Sci. U.S.A. 85:5879–5883, 1988; Whitlow, M., et al., Protein Engineering 6:989–995, 1993; Newton et al, Biochemistry 35:545–553, 1996; A. J. Cumber et al., Bioconj. Chem. 3:397–401, 1992; Ladurner et al., J. Mol. Biol. 273:330–337, 1997; and U.S. Pat. No. 4,894,443. In some embodiments, several linkers may be included in order to take advantage of desired properties of each linker.

2. Selection of Facilitating Agents

Any agent that facilitates detection, immobilization, purification or targeted delivery of the conjugate is contemplated for use herein. For chemical conjugates, any moiety that has such properties is contemplated; for fusion proteins, the facilitating agent is a protein, peptide or fragment thereof that sufficient to effects the facilitating activity.

a. Protein Binding Moieties

The conjugate contains a protein binding moiety, particularly a protein binding protein, peptide or effective fragment thereof. Its specific binding partner can be a proteins or peptides generally, a set of proteins or peptides or mixtures thereof, or a particular protein or peptide. Any protein-protein interaction pair known to those of skill in the art is contemplated. For example, the protein-protein interaction pair can be enzyme/protein or peptide substrate, antibody/protein or peptide antigen, receptor/protein or peptide ligand, etc. Any protein-protein interaction pair can be designed, screened or selected according to the methods known in the art (See generally, Current Protocols in Molecular Biology (1998) §20, John Wiley & Sons, Inc.). Examples of such methods for identifying protein-protein interactions include the interaction trap/two-hybrid system and the phage-based expression cloning.

1) Interaction Trap/two-hybrid System

Interacting proteins can be identified by a selection or screen in which proteins that specifically interact with a target protein of interest are isolated from a library. One particularly approach to detect interacting proteins is the two-hybrid system or interaction trap (See generally, Current Protocols in Molecular Biology (1998) §20.1.–20.2., John Wiley & Sons, Inc.), which uses yeast as a "test tube" and transcriptional activation of a reporter system to identify associating proteins.

In the two-hybrid system, a yeast vector such as the plasmid pEG202 or a related vector can used to express the probe or "bait" protein as a fusion to the heterologous DNA-binding protein LexA. Many proteins, including transcription factors, kinases, and phosphatases, can be used as bait proteins. The major requirements for the bait protein are that it should not be actively excluded from the yeast nucleus, and it should not possess an intrinsic ability to strongly activate transcription. The plasmid expressing the LexA-fused bait protein can be used to transform yeast possessing a dual reporter system responsive to transcriptional activation through the LexA operator.

In one such example, the yeast strain EGY48 containing the reporter plasmid pSH18–34 can be used. In this case, binding sites for LexA are located upstream of two reporter genes. In the EGY48 strain, the upstream activating sequences of the chromosomal LEU2 gene, which is required in the biosynthetic pathway for leucine (Leu), are replaced with LexA operators (DNA binding sites). PSH18–34 contains a LexA operator-lacZ fusion gene. These two reporters allow selection for transcriptional activation by permitting selection for viability when cells are plated on medium lacking Leu, and discrimination based on color when the yeast is grown on medium containing Xgal.

The EGY48/PSH18–34 transformed with a bait is first characterized for its ability to express protein, growth on medium lacking Leu, and for the level of transcriptional activation of lacZ. A number of alternative strains, plasmids, and strategies can be employed if a bait proves to have an unacceptably high level of background transcriptional activation.

In an interactor hunt, the stain EGY48/PSH18–34 containing the bait expression plasmid is transformed, preferably along with carrier DNA, with a conditionally expressed library made in a suitable vector such as the vector pJG4–5. This library uses the inducible yeast GAL1 promoter to express proteins as fusions to an acidic domain ("acid blob") that functions as a portable transcriptional activation motif (act) and to other useful moieties. Expression of library-encoded proteins is induced by plating transformants on medium containing galactose (Gal), so yeast cells containing library proteins that do not interact specifically with the bait protein will fail to grow in the absence of Leu. Yeast cells containing library proteins that interact with the bait protein will form colonies within 2 to 5 days, and the colonies will turn blue when the cells are streaked on medium containing Xgal. The DNA from interaction trap positive colonies can be analyzed by polymerase chain reaction (PCR) to streamline screening and detect redundant clones in cases where many positives are obtained in screening. The plasmids can be isolated and characterized by a series of tests to confirm specificity of the interaction with the initial bait protein.

An alternative way of conducting an interactor hunt is to mate a strain that expresses the bait protein with a strain that has been pretransformed with the library DNA, and screen the resulting diploid cells for interactors (Bendixen et al., Nucl. Acids. Res., 22:1778–1779 (1994); and Finley and Brent, Proc. Nat. Sci. U.S.A., 91:12980–12984 (1994)). This "interaction mating" approach can be used for any interactor hunt, and is particularly useful in three special cases. The first case is when more than one bait will be used to screen a single library. Interaction mating allows several interactor hunts with different baits to be conducted using a single high-efficiency yeast transformation with library DNA. This can be a considerable savings, since the library transformation is one of the most challenging tasks in an interactor hunt. The second case is when a constitutively expressed bait interferes with yeast viability. For such baits, performing a hunt by interaction mating avoids the difficulty associated with achieving a high-efficiency library transformation of a strain expressing a toxic bait. Moreover, the actual selection for interactors will be conducted in diploid yeast, which are more vigorous than haploid yeast and can better tolerate expression of toxic proteins. The third case is when a bait cannot be used in a traditional interactor hunt using haploid yeast stains because it activates transcription of even the least sensitive reporters. In diploids the reporters are less sensitive to transcription activation than they are in haploids. Thus, the interaction mating hunt provides an additional method to reduce background from transactivating baits.

The interaction trap/two-hybrid system and the identified protein-protein interaction pairs have been successfully used (see, e.g., Bartel et al., Using the two-hybrid system to detect protein-protein interactions, In Cellular Interactions in Development: A Practical Approach, (D. A. Hartley, ed.) pp. 153–179, Oxford University Press, Oxford (1993); Bartel et al., A protein linkage map of Escherichia coli bacteriophage T7, Nature Genet., 12:72–77 (1996); Bendixen et al., A yeast mating-selection scheme for detection of protein-protein interactions, Nucl. Acids. Res., 22:1778–1779 (1994); Breeden and Nasmyth, Regulation of the yeast HO gene., Cold spring Harbor Symp. Quant. Biol, 50:643–650 (1985); Brent and Ptashne, A bacterial repressor protein or a yeast transcriptional terminator can block upstream activation of a yeast gene, Nature, 312:612–615 (1984); Brent et al., A eukaryotic transcriptional activator bearing the DNA specificity of a prokaryotic repressor, Cell, 43:729–736 (1985); Chien et al., The two-hybrid system: A method to identify and clone genes for proteins that interact with a protein of interest, Proc. Natl. Acad. Sci. U.S.A., 88:9578–9582 (1991); Chiu et al., RAPT1, a mammalian homolog of yeast Tor, interacts with the FKBP12/rapamycin complex, Proc. Nat. Acad. Sci., U.S.A., 91:12574–12578 (1994); Colas et al., Genetic selection of peptide aptamers that recognize and inhibit cyclin-dependent kinase 2., Nature, 380:548–550 (1996); Durfee et al., The retinoblastoma protein associates with the protein phosphatase type 1 catalytic subunit, Genes & Dev., 7:555–569 (1993); Estojak et al., Correlation of two-hybrid affinity data with in vitro measurements, Mol. Cell. Biol, 15:5820–5829 (1995); Fearon et al., Karyoplasmic interaction selection strategy: A general strategy to detect protein-protein interaction in mammalian cells, Proc. Nat., Acad. Sci. U.S.A., 89:7958–7962 (1992); Fields and Song, A novel genetic system to detect protein-protein interaction, Nature, 340:245–246 (1989); Finley and Brent, Interaction mating revels binary and ternary connections between Drosophila cell cycle regulators, Proc. Natl. Sci. U.S.A., 91:12980–12984 (1994); Gietz et al., Improved method for high-efficiency transformation of intact yeast cells, Nucl. Acids. Res., 20:1425 (1992); Golemis and Brent, Fused protein domains inhibit DNA biding by LexA, Mol. Cell Biol., 12:3006–3014 (1992); Gyuris et al., Cdi1, a human G1 and S-phase protein phosphatase that associates with Cdk1, Cell, 75:791–803 (1993); Kaiser et al., A., Methods in Yeast Genetics, a Cold Spring Harbor Laboratory Course Manual, pp. 135–136. Cold Spring Harbor Laboratory Press, Cold Spring Harbor, N.Y. (1994); Kolonin and Finley, Jr., Targeting cyclin-dependent kinases in Drosophila with peptide aptamers, Proc. Natl. Acad. Sci. U.S.A., In press (1998); Licitra and Liu, A three-hybrid system for detecting small ligand-protein receptor interactions, Proc. Nat. Acad. Sci. U.S.A., 93:12817–12821 (1996); Ma and Ptashne, A new class of yeast transcriptional activators, Cell, 51:113–119 (1987); Ma and Ptashne, Converting an eukaryotic transcriptional inhibitor into an activator, Cell, 55:443–446 (1988); Osborne et al., The yeast tribrid system: Genetic detection of transphosphorylated ITAM-SH2 interactions, Bio/Technology, 13:1474–1478 (1995); Ruden et al., Generating yeast transcriptional activators containing no yeast protein sequences, Nature, 350:426–430 (1991); Samson et al., Gene activation and DNA binding by Drosophila Ubx and abd-A proteins, Cell, 57:1045–1052 (1989); Stagljar et al., Use of the two-hybrid system and random sonicated DNA to identify the interaction domain of a protein, Bio Techniques, 21:430–432 (1996); Vasavada et al., A contingent replication assay for the detection of protein-protein interaction sin animal cells, Proc. Nat. Acad. Sci. U.S.A., 88:10686–10690 (1991); Vojtex et al., Mammalian Ras interacts directly with the serine/threonine kinase Raf, Cell, 74:205–214 (1993); Watson et al., Vectors encoding alternative antibiotic resistance for use in the yeast two-hybrid system, BioTechniques, 21:255–259 (1996); West et al., Saccharomyces cerevisiae GAL10 divergent promoter region: Location and function of the upstream activator sequence UASG, Mol. Cell Biol., 4:2467–2478 (1984); and Yang et al., Protein-peptide interactions analyzed with the yeast two-hybrid system, Nucl. Acids Res., 23:11 52–1156 (1995)) and can be used in the present system.

2) Phage-based Expression Cloning

Interaction cloning (also known as expression cloning) is a technique to identify and clone genes that encode proteins that interact with a protein of interest, or "bait" protein. Phage-based interaction cloning requires a gene encoding the bait protein and an appropriate expression library constructed in a bacteriophage expression vector, such as λgt11 (See generally, Current Protocols in Molecular Biology (1998) §20.3, John Wiley & Sons, Inc.). The gene encoding the bait protein is used to produce recombinant fusion protein in E. coli. The cDNA is radioactively labeled with $^{32}$P. A recognition site for a protein kinase such as the cyclic adenosine 3',5'-phosphate (cAMP)—dependent protein kinase (Protein kinase A; PKA) is introduced into the recombinant fusion protein to allow its enzymatic phosphorylation by the kinase and [λ-$^{32}$P]ATP.

In one example, the procedure involves a fusion protein containing bait protein and glutathione-S-transferase (GST) with a PKA site at the junction between them. The labeled protein is subsequently used as a probe to screen a λ bacteriophage-derived cDNA expression library, which expresses β-galactosidase fusion proteins that contain in-frame gene fusions. The phages lyse cells, form plaques, and release fusion proteins that are adsorbed onto nitrocellulose membrane filters. The filters are blocked with excess nonspecific protein to eliminate nonspecific binding and probed with the radiolabeled bait protein. This procedure leads directly to the isolation of genes encoding the interacting protein, bypassing the need for purification and microsequencing or for antibody production.

The phage-based interaction cloning system and the identified protein-protein interaction pairs have been successfully employed (Blanar et al., Interaction cloning: Identification of a helix-loop-helix zipper protein that interacts with c-Fos, Science, 256:1014–1018 (1992); Carr and Scott, Blotting and band-shifting: Techniques for studying protein-protein interactions, Trends Biochem. Sci., 17:246–249 (1992); Chapline et al., Interaction cloning of protein kinase C substrates, J. Biol. Chem., 268:6858–6861 (1993); Hoeffler et al., Identification of multiple nuclear factors that interact with cyclic AMP response element-binding protein and activation transcription factor-2 by protein interactions, Mol. Endocrinol., 5:256–266 (1991); Kaelin et al., Expression cloning of a cDNA encoding a retinoblastoma-binding protein with E2F-like properties, Cell, 70:351–364 (1992); Lester et al., Cloning and characterization of a novel A-kinase anchoring protein: AKAP220, association with testicular peroxisomes, J. Biol. Chem., 271:9460–9465 (1996); Lowenstein et al., The SH2 and SH2 domain-containing protein GRB2 links receptor tyrosine kinase to ras signaling, Cell, 70:431–442 (1992); Margolis et al., High-efficiency expression/cloning of epidermal growth factor-receptor-binding proteins with src homology 2 domains, Proc. Natl. Acad. Sci. U.S.A., 89:8894–8898 (1992); Skolnik et al., Cloning of P13 kinase-associated p85 utilizing a novel method of expression/cloning of target proteins for receptor tyrosine kinases, Cell, 65:83–90 (1991); and Stone et al., Interaction of a protein phosphatase with an Arabidopsis serine-threonine receptor kinase, Science, 266:793–795 (1994)) and can be used in the present system.

3) Detection of Protein-protein Interactions

Surface plasmon resonance (SPR) can be used to verify the protein-protein interactions identified by other systems such as the interaction trap/two-hybrid system and the phage-based expression cloning systems (See generally, Current Protocols in Molecular Biology (1998) §20.4, John Wiley & Sons, Inc.). This is an in vitro technique based on an optical phenomenon, called SPR, that can simultaneously detect interactions between unmodified proteins and directly measure kinetic parameters of the interaction.

SPR devices are commercially available. The BIAcore instrument (BIAcore) is presently preferred herein. This instrument contains sensing optics, an automated sample delivery system, and a computer for instrument control, data collection, and data processing. Experiments are performed on disposable chips. In practice, a ligand protein is immobilized on the chip while buffer continuously flows over the surface. The sensing apparatus monitors changes in the angle of minimum reflectance from the interface that result when a target protein associates with the ligand protein. Molecular interactions can be directly visualized (on the computer monitor) in real time as the optical response is plotted against time. This response is measured in resonance units (RUs, where 1000 RUs=1 ng protein/mm$^2$).

The SPR system has been successfully used (see, e.g., BioSupplyNet Source Book, BioSupplyNet, Plainview, N.Y., and Cold Spring Harbor Laboratory Press, Cold Spring Harbor, N.Y. (1999); Feng et al., Functional binding between Gβ and the LIM domain of Ste5 is required to activate the MEKK Ste11, Cur. Biol., 8:267–278 (1998); Field et al., Purification of RAS-responsive adenylyl cyclase complex from Sacchariomyces cerevisiae by use of an epitope addition method, Mol. Cell.. Biol., 8:2159–2165 (1988); Phizicky and Fields, Protein-protein interactions: Methods for detection and analysis, Microbiol. Rev., 59:94–123 (1995); Tyers et al., Comparison of the Saccharomyces cerevisiae G1 cyclins: Cln3 may be an upstream activator of Cln1, Cln2, and other cyclins, EMBO J., 11:1773–1784 (1993)) and the identified protein-protein interaction pairs can be used in the present system.

b. Epitope Tags

The facilitating agent can be any moiety, particularly a protein, peptide or effective fragment thereof that is specifically recognized by an antibody. In these embodiments, the conjugate contains an epitope tag that is specifically recognized by a set of antibodies or by a particular antibody. Any epitope/antibody pair can be used in the present system (See generally, Current Protocols in Molecular Biology (1998) 10.15, John Wiley & Sons, Inc.). The following Table 4 provides exemplary epitope tags illustrates certain properties of several commonly used epitope tag systems.

TABLE 4

Exemplary epitope tag systems

| Epitope | Peptide | SEQ ID | Antibody | Reference |
|---|---|---|---|---|
| FLAG | AspTyrLysAspAspAspLys | 5 | 4E11 | Prickett[1] |
| HA | TyrProTyrAspValPRoAspTyrAla | 6 | 12Ca5 | Xie[2] |
| HA1 | CysGlnAspLeuProGlyAsnSerThr | 7 | mouse MAb | Nagelkerken[3] |
| c-Myc | GluGlnLysLeuIleSerGluGluAspLeu | 8 | 9E10 | Xie[2] |
| 6-His | HisHisHisHisHisHis | 9 | BAbCO* | |
| AU1 | AspThrTyrArgTyrIle | 10 | BAbCO | |
| EE | GluTyrMetProMetGlu | 11 | anti-EE | Tolbert[4] |
| T7 | AlaSerMetThrGlyGlyGlnGlnMetGluArg | 12 | Invitrogen | Chen[5] Tseng[6] |
| 4A6 | SerPheProGlnPheLysProGlnGluIle | 13 | 4A6 | Rudiger[7] |
| ε | LysGluPheSerTyrPheGlyGluAspLeuMetPro | 14 | anti-PKCε | Olah[8] |
| B | GlnTyrProAlaLeuThr | 15 | D11, F10 | Wang[9] |

TABLE 4-continued

Exemplary epitope tag systems

| Epitope | Peptide | SEQ ID | Antibody | Reference |
|---|---|---|---|---|
| gE | GlnArgGlnTyrGlyAspValPheLysGlyAsp | 16 | 3B3 | Grose[10] |
| Ty1 | GluValHisThrAsnGlnAspProLeuAsp | 17 | BB2, TYG5 | Bastin[11] |

[1]Prickett et al., BioTechniques, 7(6):580–584 (1989)
[2]Xie et al., Endocrinology, 139(11):4563–4567 (1998)
[3]Nagelkerke et al., Electrophoresis, 18:2694–2698 (1997)
[4]Tolbert and Lameh, J. Neurochem., 70:113–119 (1998)
[5]Chen and Katz, BioTechniques, 25(1):22–24 (1998)
[6]Tseng and Verma, Gene, 169:287–288 (1996)
[7]Rudiger et al., BioTechniques, 23(1):96–97 (1997)
[8]Olah et al., Biochem., 221:94–102 (1994)
[9]Wang et al., Gene, 169(1):53–58 (1996)
[10]Grose, U.S. Pat. No. 5,710,248
[11]Bastin et al., Mol. Biochem. Parasitology, 77:235–239 (1996)
*Invitrogen, Sigma, Santa Cruz Biotech For example, in one embodiment, the selected epitope tag is the 6-His tag. Vectors for constructing a fusion protein containing the 6-His tag and reagents for isolating or purifying such fusion proteins are commercially available. For example, the Poly-His gene fusion vector from Invitrogen, Inc. (Carlsbad, Calif.) includes the following features: 1) high-level regulated transcription for the trc promotor; 2) enhanced translation efficiency of eukaryotic genes in E.coli; 3) the LacO operator and the LacI$^q$ repressor gene for transcriptional regulation in any E. coli system; N-terminal Xpress epitope for easy detection with an Anti-Xpress antibody; and 4) enterokinase cleaving site for removal of the fusion tag. The fusion protein can be purified by nickel-chelating agarose resin, and the purified fusion protein can be coated onto a microtiter plate pre-coated with nickel (e.g., Reacti-Binding meta chelate polystyrene plates, Pierce) for diagnostic usage.

In addition, the fusion protein containing the 6-His tag can be isolated or purified using the His MicroSpin Purification Module or HisTrap Kit from Amersham Pharmacia Biotech, Inc. The His MicroSpin Purification Module provides fifty MicroSpin columns prepacked with nickel-charged Chelating Sepharose Fast Flow. The module enables the simple and rapid screening of large numbers of small-scale bacterial lysates for the analysis of putative clones and optimization of expression and purification conditions. Each column contains 50 µl bed volume, enough to purify >100 µg his-tagged fusion protein, from up to 400 µl of his tagged fusion protein sample, e.g., crude lysate and purification intermediates. The HisTrap Kit is designed for rapid, mild affinity purification of histidine-tagged fusion proteins in a single step. The high dynamic capacity of HiTrap Chelating enables milligrams of protein to be purified in less than 15 minutes at flow rates of up to 240 column volumes per hour. The high capacity is maintained after repeated use ensuring cost-effective, reproducible purifications. The Kit includes three HiTrap Chelating columns and buffer concentrates to perform F10–12 purifications with a syringe. The anti-His antibody from Amersham Pharmacia Biotech, Inc. is an IgG$_2$ subclass of monoclonal antibody directed against 6 Histidine residues. The antibody is unconjugated to offer the flexibility of detection with a secondary antibody conjugated with either horseradish peroxidase or alkaline phosphatase. The antibody provides high sensitivity with low background.

Further examples of epitope tagging can be found in Kolodziej and Young, Epitope tagging and protein surveillance, Methods Enzymol., 194:508–519 (1991). Methods for preparing and using other such tags and other such tags similarly can be used in the methods and products provided herein.

c. IgG Binding Proteins

In other embodiments, the conjugate contains an IgG binding protein, which, for example provides a means for selective binding of the conjugate. Any IgG binding protein/IgG pair can be used in the present system. Protein A and Protein G are suitable facilitating. Any Protein A or Protein G can be used in the present system.

For example, the following nucleotide sequences can be used for amplifying and constructing Protein A or Protein G fusion proteins: E04365 (Primer for amplifying IgG binding domain AB of protein A); E04364 (Primer for amplifying IgG binding domain AB of protein A); E01756 (DNA sequence encoding subunit which can bind IgG of protein A like substance); M74187 (Cloning vector pKP497 (cloning, screening, fusion vector) encoding an IgG-binding fusion protein from protein A analogue (ZZ) and beta-Gal'(lacZ) genes). In addition, several Protein A gene fusion vectors such as pEZZ 18 and pRIT2T are commercially available (Amersham Pharmacia Biotech, Inc.).

1) pEZZ 18 Protein A Gene Fusion Vector pEZZ 18 Protein A gene fusion vector can be used for rapid expression of secreted fusion proteins and their one-step purification using IgG Sepharose 6FF. The phagemid pEZZ 18 contains the proteins A signal sequence and two synthetic "Z" domains based on the "B" IgG binding domain of Protein A (Löwenadler., et al., Gene, 58:87 (1987); and Nilsson., et al., Prot. Engineering, 1:107 (1987)). Proteins are expressed as fusions with the "ZZ" peptide and secreted into the aqueous culture medium under the direction of the protein A signal sequence. They are easily purified using IgG Sepharose 6FF to which the "ZZ" domain binds tightly. Because of its unique folding properties, the 14 kDa "ZZ" peptide has little effect on folding of the fusion partner into a native conformation.

Expression

Expression is controlled by the lacUV5 and protein A promotors and is not inducible. Elements of the protein A gene provide the ATG and ribosome-binding sites. Stop codons must be provided by the insert.

Sequencing

The M13 Universal Sequencing Primer is used for double-stranded and single-stranded sequencing. A protocol for production of single-stranded DNA is provided with the vector.

Cloning
　Inserts containing a stop codon will yield white colonies when grown on media containing X-gal.
Host(s)
　E. coli strains carrying a lac deletion but capable of α-complementaiton of lacZ'.
Selectable Marker(s)
　Plasmid confers resistance to ampicillin.
Amplification
　Amplification, though not necessarily required can be included.

2) pRIT2T Protein A Gene Fusion Vector

The pRIT2T Protein A gene fusion vector (available from Pharmacia) can be used for high-level expression of intracellular fusion proteins. pRIT2T, a derivative of pRIT2 (Nilsson., et al., *EMBO J.*, 4:1075 (1985)), contains the IgG-binding domains of staphylococcal protein A which permits rapid affinity purification of fusion proteins on IgG Sepharose 6 FF. Thermo-inducible expression of the fusion protein is achieved in a suitable *E. coli* host strain which carries the temperature-sensitive repressor c/857 (N4830-1) (Zabeau and Stanley, *EMBO J.*, 1:1217 (1982)).

Induction
　The $\lambda P_R$ promoter is induced by shifting the growth temperature from 30° C. to 42° C. for 90 minutes.
Expression
　Genes inserted into the MCS are expressed from the λ right promoter ($P_R$) as fusions with the IgG-binding domains of staphylococcal protein A. A portion of the λ cro gene, fused to the IgG-binding domain, supplies the ATG start codon. Since no signal sequence is provided, the protein remains intracellular. Protein A gene transcription and translation termination signals are provided. Fusion protein can be purified on IgG Sepharose 6FF (17-0969-01). The protein A carrier protein is ~30 kDa.
Host(s)
　*E. coli* N4830-1/N99cl+. Supplied with *E. coli* N4830-1 which contains the temperature-sensitive c/857 repressor.
Selectable Marker(s)
　Plasmid confers resistance to ampicillin.

3) The IgG Sepharose 6 Fast Flow System

The Protein A and Protein G fusion protein can be isolated or purified by affinity binding with IgG, such as the IgG Sepharose 6 Fast Flow System (Amersham Pharmacia Biotech, Inc.). The IgG Sepharose 6 Fast Flow System includes IgG coupled to the highly cross-linked 6% agarose matrix Sepharose 6 Fast Flow, and is designed for the rapid purification of Protein A and Protein A fusion conjugates. The system binds at least 2 mg Protein A/ml drained gel with flow possible rates of 300 cm/hr at 1 bar (14.5 psi, 0.1 MPa) in an XK 50/30 column (Lundström et al., *Biotechnology and Bioengineering*, 36:1056 (1990)).

d. β-galactosidase Fusion Proteins

The pMC1871 fusion vector (commercially available from Pharmacia, see, also Shapira et al. *Gene* 25:71 (1983); Casadaban et al. *Methods Enzymol.* 100:293 (1983)) for production of enzymatically active β-galactosidase hybrid proteins for gene expression or functional studies. Vector pMC1871 is derived from pBR322 and contains a promoterless lacZ gene, which also lacks a ribosome-binding site and the first eight non-essential N-terminal amino acids codons. Its unique Sma I site allows fusions to the N-terminal part of the β-galactosidase gene. Insertion of a gene into the *E. coil* lacZ gene results in the production of a hybrid protein, whose presence can be readily detected by following its β galactosidase activity (Miller, J. H., in Experiments in Molecular Gener. (Cold Spring Harbor, N.Y.) (1972); Nielsen et al. *Proc. Natl. Acad. Sci. U.S.A.*, 80:5198 (1983)). Hybrid proteins can then be easily purified by affinity chromatography (Germino et al. *Proc. Natl. Acad. Sci. U.S.A.*, 81: 4692 (1984)). Multiple cloning sites flanking the lacZ gene of permit its excision as a BamH I, Sal I, Pst I or EcoR I gene cassette. If lacZ is excised as an EcoRI cassette, a portion of its 3'-end will be deleted. The resulting β-galactosidase protein (a-donor) will be functional if the C-terminus of the β-galactosidase protein (α-acceptor) is available through intercistronic complementation.

Expression
　Inserts cloned into the unique Sma I site give fusion proteins with the N-terminal part of β-galactosidase. Insert must contain a promoter, ATG and ribosome-binding site.
Host(s)
　*E. coli* strains carrying a lac deletion.
Selectable Marker(s)
　Plasmid confers resistance to 15 μg/ml tetracycline.
　GenBank Accession Number L08936.

e. Nucleic Acid Binding Moieties

In another embodiment, the conjugate includes a nucleotide binding protein, peptide or effective fragment thereof as a facilitating agent. The specific binding partner can be nucleotide sequences generally, a set of nucleotide sequences or a particular nucleotide sequence. Any protein-nucleotide interaction pair can be used in the present system. For example, the protein-nucleotide interaction pair can be protein/DNA or protein/RNA pairs, or a combination thereof. Protein-nucleotide interaction pairs can be designed, screened or selected according to the methods known in the art (See generally, *Current Protocols in Molecular Biology* (1998) §12, John Wiley & Sons, Inc.). Examples of such methods for identifying protein-nucleotide interactions include the gel mobility shift assay, methylation and uracil interference assay, DNase I footprint analysis, λgt11 expression library screening and rapid separation of protein-bound DNA from free DNA using nitrocellulose filters.

1) DNA Binding Proteins

The conjugate can contain a DNA binding protein and its specific binding partner can be DNA molecules generally, a set of DNA molecules or a particular sequence of nucleotides. Any DNA binding protein can be used in the present system. For example, the DNA binding protein can bind to a single-stranded or double-stranded DNA sequence, or to an A-, B- or Z-form DNA sequence. The DNA binding sequence can also bind to a DNA sequence that is involved in replication, transcription, DNA repair, recombination, transposition or DNA structure maintenance. The DNA binding sequence can further be derived from a DNA binding enzyme such as a DNA polymerase, a DNA-dependent RNA polymerase, a DNAase, a DNA ligase, a DNA topoisomerase, a transposase, a DNA kinase, or a restriction enzyme.

Any DNA binding sequence/DNA sequence pair can be designed, screened or selected according to the methods known in the art including methods described in Section above.

The following Table 5 illustrates certain properties of several DNA binding sequence/DNA sequence pair systems.

TABLE 5

Examples of DNA binding sequence/DNA sequence binding pairs

| DNA binding sequence | DNA binding sequence motif | DNA sequence | Reference (U.S. Pat. No.) |
|---|---|---|---|
| NF-AT$_p$ (SEQ ID NO. 18) | T lymphocyte DNA-binding protein | GCCCAAAGAGGAA AATTTGTTTCATAC AG (SEQ ID NO. 19) | 5,656,452 |
| Max (SEQ ID NO. 20) | helix-loop-helix zipper protein | CACGTG | 5,693,487 |
| Chicken Lung 140 Kd Protein | | Z-DNA | 5,726,050 |
| EGR1, EGR2, GLI, Wilm's tumor gene, Sp1, Hunchback, Kruppel, ADR1 and BrLA | Zinc finger proteins | GACC, GCAC | 5,789,538 |
| LIL-Stat protein | Stat family of transcription factors | TTNCNNAGA, TTCCTGAGA | 5,821,053 |
| Egr (SEQ ID NO. 21) | zinc finger protein | CGCCCCCGC | 5,866,325 |
| S1-3 protein (SEQ ID NO. 22) | zinc finger protein | CATRRWWG | 5,905,146 |

2) RNA Binding Proteins

In another preferred embodiment, the conjugate can contain an RNA binding protein and its specific binding partner can be RNA generally, a set of RNA molecules or a particular sequence of ribonucleotides. Any RNA binding protein can be used in the present system. For example, the RNA binding protein can bind to a single-stranded or double-stranded RNA, or to rRNA, mRNA or tRNA. The RNA binding protein may specifically bind to a RNA that is involved in reverse transcription, transcription, RNA editing, RNA splicing, translation, RNA stabilization, RNA destabilization, or RNA localization. The RNA binding protein can be derived from or be an RNA binding enzyme such as a RNA-dependent DNA polymerase, a RNA-dependent RNA polymerase, a RNase, a RNA ligase, a RNA maturase, or a ribosome.

Other RNA recognition sequence or binding motifs that can be used in the present system include the zinc-finger motif, the Y-box, the KH motif, AUUUA, histone, RNP motif (U1), arginine-rich motif (ARM or PRE), double-stranded RNA binding motifs (IRE) and RGG box (APP) (U.S. Pat. Nos. 5,834,184, 5,859,227 and 5,858,675). The RNP motif is a 90–100 amino acid sequence that is present in one or more copies in proteins that bind pre mRNA, mRNA, pre-ribosomal RNA and snRNA. The consensus sequence and the sequences of several exemplary proteins containing the RNP motif are provided in Burd and Dreyfuss, *Science*, 265:615–621 (1994); Swanson et al., *Trends Biochem. Sci.*, 13:86 (1988); Bandziulis et al., *Genes Dev.*, 3:431 (1989); and Kenan et al., *Trends Biochem. Sci.*, 16:214 (1991). The RNP consensus motif contains two short consensus sequences RNP-1 and RNP-2. Some RNP proteins bind specific RNA sequences with high affinities (dissociation constant in the range of $10^{-8}$–$10^{-11}$ M). Such proteins often function in RNA processing reactions. Other RNP proteins have less stringent sequence requirements and bind less strongly (dissociation constant about $10^{-6}$–$10^{-7}$ M) (Burd & Dreyfuss, *EMBO J.*, 13:1197 (1994)).

A second characteristic RNA binding motif found in viral, phage and ribosomal proteins is an arginine-rich motif (ARM) of about 10–20 amino acids. RNA binding proteins having this motif include the HIV Tat and Rev proteins. Rev binds with high affinity disassociation constant ($10^{-9}$ M) to an RNA sequence termed RRE, which is found in all HIV mRNAs (Zapp et al., *Nature,* 342:714 (1989); and Dayton et al., *Science,* 246:1625 (1989)). Tat binds to an RNA sequence termed TAR with a dissociation constant of $5 \times 10^{-9}$ M (Churcher et al., *J. Mol. Biol,* 230:90 (1993)). For Tat and Rev proteins, a fragment containing the arginine-rich motif binds as strongly as the intact protein. In other RNA binding proteins with ARM motifs, residues outside the ARM also contribute to binding.

The double-stranded RNA-binding domain (dsRBD) exclusively binds double-stranded RNA or RNA-DNA. A dsRBD motif includes a region of approximately 70 amino acids which includes basic residues and contains a conserved core sequence with a predicted α-helical structure. The dsRBD motif is found in at least 20 known or putative RNA-binding proteins from different organisms. There are two types of dsRBDs; Type A, which is homologous along its entire length with the defined consensus sequence, and Type B, which is more highly conserved at its C terminus than its N terminus. These domains have been functionally delineated in specific proteins by deletion analysis and RNA binding assays (St Johnston, et al., *Proc. Natl. Acad. Sci.,* 89:10979–10983 (1992)).

Any RNA binding sequence/RNA sequence pair can be designed, screened or selected according to the methods known in the art including the methods described in Section L.2. above and the methods, such as those described in U.S. Pat. Nos. 5,834,184 and 5,859,227, and in SenGupta et al., A three-hybrid system to detect RNA-protein interactions in vivo, *Proc. Nat. Acad. Sci. U.S.A.,* 93:8496–8501 (1996)).

For example, U.S. Pat. No. 5,834,184 describes a method of screening a plurality of polypeptides for RNA binding activity. The method includes the steps of: (1) culturing a library of procaryotic cells the constitute a library, and (2) detecting expression of the reporter gene in a cell from the library, the expression indicating that the cell comprises a polypeptide having RNA binding activity. The cells contain at least one vector that contains a first DNA segment that encodes a fusion protein of a prokaryotic anti-terminator protein having anti-terminator activity linked in-frame to the test polypeptide, which varies among the cells in the library, that is operably linked to a second DNA segment. The second DNA segment contains a promoter, an RNA recognition sequence foreign to the anti-terminator protein, a transcription termination site and a reporter gene. The termination site blocks transcription of the reporter gene in the absence of a protein with anti-termination activity and affinity for the RNA recognition sequence. If the test polypeptide has specific affinity for the recognition sequence, it binds via the polypeptide to the RNA recognition sequence of a transcript from the second DNA segment thereby inducing transcription of the second DNA segment to proceed through the termination site to the reporter gene resulting in expression of the reporter gene.

U.S. Pat. No. 5,859,227 describes methods for identifying possible binding sites for RNA binding proteins in nucleic acid molecules, and confirming the identity of such prospective binding sites by detection of interaction between the prospective binding site and RNA binding proteins. Theses methods involve identification of possible binding sites for RNA binding proteins, by either searching databases for untranslated regions of gene sequences or cloning untranslated sequences using a single specific primer and an universal primer, followed by confirmation that the untranslated regions in fact interact with RNA binding proteins using the RNA/RBP detection assay. Genomic nucleic acid can further be screened for putative binding site motifs in the nucleic acid sequences. Information about binding sites that are confirmed in the assay then can be used to redefine or redirect the nucleic acid sequence search criteria, for example, by establishing or refining a consensus sequence for a given binding site motif.

SenGupta et al., *Proc. Nat. Acad. Sci. U.S.A.*, 93:8496–8501 (1996) describes a yeast genetic method to detect and analyze RNA-protein interactions in which the binding of a bifunctional RNA to each of two hybrid proteins activates transcription of a reporter gene in vivo (see also Wang et al., *Genes & Dev.*, 10:3028–3040 (1996)). SenGupta et al. demonstrate that this three-hybrid system enables the rapid, phenotypic detection of specific RNA-protein interactions. As examples, SenGupta et al. use the binding of the iron regulatory protein 1 (IRP1) to the iron response element (IRE), and of HIV trans-activator protein (Tat) to the HIV trans-activation response element (TAR) RNA sequence. The three-hybrid assay relies only on the physical properties of the RNA and protein, and not on their natural biological activities; as a result, it may have broad application in the identification of RNA-binding proteins and RNAs, as well as in the detailed analysis of their interactions.

The following Table 6 illustrates certain properties of several RNA binding sequence/RNA sequence pair systems.

TABLE 6

Examples of RNA binding sequence/RNA sequence pairs

| RNA binding sequence | RNA binding sequence motif | RNA sequence | Reference (U.S. Pat. No.) |
|---|---|---|---|
| BINDR | double-stranded RNA-binding | double-stranded RNA poly (rI) and poly (rC) | 5,858,675 |
| Protein extract from SH-SY5Y cells | 5' untranslated region (UTR) | UTR of Glut1 (SEQ ID NO. 23); 5' UTR of (HMG,CoA Red) (SEQ ID NO. 24); 5' UTR of human C4b-binding α chain (SEQ ID NO. 25); 5' UTR of human CD45 (SEQ ID NO. 26) | 5,859,227 |

3) Preparation of Nucleic Acid Binding Proteins

Extracts prepared from the isolated nuclei of cultured cells are functional in accurate in vitro transcription and mRNA processing (See generally, *Current Protocols in Molecular Biology* (1998) §12.1., John Wiley & Sons, Inc.). Thus, such extracts can be used directly for functional studies and as the starting material for purification of the proteins involved in these processes. To prepare nuclear extracts, tissue culture cells are collected, washed, and suspended in hypotonic buffer. The swollen cells are homogenized and nuclei are pelleted. The cytoplasmic fraction is removed and saved, and nuclei are resuspended in a low-salt buffer. Gentle dropwise addition of a high-salt buffer then releases soluble proteins from the nuclei (without lysing the nuclei). Following extraction, the nuclei are removed by centrifugation, the nuclear extract supernatant is dialyzed into a moderate salt solution, and any precipitated protein is removed by centrifugation.

The nuclear and cytoplasmic extraction procedure (see, e.g., Dignam et al., 1983, *Nucl. Acids. Res.* 11:1475–1489 (Accurate transcription initiation by RNA polymerase 11 in a soluble extract from isolated mammalian nuclei); Dignam, et al., 1983, *Methods Enzymol.* 101:582–598 (Eukaryotic gene transcription with purified components); Krainer, et al., 1984, *Cell* 36:993–1005 (Normal and mutant human β-globin pre-mRNAs are faithfully and efficiently spliced in vitro); Lue, et al, 1987, *Proc. Natl. Acad. Sci. U.S.A.* 84:8839–8843 (Accurate initiation at RNA polymerase II promoters in extracts from *Saccharomyces cerevisiae*); Manley, et al., 1980, *Proc. Natl. Acad. Sci. U.S.A.* 77:3855–3859 (DNA-dependent transcription of adenovirus genes in a soluble whole-cell extract); Weil, et al., 1979, *J. Biol. Chem.* 254:6163–6173 (Faithful transcription of eukaryotic genes by RNA polymerase IIII in systems reconstituted with purified DNA templates); and Weil, et al., 1979, *Cell* 18:469–484 (Selective and accurate initiation of transcription at the Ad2 major late promotor in a soluble system dependent on purified RNA polymerase II and DNA)) and the identified protein-DNA interaction pairs can be used in the present system.

4) Assays for Identifying Nucleic Acid Binding Proteins a) Mobility Shift DNA-binding Assay The DNA-binding assay using nondenaturing polyacrylamide gel electrophoresis (PAGE) provides a simple, rapid, and extremely sensitive method for detecting sequence-specific DNA-binding proteins (See generally, *Current Protocols in Molecular Biology* (1998) §12.2., John Wiley & Sons, Inc.). Proteins that bind specifically to an end-labeled DNA fragment retard the mobility of the fragment during electrophoresis, resulting in discrete bands corresponding to the individual protein-DNA complexes. The assay can be used to test binding of purified proteins or of uncharacterized factors found in crude extracts. This assay also permits quantitative determination of the affinity, abundance, association rate constants, dissociation rate constants, and binding specificity of DNA-binding proteins.

b) Basic Mobility Shift Assay Procedure

The basic mobility shift assay procedure includes 4 steps: (1) preparation of a radioactively labeled DNA probe containing a particular protein binding site; (2) preparation of a nondenaturing gel; (3) a binding reaction in which a protein mixture is bound to the DNA probe; and (4) electrophoresis of protein-DNA complexes through the gel, which is then dried and autoradiographed. The mobility of the DNA-binded protein is retarded while that of the non-binded protein is not retarded.

c) Competition Mobility Shift Assay

One important aspect of the mobility shift DNA-binding assay is the ease of assessing the sequence specificity of protein-DNA interactions using a competition binding assay. This is necessary because most protein preparations will contain specific and nonspecific DNA binding proteins. For a specific competitor, the same DNA fragment (unlabeled) as the probe can be used. The nonspecific competitor can be essentially any fragment with an unrelated sequence, but it is useful to roughly match the probe and specific competitor for size and configuration of the ends. For example, some proteins bind blunt DNA ends nonspecifically. These would not be competed by circular plasmid or a fragment with overhands, leading to the false conclusion that the protein-DNA complex represented specific binding. Perhaps the best control competitor is a DNA fragment that is identical to the probe fragment except for a mutation(s) in the binding site that is known to disrupt function (and presumably binding).

d) Antibody Supershift Assay

Another useful variation of the mobility shift DNA-binding assay is to use antibodies to identify proteins present in the protein-DNA complex. Addition of a specific antibody to a binding reaction can have one of several effects. If the protein recognized by the antibody is not involved in complex formation, addition of the antibody should have no effect. If the protein that forms the complex is recognized by the antibody, the antibody can either block complex formation, or it can form an antibody-protein-DNA ternary complex and thereby specifically result in a further reduction in the mobility of the protein-DNA complex (supershift). Results may be different depending upon whether the antibody is added before or after the protein binds DNA (particularly if there are epitopes on the DNA-binding surface of the protein).

The mobility shift DNA-binding assay has been successfully employed (see, e.g., Carthew, et al., 1985, *Cell* 43:439–448 (An RNA polymerase II transcription factor binds to an upstream element in the adenovirus major late promoter); Chodosh, et al., 1986, *Mol. Cell. Biol.* 6:4723–4733 (A single polypeptide possesses the binding and activities of the adenovirus major late transcription factor); Fried, et al., 1981, *Nucl. Acids. Res.*, 9:6505–6525 (Equilibria and kinetics of lac repressor-operator interactions by polyacrylamide gel electrophoresis); Fried, et al., 1984, *J. Mol. Biol.* 172:241–262 (Kinetics and mechanism in the reaction of gene regulatory proteins with DNA); Fried, et al., 1984, *J. Mol. Biol.* 172:263–282 (Equilibrium studies of the cyclic AMP receptor protein-DNA interaction); Garner, et al., 1981, *Nucl. Acids Res.* 9:3047–3060 (A gel electrophoresis method for quantifying the binding of proteins to specific DNA regions: Application to components of the *Escherichia coli* lactose operon regulatory system); Hendrickson, et al., 1984, *J. Mol. Biol.* 174:611–628 (Regulation of the *Escherichia coli* L-arabinose operon studied by gel electrophoresis DNA binding assay); Kristie, et al., 1986, *Proc. Natl. Acad. Sci. U.S.A.* 83:3218–3222 (The major regulatory protein of herpes simplex virus type 1, is stably and specifically associated with promoter-regulatory domains of a genes and/or selected viral genes); Lieberman, et al., 1994, *Genes & Dev.* 8:995–1006 (A mechanism for TAFs in transcriptional activation: Activation domain enhancement of TFIID-TFIIA-promoter DNA complex formation); Riggs, et al., 1970, *J. Mol. Biol.* 48:67–83 (Lac repressor-operator interactions: I. Equilibrium studies); Singh, et al., 1986, *Nature* 319:154–158 (A nuclear factor that binds to a conserved sequence motif in transcriptional control elements of immunoglobulin genes); Staudt, et al., 1986, *Nature* 323:640–643 (A lymphoid-specific protein binding to the octamer motif of immunoglobulin genes); Strauss, et al., 1984, *Cell* 37:889–901 (A protein binds to a satellite DNA repeat at three specific sites that would be brought into mutual proximity by DNA folding in the nucleosome); and Zinkel, et al., 1987, *Nature* 328:178–181 (DNA bend direction by phase-sensitive detection)) and the identified protein-DNA interaction pairs can be used in the present system.

e) Methylation and Uracil Interference Assay

Interference assays identify specific residues in the DNA binding site that, when modified, interfere with binding of the protein (See generally, *Current Protocols in Molecular Biology* (1998) §12.3., John Wiley & Sons, Inc.). These protocols use end-labeled DNA probes that are modified at an average of one site per molecule of probe. These probes are incubated with the protein of interests, and protein-DNA complexes are separated from free probe by the mobility shift assay. A DNA probe that is modified at a position that interferes with binding will not be retarded in this assay; thus, the specific protein-DNA complex is depleted for DNA that contains modifications on bases important for binding. After gel purification the bound and unbound DNA are specifically cleaved at the modified residues and the resulting products analyzed by electrophoresis on polyacrylamide sequencing gels and autoradiography. These procedures provide complementary information about the nucleotides involved in protein-DNA interactions.

1) Methylation Interference Assays

In methylation interference, probes are generated by methylating guanines (at the N-7 position) and adenines (at the N-3 position) with DMS; these methylated bases are cleaved specifically by piperidine. Methylation interference identifies guanines and adenines in the DNA binding site that, when methylated, interfere with binding of the protein. The protocol uses a single end-labeled DNA probe that is methylated at an average of one site per molecule of probe. The labeled probe is a substrate for a protein-binding reaction. DNA-protein complexes are separated from the free probe by the mobility shift DNA-binding assay. A DNA probe that is methylated at a position that interferes with binding will not be retarded in this assay. Therefore, the specific DNA-protein complex is depleted for DNA that contains methyl groups on purines important for binding. After gel purification, DNA is cleaved with piperidine. Finally, these fragments are electrophoresed on polyacrylamide sequencing gels and autoradiographed. Guanines and adenines that interfere with binding are revealed by their absence in the retarded complex relative to a lane containing piperidine-cleaved free probe. This procedure offers a rapid and highly analytical means of characterizing DNA-protein interactions.

2) Uracil Interference Assay

In uracil interference, probes are generated by PCR amplification in the presence of a mixture of TTP and dUTP, thereby producing products in which thymine residues are replaced by deoxyuracil residues (which contains hydrogen in place of the thymine 5-methyl group). Uracil bases are specifically cleaved by uracil-N-glycosylase to generate apyrimidinic sites that are susceptible to piperidine. Uracil interference identifies thymines in a DNA binding site that, when modified, interfere with binding of the protein. Probes generated by PCR amplification in the presence of TTP and dUTP incorporate deoxyuracil in place of thymine residues. PCR products are incubated with the binding protein and resulting complexes are separated from unbound DNA. The DNA recovered from the protein-DNA complex is treated with uracil-N-glycosylase and piperidine, and the products are then electrophoresed on a denaturing polyacrylamide gel.

The methylation and uracil interference assays have been successfully used (see, e.g., Baldwin, et al., 1988, *Proc. Natl. Acad. Sci. U.S.A.* 85:723–727 (Two transcription factors, H2TF1 and NF-kB, interact with a single regulatory sequence in the class I MHC promoter); Brunelle, et al., 1987, *Proc. Natl. Acad. Sci. U.S.A.* 84:6673–6676 (Missing contact probing of DNA-protein interactions); Goeddel, et al., 1978, *Proc. Natl. Acad. Sci. U.S.A.* 75:3579–3582 (How lac repressor recognizes lac operator); Ivarie, et al., 1987, *Nucl. Acids Res.* 15:9975–9983 (Thymine methyls and DNA-protein interactions); Maxam, et al., 1980, *Methods Enzymol* 65:499–560 (Sequencing end-labeled DNA with base-specific chemical cleavages); Pu, et al., 1992, *Nucl. Acids Res.* 20:771–775 (Uracil interference, a rapid and general method for defining protein-DNA interactions involving the 5-methyl group of thymines: The GCN4-DNA complex); Siebenlist, et al., 1980, *Proc. Natl. Acad. Sci. U.S.A.* 77:122–126 (Contacts between *E. coli* RNA polymerase and an early promoter of phase T7); and Hendrickson, et al., 1985, *Proc. Natl. Acad. Sci. U.S.A.* 82:3129–3133 (A dimer of AraC protein contacts three adjacent major groove regions at the Ara I DNA site)) and the identified protein-DNA interaction pairs can be used in the present system.

3) DNase I Footprint Analysis

Deoxyribonuclease I (DNase I) protection mapping, or footprinting, is a valuable technique for locating the specific binding sites of proteins on DNA (See generally, *Current Protocols in Molecular Biology* (1998) §12.4., John Wiley & Sons, Inc.). The basis of this assay is that bound protein protects that phosphodiester backbone of DNA from DNase I catalyzed hydrolysis. Binding sites are visualized by autoradiography of the DNA fragments that result form hydrolysis, following separation by electrophoresis on denaturing DNA sequencing gels. Footprinting has been developed further as a quantitative technique to determine separate binding curves for each individual protein-binding site on the DNA. For each binding site, the total energy of binding is determined directly from that site's binding curve. For sites that interact cooperatively, simultaneous numerical analysis of all the binding curves can be used to resolve the intrinsic binding and cooperative components of these energies.

DNase I footprint analysis has been successfully employed (see, e.g., Ackers, et al., 1982, *Proc. Natl. Acad. Sci. U.S.A.* 79:1129–1133 (Quantitative model for gene regulation by lambda phage repressor); Ackers, et al., 1983, *J. Mol. Biol.* 170:223–242 (Free energy coupling within macromolecules: The chemical work of ligand binding at the individual sites in cooperative systems); Brenowitz, et al., 1986, *Proc. Natl. Acad. Sci. U.S.A.* 83:8462–8466 (Footprint titrations yield valid thermodynamic isotherms.); Brenowitz, et al., 1986, *Meth. Enzymol.* 130:132–181 (Quantitative DNase I footprint titration: A method for studying protein-DNA interactions); Dabrowiak, et al., 1989, *In Chemistry and Physics of DNA-Ligand Interactions* (N. R. Kallenback, ed.) Adenine Press. (Quantitative footprinting analysis of drug-DNA interactions); Galas, et al., 1978, *Nucl. Acids Res.* 5:3157–3170 (DNase footprinting: A simple method for the detection of protein-DNA binding specificity); Hertzberg, et al., 1982, *J. Am. Chem. Soc.* 104:313–315 (Cleavage of double helical DNA by (methidiumpropyl-EDTA) iron (II)); Johnson, et al., 1979, *Proc. Natl. Acad. Sci. U.S.A.* 76:5061–5065 (Interactions between DNA-bound repressors govern regulation by the lambda phage repressor); Johnson, et al., 1985, *Meth. Enzymol.* 117:301–342 (Nonlinear least-squares analysis); Senear, et al., 1986, *Biochemistry* 25:7344–7354 (Energetics of cooperative protein-DNA interactions: Comparison between quantitative DNase I footprint titration and filter binding); and Tullius, et al., 1987, *Meth. Enzymol.* 155:537–558 (Hydroxyl radical footprinting: A high resolution method for mapping protein-DNA contacts), and the identified protein-DNA interaction pairs can be used in the present system.

4) Screening a λgt11 Expression Library with Recognition-site DNA

A clone encoding a sequence-specific protein can be detected in a λgt11 library because its recombinant protein binds specifically to a radiolabeled recognition-site DNA (See generally, *Current Protocols in Molecular Biology* (1998) §12.7., John Wiley & Sons, Inc.). Bacteriophage from a cDNA library constructed in the vector λgt11 are plated under lytic growth conditions. After plaques appear, expression of the β-galactosidase fusion proteins encoded by the recombinant phage is induced by placing nitrocellulose filters impregnated with IPTG onto the plate. Phage growth is continued and is accompanied by the immobilization of proteins, from lysed cells, onto the nitrocellulose filters. The filters are lifted after this incubation, blocked with protein, then reacted with a radiolabeled recognition-site DNA (containing one or more binding sites for the relevant sequence-specific protein) in the presence of an excess of nonspecific competitor DNA. After the binding reaction, the filters are washed to remove nonspecifically bound probe and processed for autoradiography. Potentially positive clones detected in the primary screen are rescreened after a round of plaque purification. Recombinants which screen positively after enrichment and whose detection specifically requires the recognition-site probe (non detected with control probes lacking the recognition site for the relevant protein) are then isolated by further rounds of plaque purification.

The λgt11 expression screening methods have been successfully used (see, e.g., Androphy, et al., 1987, *Nature (Lond.)* 325:70–73 (Bovine papillomavirus E2 trans-activating gene product binds to specific sites in papillomavirus DNA); Arndt, et al., 1986, *Proc. Natl. Acad. Sci. U.S.A.* 83:8516–8520 (GCN4 protein, a positive transcription factor in yeast, binds general control promoters at 5'TGACTC3' sequences); Chodosh, et al., 1988, *Cell* 53:25–35 (A yeast and a human CCAAT-binding protein have heterologous subunits that are functionally interchangeable); Desplan, et al., 1985, *Nature (Lond.)* 318:630–635 (The Drosophila developmental gene, engrailed, encodes a sequence-specific DNA binding activity); Hoeffler, et al., 1988,. *Science* 242:1430–1433 (Cyclic AMP-responsive DNA-binding protein: Structure based on a cloned placental cDNA); Hsiou-Chi, et al., 1988, *Science* 242:69–71 (Distinct cloned class II MHC DNA binding proteins recognize the X box transcription element); Ingraham, et al., 1988, *Cell* 55:519–529 (A tissue-specific transcription factor containing a homeo domain specifies a pituitary phenotype); Kadonaga, et al., 1987, *Cell* 51:1079–1090 (Isolation of cDNA encoding transcription factor Sp1 an functional analysis of the DNA binding domain); Keegan, et al., 1986, *Science* 231:699–704 (Separation of DNA binding from the transcription-activating function of a eukaryotic regulatory protein); Miyamoto, et al., 1988, *Cell* 54:903–913 (Regulated expression of a gene encoding a nucleic factor, IRF-1, that specifically binds to IFN-β gene regulatory elements); Murre, et al., 1989, *Cell* 56:777–783 (A new DNA binding and dimerization motif in immunoglobulin enhancer binding, daughterless, MyoD and myc proteins); Müller, et al., 1988, *Nature. (Lond.)* 336:544–551 (A cloned octamer transcription factor stimulates transcription from lymphoid specific promoters in non-B cells); Rawlins, et al., 1985, *Cell* 42:859–868 (Sequence-specific DNA binding of the Epstein-Barr viral nuclear antigen (EBNA-1) to clustered sites in the plasmid maintenance region); Reith, et al., 1989, *Proc. Natl. Acad. Sci. U.S.A.* 86:4200–4204 (Cloning of the major histocompatibility complex class II promoter affected in a hereditary defect in class II gene regulation); Singh, et al., 1988, *Cell* 52:415–423 (Molecular cloning of an enhancer binding protein: Isolation by screening of an expression library with a recognition site); Staudt, et al., 1988, *Science* 241:577–580 (Molecular cloning of a lymphoid-specific cDNA encoding a protein that binds to the regulatory octamer DNA motif); Sturm, et al., 1988, *Genes & Dev.* 2:1582–1599 (The ubiquitous octamer protein Oct-1 contains a Pou domain with a homeo subdomain); Vinson, et al., 1988, *Genes & Dev.* 2:801–806 (In situ detection of sequence-specific DNA binding activity specified by a recombinant bacteriophage); Weinberger, et al., 1985, *Sci-* ence 228:740–742 (Identification of human glucocorticoid receptor complementary DNA clones by epitope selection); and Young, et al., 1983, *Science* 222:778–782 (Yeast RNA polymerase II genes: Isolation with antibody probes)) and the identified protein-DNA interaction pairs can be used in the present system.

5) Rapid Separation of Protein-bound DNA from Free DNA

This method relies on the ability of nitrocellulose to bind proteins but not double-stranded DNA (See generally, *Current Protocols in Molecular Biology* (1998) §12.8., John Wiley & Sons, Inc.). Use of radioactively labeled double-stranded DNA fragments allows quantitation of DNA bound to the protein at various times and under various conditions, permitting kinetic and equilibrium studies of DNA-binding interactions. Purified protein is mixed with double-stranded DNA in an appropriate buffer to allow interaction. After incubation, the mixture is suction filtered through nitrocellulose, allowing unbound DNA to pass through the filter while the protein (and any DNA interacting with it) is retained.

Nitrocellulose filters methods have been successfully used (see, e.g., Barkley, et al., 1975, *Biochemistry* 14:1700–1712 (Interaction of effecting ligands with lac repressor and repressor-operator complex); Fried, et al., 1981, *Nucl. Acids Res.* 9:6505–6525 (Equilibria and kinetics of lac repressor-operator interactions by polyacrylamide gel electrophoresis); Hinkle, et al., 1972, *J. Mol. Biol.* 70:157–185 (Studies of the binding of *Escherichia coli* RNA polymerase to DNA I. The role of sigma subunit in site selection); Hinkle, et al., 1972, *J. Mol. Biol.* 70:187–195 (Studies of the binding of *Escherichia coli* RNA polymerase to DNA II. The kinetics of the binding reaction); Hinkle, et al., 1972, *J. Mol. Biol.* 70:197–207 (Studies of the binding of *Escherichia coli* RNA polymerase to DNA III. Tight binding of RNA polymerase holoenzyme to single-strand breaks in T7 DNA); Jones, et al., 1966, *J. Mol. Biol.* 22:199–209 (Studies on the binding of RNA polymerase to polynucleotides); Lin, et al., 1972, *J. Mol. Biol.* 72:671–690 (Lac repressor binding to non-operator DNA: Detailed studies and a comparison of equilibrium and rate competition methods); Lin, et al., 1975, *Cell* 4:107–111 (The general affinity of lac repressor for *E. coli* DNA: Implications for gene regulation in procaryotes and eucaryotes); Nirenberg, et al., 1964, *Science* 145:1399–1407 (RNA codewords and protein synthesis: The effect of trinucleotides upon the binding of sRNA to ribosomes); Ptashne, et al., 1987, A Genetic Switch: Gene Control and Phage λ pp. 80–83 and 109–118. Cell Press, Cambridge, Mass. and Blackwell Scientific, Boston, Mass.; Riggs, et al., 1970, *J. Mol. Biol.* 48:67–83 (Lac repressor-operator interactions: I. Equilibrium studies); Strauss, et al., 1980, *Biochemistry* 19:3496–3504 (Binding of *Escherichia coli* ribonucleic acid polymerase holoenzyme to a bacteriophage T7 promoter-containing fragment: Selectivity exists over a wide range of solution conditions); Strauss, et al., 1980, *Biochemistry* 19:3504–3515 (Binding of *Escherichia coli* ribonucleic acid polymerase holoenzyme to a bacteriophage T7 promoter-containing fragment: Evaluation of promoter binding constants as a function of solution conditions); and Strauss, et al., 1981, *Gene* 13:75–87 (Variables affecting the selectivity and efficiency of retention of DNA fragments by *E. coli* RNA polymerase in the nitrocellulose-filter binding assay)) and the identified protein-DNA interaction pairs can be used in the present system.

f. Lipid Binding Moieties

The conjugate can also contain a lipid binding protein, peptide or effective fragment thereof. Its specific binding partner can be lipids generally, a set of lipids or a particular lipid. Any lipid binding moiety, particularly proteins, peptides or effective fragments thereof can be used in the present system. For example, the lipid binding protein can bind to a triacylglycerol, a wax, a phosphoglyceride, a sphingolipid, a sterol and a sterol fatty acid ester. More preferably, the lipid binding sequence comprises a C2 motif or an amphipathic α-helix motif.

Any lipid binding sequence/lipid pair can be designed, screened or selected according to the methods known in the art (see, e.g., Kane et al., *Anal. Biochem.*, 233(2):197–204 (1996); Arnold et al., *Biochim. Biophys. Acta*, 1233(2):198–204 (1995); Miller and Cistola, *Mol. Cell. Biochem.*, 123(1–2):29–37 (1993); and Teegarden et al., *Anal. Biochem.*, 199(2):293–9 (1991).

For example, Kane et al., *Anal. Biochem.*, 233(2):197–204 (1996) describes that the fluorescent probe 1-anilinonapthalene 8-sulfonic acid (1,8-ANS) has been used to characterize a general assay for members of the intracellular lipid-binding protein (iLBP) multigene family. The adipocyte lipid-binding protein (ALBP), the keratinocyte lipid-binding protein (KLBP), the cellular retinol-binding protein (CRBP), and the cellular retinoic acid-binding protein I (CRABPI) have been characterized as to their ligand binding activities using 1,8-ANS. ALBP and KLBP exhibited the highest affinity probe binding with apparent dissociation constants (Kd) of 410 and 530 nM, respectively, while CRBP and CRABPI bound 1,8-ANS with apparent dissociation constants of 7.7 and 25 microM, respectively. In order to quantitate the fatty acid and retinoid binding specificity and affinity of ALBP, KLBP, and CRBP, a competition assay was developed to monitor the ability of various lipid molecules to displace bound 1,8-ANS from the binding cavity. Oleic acid and arachidonic acid displaced bound 1,8-ANS from ALBP, with apparent inhibitor constants (Ki) of 134 nM, while all-trans-retinoic acid exhibited a seven-fold lower Ki (870 nM). The short chain fatty acid octanoic acid and all-trans-retinol did not displace the fluorophore from ALBP to any measurable extent. In comparison, the displacement assay revealed that KLBP bound oleic acid and arachidonic acid with high affinity (Ki=420 and 400 nM, respectively) but bound all-trans-retinoic acid with a markedly reduced affinity (Ki=3.6 microM). Like that for ALBP, neither octanoic acid nor all-trans-retinol were bound by KLBP. Displacement of 1,8-ANS from CRBP by all-trans-retinal and all-trans-retinoic acid yielded Ki values of 1.7 and 5.3 microM, respectively. These results indicate the utility of the assay for characterizing the ligand binding characteristics of members of the iLBP family and suggests that this technique may be used to characterize the ligand binding properties of other hydrophobic ligand binding proteins.

Arnold et al., *Biochim. Biophys. Acta*, 1233(2):198–204 (1995) describes an assay for analyzing the specific binding of proteins to lipid ligands contained within vesicles or micelles. This assay, referred to as the electrophoretic migration shift assay, was developed using a model system composed of cholera toxin and of its physiological receptor, monosialoganglioside GM1. Using polyacrylamide gel electrophoresis in non-denaturing conditions, the migration of toxin components known to interact with GM1 was retarded when GM1 was present in either lipid vesicles or micelles. This effect was specific, as the migration of proteins not interacting with GM1 was not modified. The localization of retarded proteins and of lipids on gels was further determined by autoradiography. The stoichiometry of binding between cholera toxin and GM1 was determined, giving a value of five GM1 per one pentameric assembly of cholera toxin B-subunits, in agreement with previous studies. The general applicability of this assay was further established using streptavidin and annexin V together with specific lipid ligands. This assay is fast, simple, quantitative, and requires only microgram quantities of protein.

Miller and Cistola, *Mol. Cell. Biochem.*, 123(1–2):29–37 (1993) teaches that titration calorimetry can be used as a method for obtaining binding constants and thermodynamic parameters for the cytosolic fatty acid- and lipid-binding proteins. A feature of this method is its ability to accurately determine binding constants in a non-perturbing manner. This is achieved because the assay does not require separation of bound and free ligand to obtain binding parameters. Also, the structure of the lipid-protein complex was not perturbed, since native ligands were used rather than non-native analogues. As illustrated for liver fatty acid-binding protein, the method distinguished affinity classes whose dissociation constants differed by an order of magnitude or less. It also distinguished endothermic from exothermic binding reactions, as illustrated for the binding of two closely related bile salts to ileal lipid-binding protein. The main limitations of the method are its relatively low sensitivity and the difficulty working with highly insoluble ligands, such as cholesterol or saturated long-chain fatty acids. The signal-to-noise ratio was improved by manipulating the buffer conditions, as illustrated for oleate binding to rat intestinal fatty acid binding protein.

Teegarden et al., *Anal. Biochem.*, 199(2):293–9 (1991) describes an assay for measurement of the affinity of serum vitamin D binding protein for 25-hydroxyvitamin D3, 1,25-dihydroxyvitamin D3, and vitamin D3, using uniform diameter (6.4 microns) polystyrene beads coated with phosphatidylcholine and vitamin D metabolites as the vitamin D donor. The lipid metabolite coated beads have a solid core, and thus all of the vitamin D metabolites are on the bead surface from which transfer to protein occurs. After incubating these beads in neutral buffer for 3 h, essentially no $^3$H-labeled vitamin D metabolites desorb from this surface. Phosphatidylcholine/vitamin D metabolite-coated beads (1 microM vitamin D metabolite) were incubated with varying concentrations of serum vitamin D binding protein under conditions in which the bead surfaces were saturated with protein, but most of the protein was free in solution. After incubation, beads were rapidly centrifuged without disturbing the equilibrium of binding and vitamin D metabolite bound to sDBP in solution was assayed in the supernatant. All three vitamin D metabolites became bound to serum vitamin D binding protein, and after 10 min of incubation the transfer of the metabolites to serum vitamin D binding protein was time independent. The transfer followed a Langmuir isotherm, and the Kd for each metabolite binding to serum vitamin D binding protein was derived by nonlinear least-squares fit analysis. From this analysis the following values for the Kd were obtained: $5.59 \times 10^{-6}$ M, 25-hydroxyvitamin D; $9.45 \times 10^{-6}$ M, 1,25-dihydroxyvitamin D; and $9.17 \times 10^{-5}$ M, vitamin D. The method disclosed herein avoids problems encountered in previous assays and allows the precise and convenient determination of binding affinities of vitamin D metabolites and serum vitamin D binding protein.

In addition, known protein/lipid binding pairs can be used in the methods and with the products provided herein (see, e.g., Hinderliter et al., *Biochim. Biophys. Acta*, 1448(2): 227–35 (1998) (C2 motif binds phospholipid in a manner that is modulated by Ca2+ and confers membrane-binding ability on a wide variety of proteins, primarily proteins involved in signal transduction and membrane trafficking events); Campagna et al., *J. Diary Sci.*, 81(12):3139–48 (1998) (an amphipathic helical lipid-binding motif of a glycosylated phosphoprotein, component PP3 in bovine milk); Chae et al., *J. Biol. Chem.*, 273(40):25659–63 (1998) (The C2A domain of synaptotagmin I, which binds Ca2+ and anionic phospholipids); Johnson et al., *Biochemistry*, 37(26):9509–19 (1998) (the membrane binding domain of phosphocholine cytidylyltransferase (CT) includes of a continuous amphipathic alpha-helix between residues approximately 240–295 anionic lipids); Kiyosue et al., *Plant Mol. Biol.*, 35(6):969–72 (1997) (Ca2+-dependent lipid-binding domains of cytosolic phospholipase A2, protein kinase C, Rabphilin-3A, and Synaptotagmin 1 of animals); Welters et al., *Proc. Natl. Acad. Sci. USA*, 91(24):11398–402 (1994) (calcium-dependent lipid-binding domain is near the N terminus of phosphatidylinositol (PI) 3-kinase cloned from *Arabidopsis thaliana*); and Filoteo et al., *J. Biol. Chem.*, 267(17):11800–5 (1992) (Peptide G25:

LysLysAlaValLysValProLysLysG-
luLysSerValLeuGlnGlyLysLeuThrArgLeuAlaValGlnIle (SEQ ID No. 27) representing the putative lipid-binding region (G region) of the erythrocyte Ca2+ pump interacted with acidic lipids, as shown by the increase in size of phosphatidylserine liposomes in its presence)).

g. Polysaccharide Binding Moieties

The conjugate can include a polysaccharide binding protein, peptide or effective fragment thereof. Its specific binding partner can be polysaccharides generally, a set of polysaccharides or a particular polysaccharide. Any polysaccharide binding moiety, such as a protein, can be used in the present system and include but are not limited to a polysaccharide binding sequence that binds to starch, glycogen, cellulose or hyaluronic acid.

Any polysaccharide binding protein/polysaccharide pair can be designed, screened or selected according to the methods known in the art including the methods disclosed in Kuo et al., *J. Immunol. Methods*, 43(1):35–47 (1981); and Brandt et al., *J. Immunol.*, 108(4):913–20 (1972) (a radioactive antigen-binding assay for *Neisseria meningitidis* polysaccharide antibody). Kuo et al., *J. Immunol. Methods*, 43(1):35–47 (1981) provides a polyethylene glycol (PEG) radioimmunoprecipitation assay for the detection of antibody to *Haemophilus influenza* b capsular polysaccharide, polyribosylribitol phosphate (PRP). The radioactive antigen, [$^3$H]PRP, with a high specific activity, was produced by growing the organism in the presence of [$^3$H]ribose and was purified by hydroxylapatite and Sepharose™ 4B column chromatography. In the assay, PEG (12.5%) was used to separate antibody-bound [$^3$H]PRP from free [$^3$H]PRP. The assay covered the range of 0.5 and 20 ng antibody/assay at a maximum sensitivity of 0.5 approximately 1.0 ng antibody/assay. With various dilutions (1–20 ng antibody/assay) of S. Klein reference antiserum, the within-run coefficient of variation (CV) of 10 replicates ranged from 3.5 to 8.5%. Average CVs of 8.9% and 11.0% were obtained in the between-run and day-to-day reproducibility studies. The binding of [$^3$H]PRP to S. Klein reference antiserum was severely inhibited by a minute amount of non-radioactive PRP; however, no significant interference was found in the presence of high concentrations of polysaccharides from *Escherichia coli* K100 and *Streptococcus pneumoniae* indicating that the RIA was highly specific for antibody to *H. influenza* b PRP.

In addition, known protein/polysaccharide binding pairs can be used in the methods and with the products provided herein (see, e.g., Yamaguchi, et al., *Oral Microbiol. Immunol.*, 13(6):348–54 (1998) (capsule-like serotype-specific polysaccharide antigen lipopolysaccharide from Actinobacillus actinomycetemcomitans/human complement-derived opsonins); Lucas, et al., *J. Immunol.*, 161(7):3776–80 (1998) (kappa II-A2 light chain CDR-3 junctional residues in human antibody/Haemophilus influenza type b polysaccharide); Miller, et al., *Carbohydr. Res.*, 309(3):219–26 (1998) (fragments of the *Shigella dysenteriae* type 1 O-specific polysaccharide/monoclonal IgM 3707 E9); Prehm, et al., *Protein Expr. Purif.*, 7(4):343–6 (1996) (digitonin/hyaluronate synthase); Jiang, et al., *Infect. Immun.*, 63(7):2537–40 (1995) (mannose-binding protein/Klebsiella O3 lipopolysaccharide); Pelkonen, et al., *J. Bacteriol.*, 174(23):7757–61 (1992) (bacteriophage depolymerase/bacterial polysaccharide); Morishita, et al., *Biochem. Biophys. Res. Commun.*, 176(3):949–57 (1991) (Microbial polysaccharide, HS-142-1/guanylyl cyclase-containing receptor); Ohtomo, et al., *Can. J. Microbiol.*, 36(3):206–10 (1990) (staphylococcal cell surface polysaccharide/human fibrinogen); Yamagishi, et al., *FEBS Lett.*, 225(1–2):109–12 (1987) (heparin or dermatan sulfate/thrombin); DeAngelis, et al., *J. Biol. Chem.*, 262(29):13946–52 (1987) (sulfated fucans/bindin, the adhesive protein from sea urchin sperm); Volanakis, et al., *Mol. Immunol.*, 20(11):1201–7 (1983) (human C4/C-reactive protein-pneumococcal C-polysaccharide complexes); Naruse, et al., *J. Biochem.* (Tokyo), 90(3):581–7 (1981) (a polysaccharide from the cortex of sea urchin egg/microtubule-associated proteins); Levy, et al., *J. Exp. Med.*, 153(4):883–96 (1981) (agaropectin and heparin/human IgG proteins); Hu, et al., *Biochemistry*, 14(10):2224–30 (1975) (glycogen phosphorylase A/a series of semisynthetic, branched saccharides); Fagerstrom, *Microbiology*, 140(9):2399–407 (1994) (raw-starch-binding consensus amino acids in the C-terminal part of glucoamylase P); Murata, et al., *J. Vet. Med. Sci.*, 57(3):419–25 (1995) (C-polysaccharide/C-reactive protein (CRP)); Reason, et al., *Infect. Immun.*, 67(2):994–7 (1999) (Antibodies having light (L) chains encoded by the kappaII-A2 variable region/Haemophilus influenza type b polysaccharide (Hib PS)).

h. Metal Binding Moieties

The conjugate can contain a metal binding moiety, such as a metal binding protein, peptide or effective fragment thereof. The specific binding partner can be metal ions generally, a set of metal ions or a particular metal ion. Any metal binding moiety is contemplated. For example, the metal binding sequence can bind to a sodium, a potassium, a magnesium, a calcium, a chlorine, an iron, a copper, a zinc, a manganese, a cobalt, an iodine, a molybdenum, a vanadium, a nickel, a chromium, a fluorine, a silicon, a tin, a boron or an arsenic ion.

Any metal binding moiety/metal ion pair can be designed, screened or selected according to the methods known in the art including the methods disclosed in U.S. Pat. No. 5,679,548; Kang et al., *Virus Res.*, 49(2):147–54 (1997); Dealwis et al., *Biochemistry*, 34(43):13967–73 (1995); and Hutchens et al., *J. Chromatogr.*, 604(1):125–32 (1992).

U.S. Pat. No. 5,679,548 discloses a method for producing a metal binding site in a polypeptide capable of binding a preselected metal ion-containing molecule, the step of inducing mutagenesis of a complementarity determining region (CDR) of an immunoglobulin heavy or light chain gene, where the mutagenesis introduces a metal binding site, by amplifying the CDR of the gene by a primer extension reaction using a primer oligonucleotide, the oligonucleotide comprising: a) a 3' terminus and a 5' terminus comprising; b) a nucleotide sequence at the 3' terminus complementary to a first framework region of the heavy or light chain immunoglobulin gene; c) a nucleotide sequence at the 5' terminus complementary to a second framework region of the heavy or light chain immunoglobulin gene; and d) a nucleotide sequence between the 3' terminus and 5' terminus according to the formula; $[NNS]_a$, where N is independently any nucleotide, S is G or C, and a is from 3 to about 50, and the 3' and 5' terminal nucleotide sequences having a length of about 6 to 50 nucleotides, and sequences complementary thereto.

U.S. Pat. No. 5,679,548 also describes a method for producing a metal binding site in a polypeptide capable of binding a preselected metal ion-containing molecule, the step of inducing mutagenesis of a complementarity determining region (CDR) of an immunoglobulin heavy or light chain gene by amplifying the CDR of the gene by a primer extension reaction using a primer oligonucleotide, the oligonucleotide comprising: a) a 3' terminus and a 5' terminus; b) a nucleotide sequence at the 3' terminus complementary to a first framework region of the heavy or light chain immunoglobulin gene; c) a nucleotide sequence at the 5' terminus complementary to a second framework region of the heavy or light chain immunoglobulin gene; and d) a nucleotide sequence between 3' terminus and 5' terminus according to the formula: $-X-[NNK]_a-X-[NNK]-X$, where N is independently any nucleotide, K is G or T, X is a trinucleotide encoding a native amino acid residue coded by the immunoglobulin gene and a is from 3 to about 50, and the 3' and 5' terminal nucleotide sequences having a length of about 6 to 50 nucleotides, and sequences complementary thereto. Preferably, the immunoglobulin to be mutagenized is a human immunoglobulin, the CDR is CDR3, the mutagenizing oligonucleotide has the formula: 5'-GTGTATTATTGTGCGAGA$[NNS]_a$TGGGGCCAA-GGGACCACG-3' (SEQ ID No. 28), and the preselected metal ion-containing molecule is magnetite, copper(II), zinc (II), lead(II), cerium(III), or iron(III).

Kang et al., *Virus Res.*, 49(2):147–54 (1997) isolated human papillomavirus (HPV) type 18 E7 gene by polymerase chain reaction (PCR) amplification from tissues of Korean cervical cancer patients and cloned into a plasmid vector, pET-3a, for the expression of recombinant E7 protein (rE7) in *Escherichia coli*. The rE7 protein was purified to the homogeneity and its purity was confirmed by HPLC. The purified protein was analyzed for the metal-binding properties by UV spectroscopy and it was shown that two $Cd^{2+}$ or $Zn^{2+}$ ions bind to one E7 protein by the metal-sulfur ligand formation via two Cys-X-X-Cys motifs in E7 protein. When the change of intrinsic fluorescence of tryptophan residue was analyzed for rE7-Zn complex, the blue shift of emission wavelength and the decrease in maximum intensity of emission were observed compared with rE7. These results suggest that $Zn^{2+}$-bound rE7 has undergone conformational change, in which a tryptophan residue located in the second Cys-X-X-Cys motif was moved into solvent-inaccessible or hydrophobic environment.

Dealwis et al., *Biochemistry*, 34(43):13967–73 (1995) present the refined crystal structures of three different conformational states of the Asp153→Gly mutant (D153G) of alkaline phosphatase (AP), a metalloenzyme from *Escherichia coli*. The apo state is induced in the crystal over a 3 month period by metal depletion of the holoenzyme crystals. Subsequently, the metals are reintroduced in the crystalline state in a time-dependent reversible manner without physically damaging the crystals. Two structural intermediates of the holo form based on data from a 2 week (intermediate I)

and a 2 month soak (intermediate II) of the apo crystals with Mg$^{2+}$ and Zn$^{2+}$ have been identified. The three-dimensional crystal structures of the apo (R=18.1%), intermediate I (R=19.5%), and intermediate II (R=19.9%) of the D153G enzyme have been refined and the corresponding structures analyzed and compared. Large conformational changes that extend from the mutant active site to surface loops, located 20 A away, are observed in the apo structure with respect to the holo structure. The structure of intermediate I shows the recovery of the entire enzyme to an almost native-like conformation, with the exception of residues Asp 51 and Asp 369 in the active site and the surface loop (406–410) which remains partially disordered. In the three-dimensional structure of intermediate II, Asp 51 and Asp 369 are essentially in a native-like conformation, but the main chain of residues 406–408 within the loop is still not fully ordered. The D153G mutant protein exhibits weak, reversible, time dependent metal binding in solution and in the crystalline state.

Hutchens et al., *J. Chromatogr.*, 604(1):125–32 (1992) prepared synthetic peptides representing metal-binding protein surface domains from the human plasma metal transport protein known as histidine-rich glycoprotein (HRG) to evaluate biologically relevant peptide-metal ion interactions. Three synthetic peptides, representing multiples of a 5-residue repeat sequence (Gly-His-His-Pro-His) (SEQ ID No. 29) from within the histidine- and proline-rich region of the C-terminal domain were prepared. Prior to immobilization, the synthetic peptides were evaluated for identity and sample homogeneity by matrix-assisted UV laser desorption time-of-flight mass spectrometry (LDTOF-MS). Peptides with bound sodium and potassium ions were observed; however, these signal intensities were reduced by immersion of the sample probe tip in water. Mixtures of the three different synthetic peptides were also evaluated by LDTOF-MS after their elution through a special immobilized peptide-metal ion column designed to investigate metal ion transfer. It was found that LDTOF-MS to be a useful new method to verify the presence of peptide-bound metal ions.

In addition, the protein/metal binding pairs, which are known (see, e.g., DiDonato, et al., *Adv. Exp. Med. Biol.*, 448:165–73 (1999) (copper/copper binding domain from the Wilson disease copper transporting ATPase (ATP7B)); Buchko, et al., *Biochem Biophis. Res. Commun.*, 254(1): 109–13 (1999) (Zn$^{2+}$/Xenopus laevis nucleotide excision repair protein XPA); Lai, et al., *Biochemistry*, 37(48): 7005–15 (1998) (Zn$^{2+}$/hdm2 RING finder domain); Mitterauer, et al., *Biochemistry*, 37(46):16183–91 (1998) (The C2 catalytic domain of adenylyl cyclase contains the second metal ion (Mn2+) binding site); Hess, et al., *Protein Sci.*, 7(9):1970–5 (1998) (Zn$^{2+}$/Human nucleotide excision repair protein XPA); Goedken, et al., *Proteins*, 33(1):135–43 (1998) (Mg$^{2+}$ and Mn$^{2+}$/ribonuclease H domain of Moloney murine leukemia virus reverse transcriptase); Chang, et al., *Protein Eng.*, 11(1):41–6 (1998) (beta-domain of metallothionein); Champeil, et al., *J. Biol. Chem.*, 273(12) :6619–31 (1998) (cytosolic portion of sarcoplasmic reticulum Ca2+-ATPase); Bavoso, et al., *Biochem. Biophys. Res. Commun.*, 242(2):385–9 (1998) (zinc finger peptide containing the Cys-X2-Cys-X4-His-X4-Cys domain encoded by the Drosophila Fw-element); Gitschier, et al., *Nat. Struct. Biol.*, 5(1):47–54 (1998) (metal-binding domain from the Menkes copper-transporting ATPase); Gadhavi, *FEBS Lett.*, 417(1):145–9 (1997) (Zn$^{2+}$/ion binding site in the DNA binding domain of the yeast transcriptional activator GAL4); Roehm, et al., *Biochemistry*, 36(33):10240–5 (1997) (Zn$^{2+}$/ RING finger domain of BRCA1), Dalton, et al., *Mol. Cell Biol.*, 17(5):2781–9 (1997) (metal response element-binding transcription factor 1 DNA binding involves zinc interaction with the zinc finger domain); Essen, et al., *Biochemistry*, 36(10):2753–62 (1997) (Ca$^{2+}$/A ternary metal binding site in the C2 domain of phosphoinositide-specific phospholipase C-delta 1); Curtis, et al., *EMBO J.*, 16(4):834:43 (1997) (Zn$^{2+}$/CCHC metal-binding domain in Nanos); Worthington, et al., *Proc. Natl. Acad. Sci. USA*, 93(24): 13754–9 (1996) (zinc-binding domain of Nup475); Mahadevan, et al., *Biochemistry*, 34(7):2095–106 (1995) (Ba$^{2+}$, Ca$^{2+}$, Mg$^{2+}$, Mn$^{2+}$, Ni$^{2+}$, Zn$^{2+}$/A divalent metal ion binding site in the kinase insert domain of the alpha-platelet-derived growth factor receptor); Pan, et al., *Biochem. Biophys. Res. Commun.*, 202(1):621–8 (1994) (alpha and beta domains of mammalian metallothionein); Borden, et al., *FEBS Lett.*, 335(2):255–60 (1993) (Cu$^{2+}$, Zn$^{2+}$/cysteine/ histidine-rich metal binding domain from Xenopus nuclear factor XNF7); Chauhan, et al., *J. Bacteriol.*, 175(22):7222–7 (1993) (Mg$^{2+}$/*Bradyrhizobium japonicum* delta-aminolevulinic acid dehydratase is metal-binding domain); Knegtel, et al., *Biochem. Biophys. Res. Commun.*, 192(2): 492–8 (1993) (Zn$^{2+}$/metal coordination in the human retinoic acid receptor-beta DNA binding domain); Spencer, et al., *Biochem. J.*, 290(1):279–87 (1993) (Co$^{2+}$, Mg$^{2+}$, Zn$^{2+}$/ 5-aminolaevulinic acid dehydratase from *Escherichia coli* reactive thiols at the metal-binding domain); Mau, et al., *Protein Sci.*, 1(11):1403–12 (1992) (Zn$^{2+}$/GAL4 DNA-binding domain); Vaughan, et al., *Virology*, 189(1):377–84 (1992) (Zn$^{2+}$/The herpes simplex virus immediate early protein ICP27 metal binding domain); Boese, et al., *J. Biol. Chem.*, 266(26):17060–6 (1991) (Mg$^{2+}$/Aminolevulinic acid dehydratase in pea metal-binding domain); Hutchens, et al., *J. Biol. Chem.*, 264(29):17206–12 (1989) (Cu$^{2+}$, Ni$^{2+}$, Zn$^{2+}$/ DNA-binding estrogen receptor); Stillman, et al., *Biochem. J.*, 262(1):181–8 (1989) (Cd$^{2+}$ and Zn$^{2+}$/rabbit liver metallothionein 2); Freedman, et al., *Nature*, 334(6182):543–6 (1988) (Cd$^{2+}$ and Zn$^{2+}$/metal coordination sites within the glucocorticoid receptor DNA binding domain); Stillman, et al., *J. Biol. Chem.*, 263(13):6128–33 (1988) (Cd$^{2+}$ and Zn$^{2+}$/metallothionein); and Corson, et al., *Biochemistry*, 25(7):1817–26 (1986) (Ca$^{2+}$/calcium-binding proteins C-terminal alpha-helix of a helix-loop-helix metal-binding domain)) can be used in the present system.

Among the preferred pairs, are the following metal binding sequence/metal ion pairs (see, U.S. Pat. No. 5,679,548) set forth in the following table.

TABLE 7

Examples of Metal Ion Binding Sequence/Metal Ion Pairs

| Metal Ion | Metal Ion Binding Sequence | SEQ ID NO. |
|---|---|---|
| Mg(II) | SerArgArgSerArgHisHisProArgMetTrpAs GlyLeuAspVal | 30 |
| | GlyArgPheLysArgValArgAspArgTrpValValIlePheAspPhe | 31 |
| | GlyValAlaArgSerLysLysMetArgGlyLeuTrpArgLeuAspVal | 32 |
| | GlyLeuAlaValArgserLysArgGlyArgPhePheLeuPheAspVal | 33 |

TABLE 7-continued

Examples of Metal Ion Binding Sequence/Metal Ion Pairs

| Metal Ion | Metal Ion Binding Sequence | SEQ ID NO. |
|---|---|---|
| Cu(II) | GlyArgValHisHisHisSerLeuAspVal | 34 |
| | SerTrpLysHisHisAlaHisTrpAspVal | 35 |
| | GlySerTrpAspHisArgGlyCysAspGly | 36 |
| | GlyHisHisMetTyrGlyGlyTrpAspHis | 37 |
| | GlyHisTrpGlyArgHisSerLeuAspThr | 38 |
| | GlyHisIleLeuHisHisGlnLeuAspLeu | 39 |
| | SerSerGlnArgLeuMetLeuGlyAspAsn | 40 |
| | SerHisHisGlyHisHisTyrLeuAsnHis | 41 |
| | GlyLysLeuMetMetSerTrpCysArgAspThrGluGlyCysAspHis | 42 |
| | GlyAspThrHisArgGlyHisLeuArgHisHisLeuProHisAspTrp | 43 |
| | GlyTrpGlyLeuTrpMetLysProPheValTrpArgAlaTrpAspMet | 44 |
| Zn(II) | GlyArgValHisHisHisSerLeuAspVal | 45 |
| | SerHisThrHisAlaLeuProLeuAspPhe | 46 |
| | GlyGlnSerSerGlyGlyAspThrAspAsp | 47 |
| | GlyGlnTrpThrProArgGlyAspAspPhe | 48 |
| | GlyArgCysCysProSerSerCysAspGlu | 49 |
| | GlyProAlaLysHisArgHisArgHisValGlyGlnMetHisAspSer | 50 |
| Pb(III) | GlyAsnLeuArgArgLysThrSerAspIle | 51 |
| | GlyGluSerAspSerLysArgGluAspGly | 52 |
| | GlyGlyProSerLeuAlaValGlyAspTrp | 53 |
| | GlyProLeuGlnHisThrTyrProAspTyr | 54 |
| | GlyTrpLysValThrAlaGluAspSerThrGluGlyLeuPheAspLeu | 55 |
| | GlyThrArgValTrpArgValCysGlnTrpAsnHisGluGluAspGly | 56 |
| | GlyGluTrpTrpCysSerPheAlaMetCysProAlaArgTrpAspPhe | 57 |
| | GlyAspThrIlePheGlyValThrMetGlyTyrTyrAlaMetAspVal | 58 |
| Ce(III) | GlyGlnValMetGlnGluLeuGlyAspAla | 59 |
| | GlyLeuThrGluGlnGlnLeuGlnAspGly | 60 |
| | GlyTyrSerTyrSerValSerProAspAla | 61 |
| | GlyArgLeuGlyLeuValMetThrAspGlu | 62 |
| | SerThrTrpProGlyArgGlnArgLeuGlyGlnAlaLeuSerAspSer | 63 |
| | GlyTyrGluLeuSerTrpGlyValAspGlnGlnGluTrpTrpAspIle | 64 |
| | GlyProValArgGlyLeuAspGlnSerLysGlyValArgTyrAspAsn | 65 |
| | GlyLeuSerGlnHisIleValSerGluThrGlnSerSerGlyAspLeu | 66 |
| | GlyLeuGluSerLeuLysValLeuGlyValGlnLeuGlyGlyAspLeu | 67 |
| | GlyAsnMetIleLeuGlyGlyProGlyCysTrpSerSerAlaAspIle | 68 |
| | GlyCysTrpAsnValGlnArgLeuValValTyrHisProProAspGly | 69 |
| | GlyPheGluValThrCysSerTrpPheGlyHisTrpGlyArgAspSer | 70 |
| Fe(III) | SerAlaSerMetArgSerAlaIleGlyLeuTrpArgThrMetAspTyr | 71 |
| | GlyAspArgGluIlePheHisMetGlnTrpProLeuArgValAspVal | 72 |
| | SerGlnAsnProGlnGlnValCysGlyValArgCysGlyGlnAspLys | 73 |
| | GlyAsnArgLeuSerSerGlyHisLeuLeuLysGlnGlyGlnAspGly | 74 |
| | GlyGlySerAspTrpGlnIleGlyAlaCysCysArgGluAspAspLeu | 75 |
| | GlyMetValSerMetMetGlyGlnSerArgProThrGlnCysAspCys | 76 |
| | GlyValIleLysTrpIleArgArgTrpValArgThrAlaArgAspVal | 77 |
| | GlyTrpPheTrpArgLeuLeuProThrProArgAlaProSerAspVal | 78 | i. Other Facilitating Agents

Facilitating agents can be derived from an enzyme, a transport protein, a nutrient or storage protein, a contractile or motile protein, a structural protein, a defense protein, a regulatory protein, or a fluorescent protein. Exemplary of such other fragments are those derived from an enzyme such as a peroxidase, a urease, an alkaline phosphatase, a luciferase and a glutathione S-transferase.

1) Peroxidase

Any peroxidase can be used in the present system. More preferably, a horseradish peroxidase is used. For example, the horseradish peroxidases with the following GenBank accession Nos. can be used: E01651; D90116 (prxC3 gene); D90115 (prxC2 gene); J05552 (Synthetic isoenzyme C(HRP-C)); S14268 (neutral); OPRHC (C1 precursor); S00627 (C1C precursor); JH0150 (C3 precursor); S00626 (C1B precursor); JH0149 (C2 precursor); CAA00083 (*Armoracia rusticana*); and AAA72223 (synthetic horseradish peroxidase isoenzyme C (HRP-C)).

2) Urease

Any urease can be used in the present system. For example, the ureases with the following GenBank accession Nos. can be used: AF085729 (*Ureaplasma urealyticum* serovar); AF056321 (*Actinomyces naeslundii*); AF095636 (*Yersinia pestis*); AF006062 (*Filobasidiella neoformans* var. *neoformans* (URE1)); U81509 (*Coccidioides immitis* urease); AF000579 (*Bordetella bronchiseptica*); U352248 (*Streptococcus salivarius*); U33011 (*Mycobacterium tuberculosis*); U89957 (*Actinobacillus pleuropneumoniae* urease operon (ureABCXEFGD); D14439 (*Thermophilic Bacillus*); L40490 (*Ureaplasma urealyticum* T960 urease); L40489 (*Ureaplasma urealyticum* strain 7); U40842 (*Yersinia pseudotuberculosis*); M65260 (*Canavalia ensiformis*); U29368 (*Bacillus pasteurii* ure operon); L25079 (*Heliobacter heilmannii* urease); L24101 (*Yersinia enterocolitica*); M31834 (*P.mirabilis* urease operon); M36068 (*K.aerogenes*); L07039 (*Kiebsiella pneumoniae*); M60398 (*H.pylori*); L03308 (*E.coli* urease gene cluster); L03307 (*E.coli* urease gene cluster).

3) Alkaline Phosphatase

Any alkaline phosphatase can be used in the present system. For example, the alkaline phosphatases encoded by nucleic acids with the following GenBank accession Nos. can be used: AB013386 (*Bombyx mori* s-Alp soluble alkaline phosphatase); AF154110 (*Enterococcus faecalis* (phoZ); M13077 (Human placental); AF052227 (*Bos taurus* intestinal); AF052226 (*Bos taurus* intestinal); AF079878 (Thermus sp. (TAP)); AF047381 (*Pseudomonas aeruginosa* (phoA)); U49060 (*Bacillus subtilis* (phoD)); J03930 (Human intestinal (ALPI)); J03252 (Human alkaline (ALPP)); U19108 (Gallus tissue-nonspecific); M13345 (*E. coli*); U31569 (*Felis catus* (alpI)); L36230 (*Zymomonas mobilis* (phoD)); M19159 (Human placental heat-stable (PLAP-1)); M12551 (Human placental (PLAP)); M31008 (Human intestinal); J04948 (Human (ALP-1); J03572 (Rat); M61705 (Mouse intestinal (IAP); M61704 (Mouse embryonic); M61706 (Mouse (AP) pseudogene); M21134 (*S.cerevisiae* (rALPase)); L07733 (Cow intestinal (IAP)); M18443 (Bovine); M77507 (Synechococcus sp. atypical); M33965 (*S.marcescens* (phoA)); M33966 (*E.fergusonii* (phoA)); M29670 (*E.coli* (phoA)); M29669 (*E.coli* (phoA)); M29668 (*E.coli* (phoA)); M29667 (*E.coli* (phoA)); M29666 (*E.coli* (phoA)); M29665 (*E.coli* (phoA)); M29664 (*E.coli* (phoA)); M29663 (*E.coli* (phoA)); M23549 (*Bacillus subtilis* (phoP gene, 3' end and phoR gene); M16775 (*B.subtilis* phoP); M33634 (*B.subtilis* (phoAIII); L27993 (*Neurospora crassa*); U02550 (*Bacillus subtilis* (phoA)).

4) Luciferase

Any luciferase can be used in the present system. Numerous luciferases are available and have been cloned. For example, the luciferases encoded by nucleic acids with the following GenBank accession Nos. can be used: AH00771 1 (*Streptomyces clavuligerus* (cvm5)); AF124929 (cvm5); U43958 (Cloning vector pRcCMV-luc luciferase gene); M90092 (*Xenorhabdus luminescens* (luxA)); AF093688 (MMTV-luciferase reporter vector pHH Luc *SA *PS); AF093687 (MMTV-luciferase reporter vector PHH Luc *SA); AF093686 (MMTV-luciferase reporter vector pHH Luc); AF093685 (Luciferase reporter vector pXP2 *SA *PS); AF093684 (Luciferase reporter vector pXP2 *SA); AF093683 (Luciferase reporter vector pXP1); AF093682 (Luciferase reporter vector pXP2); U40374 (Luciferase reporter gene shuttle vector pMH30); AF003893 (*Gonyaulax polyedra* luciferase); L39928 (*Pyrocoelia miyako* (clone pB-PmL41); L39929 (*Hotaria parvula* (clone pB-Hp); AF085332 (*Gonyaulax polyedra*); U89490 (*Vargula hilgendorfii*); AF027129 (Eukaryotic luciferase expression vector pCMVtkLUC+); AF027128 (Eukaryotic luciferase expression vector ptkLUC+); AF027127 (Eukaryotic luciferase expression vector pTATALUC+); AF027126 (Eukaryotic luciferase expression vector pLUC+); U31240 (*Photuris pennsylvanica*); D25416 (Firefly clone pPFL7); D25415 (Firefly clone pPFL19); U84006 (Expression vector pBSII-LUCINT firefly luciferase (LUCINT); U55819 (Plasmid pRL765 with transposon Tn5 and luciferase (luxA and luxB) genes); U55385 (Plasmid pRL1063a with transposon Tn5 and luciferase (luxA and luxB) genes); U51019 (*Luciola lateralis*); U49182 (*Luciola lateralis*); U49181 (*Luciola lateralis*); M36597 (*K. alfredi* symbiont); U47298 (Cloning vector pGL-3-Promoter firefly luciferase (luc+) gene); U47297 (Cloning vector pGL3-Enhancer firefly luciferase (luc+) gene); U47296 (Cloning vector pGL3-Control firefly luciferase (luc+) gene); U47295 (Cloning vector pGL3-Basic firefly luciferase (luc+) gene); U47123 (Cloning vector pSP-luc+NF, luciferase cassette fusion vector); U47122 (Cloning vector pSP-luc+, Luciferase cassette vector); M10961 (*V.harveyi* (luxA and luxB); M65067 (*Photobacterium phosphoreum* (luxA and luxB); M62917 (*Xenorhabdus luminescens* (luxA, luxB, luxC, and luxD); M25666 (*V.hilgendorfii*); M63501 (*Renilla reniformis*); M15077 (*P.pyralis* (firefly)); M26194 (*Luciola cruciata*); M55977 (*X.luminescens* (luxA and luxB)); M90093 (*Xenorhabdus luminescens* (luxA) and (luxB) (luxE)); U03687 (*Photinus pyralis* modified luciferase gene).

5) Glutathione S-transferase

A glutathione S-transferase (GST), more preferably a *Schistosoma japonicum* glutathione S-transferase, can be included in the conjugate. GST occurs naturally as a 26 kDa protein which can be expressed in *E. coli* with full enzymatic activity. Conjugates that contain the full length GST also demonstrate GST enzymatic activity and can undergo dimerization as observed in nature (Parker et al., *J. Mol. Biol.*, 213:221 (1990); Ji, et al., *Biochemistry*, 31:10169 (1992); and Maru et al., *J. Biol. Chem.*, 271:15353 (1996)). The crystal structure of recombinant *Schistosoma japonicum* GST from pGEX vectors has been determined (McTigue et al., *J. Mol. Biol.*, 246:21 (1995)) and matches that of the native protein. Conjugates that contain a GST can be readily purified.

For example, fusion proteins are easily purified from bacterial lysates by affinity chromatography using Glutathione Sepharose 4B contained in the GST Purification Modules (Amersham Pharmacia Biotech, Inc.). Cleavage of the desired protein from GST is achieved using a site-specific protease whose recognition sequence is located immediately upstream from the multiple cloning site on the pGEX plasmids. Fusion proteins can be detected using a colorimetric assay or immunoassay provided in the GST Detection Module, or by Western blotting with anti-GST antibody. The system has been used successfully in many applications such as molecular immunology (Toye et al., *Infect. Immun.*, 58:3909 (1990)), the production of vaccines (Fikrig et al., *Science*, 250:553 (1990); and Johnson et al., *Nature*, 338:585 (1989)) and studies involving protein-protein (Kaelin et al., *Cell*, 64:521 (1991)) and DNA-protein (Kaelin et al., *Cell*, 65:1073 (1991)) interactions.

Any glutathione S-transferase is contemplated. For example, the glutathione S-transferase encoded by nucleic acid with the following GenBank accession Nos. can be used: [AF112567], *Fasciola gigantica*; [M77682], *Fasciola hepatica*; [AB016426], *Cavia porcellus*; [AF144382], *Arabidopsis thaliana*; [AF133251], Gallus; [AB021655], *Issatchenkia orientalis*; [AF133268], *Manduca sexta*; [AF125273], *Homo sapiens* tissue-type skeletal muscle; [AF125271], *Homo sapiens* tissue-type pancreas; [AB026292], *Sphingomonas paucimobilis*; [AB026119], *Oncorhynchus nerka*; [U49179], *Bos taurus*; [AF106661], *Rattus norvegicus* (GstYb4); [L15387], Gallus class-alpha; [AF051318], *Clonorchis sinensis*; [AF101269], *Echinococcus granulosus*; [AF077609], *Boophilus microplus*; [AA956087], *Homo sapiens* microsomal; [AF004358], *Aegilops squarrosa*; [AF109714], *Triticum aestivum*; [U86635], *Rattus norvegicus* glutathione; [AF111428], *Drosophila melanogaster* microsomal; [AF111426], *Drosophila melanogaster* microsomal; [AF071163], *Anopheles gambiae*; [AF071162], *Anopheles gambiae*; [AF071161], *Anopheles gambiae*; [AF071160], *Anopheles gambiae*; [D10524], *Nicotiana tabacum*; [AF062403], *Oryza sativa*; [U77604], *Homo sapiens* microsomal (MGST2); [U30897], Human (P1b); [U62589], Human (GSTp1c); [U42463], *Coccomyxa* sp. PA; [AF001779], *Sphingomonas paucimobilis* strain epa505; [U51165], *Cycloclasticus oligotrophus* (XYLK); [AF025887], *Homo sapiens* (GSTA4); [U66342], *Plutella xylostella*; [AF051238], *Picea mariana* (Sb52); [AF051214], *Picea mariana* (Sb18); [AF079511], *Mesembryanthemum crystallinum* clone R6-R37; [D10026], *Rattus norvegicus* Yrs-Yrs; [AF048978], *Glycine max* 2,4-D inducible (GSTa); [AF043105], *Homo sapiens* (GSTM3); [AF057172], *Homo sapiens* (GSTT2P); [U21689], Human;

[AH006027], *Homo sapiens* (GSTT2); [AF057176], *Homo sapiens* (GSTT2); [AF050102], *Oryza sativa* (GST1); [AF044411], *Schistosoma japonicum*; [U87958], *Culicoides variipennis* (CVGST1); [AF026977], *Homo sapiens* microsomal (MGST3); [AF027740], *Homo sapiens* microsomal (MGST1L1); [AF005928], *Echinococcus granulosus*; [AF001103], Pseudomonas (phnC); [AF010241], *Caenorhabditis elegans* (CeGST3); [AF010240], *Caenorhabditis elegans* (CeGST2); [AF010239], *Caenorhabditis elegans* (CeGST1); [AF002692], *Solanum commersonii* (GST1); [L38503], *Homo sapiens* (GSTT2); [M97937], *E. coli/S. japonicium*; [L29427], Rat GST-P gene; [M14654], *Schistosoma japonicum* Sj26 antigen; [AB000884], *Sus scrofa*; [D44465], *Arabidopsis thaliana*; [D17673], *Arabidopsis thaliana*; [D17672], *Arabidopsis thaliana*; [U78784], *Anopheles dirus*; [U71213], Human microsomal; [U70672], *Arabidopsis thaliana*; [U24428], *Mus musculus*; [U43126], *Naegleria fowleri*; [X14233], *D.melanogaster* (GST); [L32092], *Manduca sexta*; [L32091], *Manduca sexta*; [U30489], *Arabidopsis thaliana*; [M24889], Artificial maize; [L05915], *Dianthus caryophyllus*; [M15872], Human; [L23766], *Oryctolagus cuniculus*; [J03679], *Solanum tuberosum*; [U12472], Human (GST phi); [U15654], *Mus musculus*; [M24485], *Homo sapiens* (GSTP1); [L28771], *Onchocerca volvulus*; [M14777], Human; [M16594], Human; [M21758], Human; [J03914], Rat; [K01932], Rat liver; [J02810], Rat prostate; [M25891], Rat; [M1719], Rat liver; [M28241], Rat; [J03752], Rat; [M73483], Mouse (GST Yc); [J04696], Mouse (GST5-5); [J04632], Mouse (GST1-1); [M59772], *M.auratus*; [L20466], Chinese hamster; [M25627], Human liver; [J03746], Human (SEQ ID No. 79); [M16901], Maize; [M64268], *Dianthus caryophyllus*; [L11601], *Arabidopsis thaliana*; [L07589], *Arabidopsis thaliana*; [M74529], *Oryctolagus cuniculus*; [M74528], *Oryctolagus cuniculus*; [M98271], *Schistosoma mansoni* 28 kDa; [L23126], *Lucilia cuprina*; [M95198], *Drosophila melanogaster*; [L26544], Methylophilus sp.; [U14753], *Dirofilaria immitus*; [U12679], *Zea mays*; [L02321], Human (GSTM5); [L15386], Chicken.

In addition, commercially available Glutathione S-transferase (GST) gene fusion system can be used. For example, the Glutathione S-transferase (GST) Gene Fusion System (Amersham Pharmacia Biotech, Inc.) can be used. The system from Amersham Pharmacia Biotech, Inc. is an integrated system for the expression, purification and detection of fusion proteins produced in *E. coli*. The system includes three primary components: pGEX plasmid vectors, various options for GST purification and a variety of GST detection products. A series of site-specific proteases complements the system. The pGEX plasmids are designed for inducible, high-level intracellular expression of genes or gene fragments as fusions with *Schistosoma japonicum* GST (Smith and Johnson, *Gene*, 67:31 (1988)). All pGEX Vectors (GST Gene fusion) offer: 1) A tac promoter for chemically inducible, high-level expression; 2) an internal lac I$^q$ gene for use in any *E. coli* host; 3) very mild elution conditions for release of fusion proteins form the affinity matrix, thus minimizing effects on antigenicity and functional activity; and 4) PreScission, thrombin or factor Xa protease recognition sites for cleaving the desired protein from the fusion product.

The GST Detection Module from Amersham Pharmacia Biotech, Inc. can be used for identification of GST fusion proteins using either a biochemical or immunological assay. In the biochemical assay, glutathione and 1-chloro-2-4-dinitrobenzene (CDNB) serve as substrates for GST to yield a yellow product detectable at 340 nm (Habig et al., *J. Biol. Chem.*, 249:7130 (1974)). An affinity-purified goat anti-GST polyclonal antibody suitable for Western blots is used in the immunoassay.

The GST 96-Well Detection Module from Amersham Pharmacia Biotech, Inc. contains five microtitre strip plates, horseradish perioxidase (HRP) conjugated anti-GST antibody and recombinant GST protein. The wells of each plate are coated with purified anti-GST antibody to capture GST fusion proteins and are preblocked to provide a low background. HRP conjugated antibody enables sensitive detection of GST proteins.

The anti-GST antibody supplied in the system from Amersham Pharmacia Biotech, Inc. is a polyclonal antibody purified from the sera of goats immunized with purified schistosomal glutathione S-transferase (GST). Because of its polyclonal nature, it can recognize more than one epitope on GST, thereby improving its capacity for recognizing GST fusion proteins even if some binding sites are masked due to recombinant protein folding.

Factor Xa can be used for site-specific separation of the GST affinity tag from proteins expressed using pGEX X vectors. Factor Xa enables the site-specific cleavage of fusion proteins containing an accessible Factor Xa recognition sequence. It can be used either following affinity purification or while fusion proteins are bound to Glutathione Sepharose 4B. Factor Xa, purified from bovine plasma, is used to digest fusion proteins prepared from pGEX vectors containing the recognition sequence for factor Xa (pGEX-3X, pGEX-5X-1, pGEX-5X-2 and pGEX-5X-3). It specifically cleaves following the tetrapeptide Ile-Glu-Gly-Arg (SEQ ID No. 80) (Nagai and Thøgersen, *Nature*, 309:810 (1984); and Nagai and Thøgersen, *Methods Enzymol.*, 153:461 (1987)). In the system from Amersham Pharmacia Biotech, Inc., one unit of Factor Xa cleaves ≧90% of 100 μg of a test GST fusion protein when incubated in 1 mM $CaCl_2$, 100 mM NaCl and 50 mM Tris-HCl (pH 8.0) at 22° C. for 16 hours.

PreScission protease can be used for site-specific separation of the GST affinity tag from proteins expressed using pGEX-6P vectors. It enables the low-temperature cleavage of fusion proteins containing the PreScission Protease recognition sequence. It can be used either following affinity purification or while fusion proteins are bound to Glutathione Sepharose 4B. PreScission Protease is a genetically engineered fusion protein containing human rhinovirus 3C protease and GST (Walker et al., *Bio/Technology*, 12:601 (1994)). This protease was specifically designed to facilitate removal of the protease by allowing simultaneous protease immobilization and cleavage of GST fusion proteins produced from pGEX-6P vectors (pGEX-6P-1, pGEX-6P-2, and pGEX-6P-3). PreScission Protease specifically cleaves between the Gln and Gly residues of the recognition sequence of LeuGluValLeuPheGln/GlyPro (SEQ ID No. 81) (Cordingley et al., *J. Bio. Chem.*, 265:9062 (1990)). In the system from Amersham Pharmacia Biotech, Inc., one unit of PreScission protease will cleave≧90% of 100 μg of a test GST-fusion protein in 50 mM Tris-HCl, 150 mM NaCl, 1 mM EDTA, 1 mM DTT, pH 7.0 at 5° C. for 16 hours.

Thrombin can be used for site-specific separation of the GST affinity tag from proteins expressed using pGEX T vectors. It enables the site-specific cleavage of fusion proteins containing an accessible thrombin recognition sequence. It is purified from bovine plasma; functionally free of other clotting factors, plasminogen and plasmin. It can be used either following affinity purification or while fusion proteins are bound to Glutathione Sepharose 4B.

Thrombin is used to digest fusion proteins prepared from pGEX vectors containing the recognition sequence for thrombin (pGEX-1λT, pGEX-2T, pGEX-2TK, pGEX-4T-1, pGEX-4T2 and pGEX-4T-3). In the system from Amersham Pharmacia Biotech, Inc., one unit of Thrombin cleaves≧90% of 100 μg of a test GST fusion protein when incubated in 1×PBS at 22° C. for 16 hours.

6) Defense Proteins

The conjugates can contain defense protein, such as an antibody. Any antibody, including polyclonal, monoclonal, single chain or Fab fragments, can be used.

7) Fluorescent Moieties

The conjugates can contain a fluorescent moiety, such as a green, a blue or a red fluorescent protein. Any green, blue or red fluorescent protein can be used in the present system. For instances, the green fluorescent proteins encoded by nucleic acids with the following GenBank accession Nos. can be used: U47949 (AGP1); U43284; AF007834 (GFPuv); U89686 (*Saccharomyces cerevisiae* synthetic green fluorescent protein (cox3::GFPm-3) gene); U89685 (*Saccharomyces cerevisiae* synthetic green fluorescent protein (cox3::GFPm) gene); U87974 (Synthetic construct modified green fluorescent protein GFP5-ER (mgfp5-ER)); U87973 (Synthetic construct modified green fluorescent protein GFP5 (mgfp5)); U87 625 (Synthetic construct modified green fluorescent protein GFP-ER (mfgp4-ER)); U87624 (Synthetic construct green fluorescent protein (mgfp4) mRNA)); U73901 (*Aequorea victoria* mutant 3); U50963 (Synthetic); U70495 (soluble-modified green fluorescent protein (smGFP)); U57609 (enhanced green fluorescent protein gene); U57608 (enhanced green fluorescent protein gene); U57607 (enhanced green fluorescent protein gene); U57606 (enhanced green fluorescent protein gene); U55763 (enhanced green fluorescent protein (egfp)); U55762 (enhanced green fluorescent protein (egfp); U55761 (enhanced green fluorescent protein (egfp); U54830 (Synthetic *E. coli* Tn3-derived transposon green fluorescent protein (GF); U36202; U36201; U19282; U19279; U19277; U19276; U19281; U19280; U19278; L29345 (*Aequorea Victoria*); M62654 (*Aequorea Victoria*); M62653 (*Aequorea Victoria*); AAB47853 ((U87625) synthetic construct modified green fluorescent protein (GFP-ER)); AAB47852 ((U87624) synthetic construct green fluorescent protein).

Similarly, the blue fluorescent proteins encoded by nucleic acids with the following GenBank accession Nos. can be used: U70497 (soluble-modified blue fluorescent protein (smBFP); 1BFP (blue variant of green fluorescent protein); AAB16959 (soluble-modified blue fluorescent protein).

Also similarly, the red fluorescent proteins encoded by nucleic acids with the following GenBank accession Nos. can be used: U70496 (soluble-modified red-shifted green fluorescent protein (smRSGFP); AAB16958 ((U70496) soluble-modified red-shifted green fluorescent protein).

E. IMMOBILIZATION OF MUTANT SAH-BINDING ENZYMES

In the methods for assaying the activity of SAM-dependent methyl-transferases or screening for modulators of such SAM-dependent methyl-transferases described in the above Sections B-C, the mutant SAH-binding enzyme or complex thereof can be immobilized on the surface of a support, either directly or via a linker. Preferably, the support used is an insoluble support such as a silicon chip. Non-limiting examples of the geometry of the support include beads, pellets, disks, capillaries, hollow fibers, needles, solid fibers, random shapes, thin films, membranes and chips.

Also more preferably, the mutant SAH-binding enzyme or complex thereof is immobilized in an array or a well format on the surface.

1. Immobilization of the Mutant SAH-binding Enzymes

In certain embodiments, where the facilitating agents are designed for linkage to surfaces, recovered, isolated or purified conjugates, such as fusion proteins can be attached to a surface of a matrix material. Immobilization may be effected directly or via a linker. The conjugates may be immobilized on any suitable support, including, but are not limited to, silicon chips, and other supports described herein and known to those of skill in the art. A plurality of conjugates, which may contain the same or different or a variety of mutant SAH-binding enzymes (SAH trapping enzymes) may be attached to a support, such as an array (i.e., a pattern of two or more) of conjugates on the surface of a silicon chip or other chip for use in high throughput protocols and formats.

It is also noted that the mutant SAH-binding enzymes can be linked directly to the surface or via a linker without a facilitating agent linked thereto. Hence chips containing arrays of mutant SAH-binding enzymes are contemplated.

For example, an isolated or purified fusion protein can be attached to the surface as the intact fusion proteins. Alternatively, the protein or peptide fragment portion can be cleaved off and the mutant SAH-binding enzyme be attached to the surface. The fusion protein can be cleaved by any methods known in the art such as chemical or enzymatic means. The cleavage means must be compatible with the linking sequence between the protein or peptide fragment portion and the mutant SAH-binding enzyme so that the cleavage is linker sequence specific and the cleaved mutant enzyme is functional, i.e., can be used as a SAH-trapping enzyme. Those skilled in the art can readily determine, if necessary, with empirical studies, which cleavage/linker sequence pair to be used. Many cleavage/linker sequence pairs are well known in the art. For example, Factor Xa can be used for site-specific separation of the GST affinity tag from proteins expressed using pGEX X vectors; PreScission protease can be used for site-specific separation of the GST affinity tag from proteins expressed using pGEX-6P vectors; and Thrombin can be used for site-specific separation of the GST affinity tag from proteins expressed using pGEX T vectors.

The matrix material substrates contemplated herein are generally insoluble materials used to immobilize ligands and other molecules, and are those that used in many chemical syntheses and separations. Such substrates, also called matrices, are used, for example, in affinity chromatography, in the immobilization of biologically active materials, and during chemical syntheses of biomolecules, including proteins, amino acids and other organic molecules and polymers. The preparation of and use of matrices is well known to those of skill in this art; there are many such materials and preparations thereof known. For example, naturally-occurring matrix materials, such as agarose and cellulose, may be isolated from their respective sources, and processed according to known protocols, and synthetic materials may be prepared in accord with known protocols.

The substrate matrices are typically insoluble materials that are solid, porous, deformable, or hard, and have any required structure and geometry, including, but not limited to: beads, pellets, disks, capillaries, hollow fibers, needles, solid fibers, random shapes, thin films and membranes.

Thus, the item may be fabricated from the matrix material or combined with it, such as by coating all or part of the surface or impregnating particles.

Typically, when the matrix is particulate, the particles are at least about 10–2000 µM, but may be smaller or larger, depending upon the selected application. Selection of the matrices will be governed, at least in part, by their physical and chemical properties, such as solubility, functional groups, mechanical stability, surface area swelling propensity, hydrophobic or hydrophilic properties and intended use.

If necessary, the support matrix material can be treated to contain an appropriate reactive moiety. In some cases, the support matrix material already containing the reactive moiety may be obtained commercially. The support matrix material containing the reactive moiety may thereby serve as the matrix support upon which molecules are linked. Materials containing reactive surface moieties such as amino silane linkages, hydroxyl linkages or carboxysilane linkages may be produced by well established surface chemistry techniques involving silanization reactions, or the like. Examples of these materials are those having surface silicon oxide moieties, covalently linked to gamma-aminopropylsilane, and other organic moieties; N-[3-(triethyoxysilyl)propyl]-phthelamic acid; and bis-(2-hydroxyethyl)aminopropyltriethoxysilane. Exemplary of readily available materials containing amino group reactive functionalities, include, but are not limited to, para-aminophenyl-triethyoxysilane. Also derivatized polystyrenes and other such polymers are well known and readily available to those of skill in this art (e.g., the Tentagel® Resins are available with a multitude of functional groups, and are sold by Rapp Polymere, Tubingen, Germany; see, U.S. Pat. Nos. 4,908,405 and 5,292,814; see, also Butz et al., *Peptide Res.*, 7:20–23 (1994); and Kleine et al., *Immunobiol*, 190:53–66 (1994)).

These matrix materials include any material that can act as a support matrix for attachment of the molecules of interest. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene and others (see, Merrifield, *Biochemistry*, 3:1385–1390 (1964)), polyacrylamides, latex gels, polystyrene, dextran, polyacrylamides, rubber, silicon, plastics, nitrocellulose, celluloses, natural sponges. Of particular interest herein, are highly porous glasses (see, e.g., U.S. Pat. No. 4,244,721) and others prepared by mixing a borosilicate, alcohol and water.

Synthetic matrices include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers (see, e.g., Merrifield, *Biochemistry*, 3:1385–1390 (1964); Berg et al., in *Innovation Perspect. Solid Phase Synth. Collect. Pap.*, Int. Symp., 1st, Epton, Roger (Ed), pp. 453–459 (1990); Berg et al., *Pept., Proc. Eur. Pept. Symp.*, 20th, Jung, G. et al. (Eds), pp. 196–198 (1989); Berg et al., *J. Am. Chem. Soc.*, 111:8024–8026 (1989); Kent et al., *Isr. J. Chem.*, 17:243–247 (1979); Kent et al., *J. Org. Chem.*, 43:2845–2852 (1978); Mitchell et al., *Tetrahedron Lett.*, 42:3795–3798 (1976); U.S. Pat. Nos. 4,507,230; 4,006,117; and 5,389,449). Methods for preparation of such matrices are well-known to those of skill in this art.

Synthetic matrices include those made from polymers and co-polymers such as polyvinylalcohols, acrylates and acrylic acids such as poly-ethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethylacrylate, polypropylene-co-methyl acrylate, polyethylene-co-vinyl acetate, polypropylene-co-vinyl acetate, and those containing acid anhydride groups such as polyethylene-co-maleic anhydride, polypropylene-co-maleic anhydride and the like. Liposomes have also been used as solid supports for affinity purifications (Powell et al. *Biotechnol. Bioeng.*, 33:173 (1989)).

For example, U.S. Pat. No. 5,403,750, describes the preparation of polyurethane-based polymers. U.S. Pat. No. 4,241,537 describes a plant growth medium containing a hydrophilic polyurethane gel composition prepared from chain-extended polyols; random copolymerization is preferred with up to 50% propylene oxide units so that the prepolymer will be a liquid at room temperature. U.S. Pat. No. 3,939,123 describes lightly crosslinked polyurethane polymers of isocyanate terminated prepolymers containing poly(ethyleneoxy) glycols with up to 35% of a poly (propyleneoxy) glycol or a poly(butyleneoxy) glycol. In producing these polymers, an organic polyamine is used as a crosslinking agent. Other matrices and preparation thereof are described in U.S. Pat. Nos. 4,177,038, 4,175,183, 4,439, 585, 4,485,227, 4,569,981, 5,092,992, 5,334,640, 5,328,603.

U.S. Pat. No. 4,162,355 describes a polymer suitable for use in affinity chromatography, which is a polymer of an aminimide and a vinyl compound having at least one pendant halo-methyl group. An amine ligand, which affords sites for binding in affinity chromatography is coupled to the polymer by reaction with a portion of the pendant halo-methyl groups and the remainder of the pendant halo-methyl groups are reacted with an amine containing a pendant hydrophilic group. A method of coating a substrate with this polymer is also described. An exemplary aminimide is 1,1-dimethyl-1-(2-hydroxyoctyl)amine methacrylimide and vinyl compound is a chloromethyl styrene.

U.S. Pat. No. 4,171,412 describes specific matrices based on hydrophilic polymeric gels, preferably of a macroporous character, which carry covalently bonded D-amino acids or peptides that contain D-amino acid units. The basic support is prepared by copolymerization of hydroxyalkyl esters or hydroxyalkylamides of acrylic and methacrylic acid with crosslinking acrylate or methacrylate comonomers are modified by the reaction with diamines, aminoacids or dicarboxylic acids and the resulting carboxyterminal or aminoterminal groups are condensed with D-analogs of aminoacids or peptides. The peptide containing D-aminoacids also can be synthesized stepwise on the surface of the carrier. For example, U.S. Pat. No. 4,178,439 describes a cationic ion exchanger and a method for preparation thereof. U.S. Pat. No. 4,180,524 describes chemical syntheses on a silica support.

The fusion protein can be attached to the surface of the matrix material by methods known in the art. Numerous methods have been developed for the immobilization of proteins and other biomolecules onto solid or liquid supports (see, e.g., Mosbach, *Methods in Enzymology*, 44 (1976); Weetall, *Immobilized Enzymes, Antigens, Antibodies, and Peptides*, (1975); Kennedy et al., *Solid Phase Biochemistry*,

*Analytical and Synthetic Aspects*, Scouten, ed., pp. 253–391 (1983); see, generally, Affinity Techniques. Enzyme Purification: *Part B. Methods in Enzymology*, Vol. 34, ed. W. B. Jakoby, M. Wilchek, Acad. Press, N.Y. (1974); and Immobilized Biochemicals and Affinity Chromatography, *Advances in Experimental Medicine and Biology*, vol. 42, ed. R. Dunlap, Plenum Press, N.Y. (1974)).

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art (see, e.g., the PIERCE CATALOG, Immuno Technology Catalog & Handbook, 1992–1993, which describes the preparation of and use of such reagents and provides a commercial source for such reagents; Wong, *Chemistry of Protein Conjugation and Cross Linking*, CRC Press (1993); see also DeWitt et al., *Proc. Natl. Acad. Sci. U.S.A.*, 90:6909 (1993); Zuckermann et al., *J. Am. Chem. Soc.*, 114:10646 (1992); Kurth et al., *J. Am. Chem. Soc.*, 116:2661 (1994); Ellman et al., *Proc. Natl. Acad. Sci. U.S.A.*, 91:4708 (1994); Sucholeiki, *Tetrahedron Lttrs.*, 35:7307 (1994); Su-Sun Wang, *J. Org. Chem.*, 41:3258 (1976); Padwa et al., *J. Org. Chem.*, 41:3550 (1971); and Vedejs et al., *J. Org. Chem.*, 49:575 (1984), which describe photosensitive linkers).

To effect immobilization, a composition containing the protein or other biomolecule is contacted with a support material such as alumina, carbon, an. ion-exchange resin, cellulose, glass or a ceramic. Fluorocarbon polymers have been used as supports to which biomolecules have been attached by adsorption (see, U.S. Pat. No. 3,843,443; Published International PCT Application WO/86 03840).

A large variety of methods are known for attaching biological molecules, including proteins and nucleic acids, molecules to solid supports (see e.g., U.S. Pat. No. 5,451, 683). For example, U.S. Pat. No. 4,681,870 describes a method for introducing free amino or carboxyl groups onto a silica matrix. These groups may subsequently be covalently linked to other groups, such as a protein or other anti-ligand, in the presence of a carbodiimide. Alternatively, a silica matrix may be activated by treatment with a cyanogen halide under alkaline conditions. The anti-ligand is covalently attached to the surface upon addition to the activated surface. Another method involves modification of a polymer surface through the successive application of multiple layers of biotin, avidin and extenders (see e.g., U.S. Pat. No. 4,282,287). Other methods involve photoactivation in which a polypeptide chain is attached to a solid substrate by incorporating a light-sensitive unnatural amino acid group into the polypeptide chain and exposing the product to low-energy ultraviolet light (see e.g., U.S. Pat. No. 4,762, 881). Oligonucleotides have also been attached using a photochemically active reagents, such as a psoralen compound, and a coupling agent, which attaches the photoreagent to the substrate (see e.g., U.S. Pat. Nos. 4,542,102 and 4,562,157). Photoactivation of the photoreagent binds a nucleic acid molecule to the substrate to give a surface-bound probe.

Covalent binding of the protein or other biomolecule or organic molecule or biological particle to chemically activated solid matrix supports such as glass, synthetic polymers, and cross-linked polysaccharides is a more frequently used immobilization technique. The molecule or biological particle may be directly linked to the matrix support or linked via linker, such as a metal (see, e.g., U.S. Pat. No. 4,179,402; and Smith et al., *Methods: A Companion to Methods in Enz.*, 4:73–78 (1992)). An example of this method is the cyanogen bromide activation of polysaccharide supports, such as agarose. The use of perfluorocarbon polymer-based supports for enzyme immobilization and affinity chromatography is described in U.S. Pat. No. 4,885, 250. In this method the biomolecule is first modified by reaction with a perfluoroalkylating agent such as perfluorooctylpropylisocyanate described in U.S. Pat. No. 4,954, 444. Then, the modified protein is adsorbed onto the fluorocarbon support to effect immobilization.

The activation and use of matrices are well known and may be effected by any such known methods (see, e.g., Hermanson et al., *Immobilized Affinity Ligand Techniques*, Academic Press, Inc., San Diego (1992)). For example, the coupling of the amino acids may be accomplished by techniques familiar to those in the art and provided, for example, in Stewart and Young, *Solid Phase Synthesis*, Second Edition, Pierce Chemical Co., Rockford (1984).

Other suitable methods for linking molecules to solid supports are well known to those of skill in this art (see, e.g., U.S. Pat. No. 5,416,193). These include linkers that are suitable for chemically linking molecules, such as proteins, to supports and include, but are not limited to, disulfide bonds, thioether bonds, hindered disulfide bonds, and covalent bonds between free reactive groups, such as amine and thiol groups. These bonds can be produced using heterobifunctional reagents to produce reactive thiol groups on one or both of the moieties and then reacting the thiol groups on one moiety with reactive thiol groups or amine groups to which reactive maleimido groups or thiol groups can be attached on the other.

Other linkers include, acid cleavable linkers, such as bismaleimideothoxy propane, acid labile-transferrin conjugates and adipic acid diihydrazide, that would be cleaved in more acidic intracellular compartments; cross linkers that are cleaved upon exposure to UV or visible light and linkers, such as the various domains, such as $C_H1$, $C_H^2$, and $C_H^3$, from the constant region of human $IgG_1$ (Batra et al., *Molecular Immunol.*, 30:379–386 (1993)). Presently preferred linkages are direct linkages effected by adsorbing the molecule to the surface of the matrix.

Other linkages are photocleavable linkages that can be activated by exposure to light (see, e.g., Goldmacher et al., *Bioconj. Chem.*, 3:104–107 (1992)). The photocleavable linker is selected such that the cleaving wavelength does not damage linked moieties. Photocleavable linkers are linkers that are cleaved upon exposure to light (see, e.g., Hazum et al., *Pept., Proc. Eur. Pept. Symp.*, 16th, Brunfeldt, K (Ed), pp. 105–110 (1981), which describes the use of a nitrobenzyl group as a photocleavable protective group for cysteine; Yen et al., *Makromol. Chem.*, 190:69–82 (1989), which describes water soluble photocleavable copolymers, including hydroxypropylmethacrylamide copolymer, glycine copolymer, fluorescein copolymer and methylrhodamine copolymer; Goldmacher et al., *Bioconj. Chem.*, 3:104–107 (1992), which describes a cross-linker and reagent that undergoes photolytic degradation upon exposure to near UV light (350 nm); and Senter et al., *Photochem. Photobiol*, 42:231–237 (1985), which describes nitrobenzyloxycarbonyl chloride cross linking reagents that produce photocleavable linkages). The selected linker will depend upon the particular application and, if needed, may be empirically selected.

In a preferred embodiment, the recovered fusion protein is attached to the surface through affinity binding between the protein or peptide fragment of the fusion protein and an affinity binding moiety on the surface.

F. SAMPLE COLLECTION

Any sample can be assayed for SAM-dependent methyltransferase activity or screening for modulators of the SAM-dependent methyltransferase using the methods described in the above Sections B–C. In one embodiment, the sample being assayed is a biological sample from a mammal, particularly a human, such as a biological fluid or a biological tissue. Biological fluids, include, but are not limited to, urine, blood, plasma, serum, saliva, semen, stool, sputum, hair and other keratinous samples, cerebral spinal fluid, tears, mucus and amniotic fluid. Biological tissues contemplated include, but are not limited to, aggregates of cells, usually of a particular kind together with their intercellular substance that form one of the structural materials of a human, animal, plant, bacterial, fungal or viral structure, including connective, epithelium, muscle and nerve tissues, organs, tumors, lymph nodes, arteries and individual cell(s). In one specific embodiment, the body fluid to be assayed is urine. In another specific embodiment, the body fluid to be assayed is blood. Preferably, the blood sample is further separated into a plasma or sera fraction.

Serum or plasma can be recovered from the collected blood by any methods known in the art. In one specific embodiment, the serum or plasma is recovered from the collected blood by centrifugation. Preferably, the centrifugation is conducted in the presence of a sealant having a specific gravity greater than that of the serum or plasma and less than that of the blood corpuscles which will form the lower, whereby upon centrifugation, the sealant forms a separator between the upper serum or plasma layer and the lower blood corpuscle layer. The sealants that can be used in the processes include, but are limited to, styrene resin powders (Japanese Patent Publication No. 38841/1973), pellets or plates of a hydrogel of a crosslinked polymer of 2-hydroxyethyl methacrylate or acrylamide (U.S. Pat. No. 3,647,070), beads of polystyrene bearing an antithrombus agent or a wetting agent on the surfaces (U.S. Pat. No. 3,464,890) and a silicone fluid (U.S. Pat. Nos. 3,852,194 and 3,780,935). In a preferred embodiment, the sealant is a polymer of unsubstituted alkyl acrylates and/or unsubstituted alkyl methacrylates, the alkyl moiety having not more than 18 carbon atoms, the polymer material having a specific gravity of about 1.03 to 1.08 and a viscosity of about 5,000 to 1,000,000 cps at a shearing speed of about 1 second$^{-1}$ when measured at about 25° C. (U.S. Pat. No. 4,140,631).

In another specific embodiment, the serum or plasma is recovered from the collected blood by filtration. Preferably, the blood is filtered through a layer of glass fibers with an average diameter of about 0.2 to 5$\mu$ and a density of about 0.1 to 0.5 g./cm$^3$, the total volume of the plasma or serum to be separated being at most about 50% of the absorption volume of the glass fiber layer; and collecting the run-through from the glass fiber layer which is plasma or serum (U.S. Pat. No. 4,477,575). Also preferably, the blood is filtered through a layer of glass fibers having an average diameter 0.5 to 2.5$\mu$, impregnated with a polyacrylic ester derivative and polyethylene glycol (U.S. Pat. No. 5,364,533). More preferably, the polyacrylic ester derivative is poly(butyl acrylate), poly(methyl acrylate) or poly(ethyl acrylate), and (a) poly(butyl acrylate), (b) poly(methyl acrylate) or poly(ethyl acrylate) and (c) polyethylene glycol are used in admixture at a ratio of (10–12):(1–4):(1–4).

In still another specific embodiment, the serum or plasma is recovered from the collected blood by treating the blood with a coagulant containing a lignan skelton having oxygen-containing side chains or rings (U.S. Pat. No. 4,803,153). Preferably, the coagulant contains a lignan skelton having oxygen-containing side chains or rings, e.g., d-sesamin, I-sesamin, paulownin, d-asarinin, I-asarinin, 2$\alpha$-paulownin, 6$\alpha$-paulownin, pinoresinol, d-eudesmin, I-pinoresinol $\beta$-D-glucoside, I-pinoresinol, I-pinoresinol monomethyl ether $\beta$-D-glucoside, epimagnolin, lirioresinol-B, syringaresinol (dl), lirioresinonB-dimethyl ether, phillyrin, magnolin, lirioresinol-A, 2$\alpha$,6a-d-sesamin, d-diaeudesmin, lirioresinol-C dimethyl ether (ddiayangambin) and sesamolin. More preferably, the coagulant is used in an amount ranging from about 0.01 to 50 g per 1 l of the blood.

G. EXAMPLES

Example 1

Preparation of Mutant SAH Hydrolase-encoding Nucleic Acid

Human placental SAH hydrolase gene (SEQ ID No. 3) was subcloned into an expression vector pKK223-3 (Pharmacia Biotech, Piscataway, N.J.) at the EcoR I site. pKK223-3 contains the strong tac promoter upstream from the multiple cloning site and the strong rrnB ribosomal terminator downstream for control of protein expression. The SAH hydrolase gene-containing expression vector was transferred into an *E. coli* strain JM109 (Invitrogen, Carlsbad, Calif.). Site-directed mutagenesis of SAH hydrolase was conducted in two ways: 1) single-strand DNA-based M13 method; and 2) double-strand DNA-based PCR method.

a. Single-strand DNA-based Mutagenesis

Single-strand DNA-based mutagenesis was conducted based on the method described by Taylor et al., *Nucleic Acids Res.*, 13:8765–8785 (1985), which exploits the inability of NciI to cleave a thio-containing DNA strand. Sculptor™ invitro mutagenesis system RPN1526 (Amersham Life science, UK) was used. The pKK223-3 vector containing the wild type gene of SAH hydrolase was prepared using the method of alkaline lysis followed by plasmid purification using Promega's DNA purification kit (Wizard plus Minipreps, Promega, Madison Wis.). The purified plasmid was digested with EcoR I (Stratagene, La Jolla, Calif.) at 37° C. for 2 hours to obtain the EcoR I fragment by agarose gel electrophoresis followed by DNA purification using Promega DNA purification kit. The purified EcoR I fragment was subcloned into M13 mp19 DNA (Pharmacia Biotech, Piscataway, N.J.) by T4 DNA ligase (Pharmacia Biotech Piscataway, N.J.). The ligation was conducted in One-phor-All buffer (10 mM tris-Ac, pH 7.5, 10 mM Mg(Ac)2, 50 mM KAc; Pharmacia LKB Biotechnology AB, Uppsala, Sweden) at 4° C. overnight. The ligation product was transferred into TG1 cells (Stratagene, La Jolla, Calif.) by incubation of 10 $\mu$l of the M13 with 90 $\mu$l of competent TG 1 cells at 0° C. for 30 min. and 42° C. for 75 sec. After being chilled to 0° C. for 2 min, 500 $\mu$l of 2×YT media was added to the cells and incubated for 10 min. at 37° C. Two hundred $\mu$l of growing nontransformed TG1 cells were mixed with the transformed TG1 cells, and to which 2.5 ml of soft agarose LB (42° C.) was added. The cell mixture was immediately poured onto preheated LB agar plates (40° C.), and incubated at 37° C. overnight. Phage clones were picked up for examination of the insertion of SAH hydrolase gene and the orientation through DNA sequencing and restriction enzyme analysis. The selected phage clone was used for preparation of single strand DNA template.

The M13 phage containing the SAH hydrolase gene were incubated with TG1 cells in 3 ml of 2×YT media overnight.

One drop of the overnight culture was mixed with growing TG1 cells (in log phase) in 30 ml of 2×YT media. Cells were incubated for 8 hours with shaking. After centrifugation, the supernatant was collected for single-strand template DNA purification. The purification was conducted according to the manufacture's procedure provided by Amersham Life Science.

b. Design of Primers for Point Mutation

Oligonucleotides (15–30 bases) were synthesized by CruaChem (Sterling, Va.). The sequence of the oligonucleotides were designed to be complementary to the sequence in the region covering both sides of the mutation site. For example, to mutate lys426 to glu426, the oligonucleotides used as primer contained the following sequence: GGCCCCTTCGAGCCGGATCACTACCGC (SEQ ID No. 82) where GAG codes for glu instead of original (wild type) AAG which codes for lys. The selection of mutation sites was based on x-ray structure of the substrate binding site and coenzyme binding site of human SAH hydrolase (Turner et al., *Nature Structural Biology*, 5:369–376 (1998)). Amino acid residues such as Thr157, Asp131, His301, Lys186, Asn191, Glu156, Asp190, Phe362, Phe302, Asn181, His353, Glu59, Ser83, His55, Leu54, Cys79, His301, Arg343, Asp303, Leu344, Asn80, Asn346, Asp107 and entire C-terminal residues can be the mutagenesis targets (see Table 2 for particular mutations generated). The coenzyme binding domain contains residues from Tyr193-Asn346.

The oligonucleotides were dissolved in water to a concentration of 5 ng/μl. The oligonucleotide solution was then phosphorylated at the 5'-end using polynucleotide kinase. The phosphorylation reaction mixture contained the following materials: 2.5 μl of oligonucleotides (5 ng/μl), 3 μl of one-phor-all 10×kinase buffer (Pharmacia Biotech), 21.5 μl of water, 2 μl of 10 mM ATP, and 1 μl of polynucleotide kinase (100,000U/ml) (Pharmacia Biotech). The reaction mixture was incubated at 37° C. for 30 min. followed by heating at 70° C. for 10 min. to inactivate the enzyme.

1.5 μl of T7 DNA polymerase (0.8 units), and 2.5 μl of T4 DNA ligase (92.5 units), and 6 μl of water were added. After 10 min. at room temperature and 30 min. at 37° C., the reaction was stopped by heat inactivation at 70° C. for 15 min. To the reaction mixture was added T5 exonuclease (2000 units) and exonuclease buffer to remove single-strand non-mutant DNA at 37° C. for 30 min. followed by 15 min. of heat inactivation at 70° C. Ncil (5 units) was added to the reaction mixture to nicking the non-mutant strand by incubating Ncil at 37° C. for 90 min. The non-mutant strand was digested by adding 160 units of Exonuclease III and incubating at 37° C. for 30 min. followed by heat inactivation. To repolymerize the gaped DNA, dNTP mix B and 3.5 units of DNA polymerase I and 2.5 units of T4 DNA ligase were added to the reaction mixture, and incubated at 37° C. for 1 h.

The M13 plasmid containing the mutated SAH hydrolase gene was then transferred into competent TG 1 host cells by heat shock method or an electroporation method. Ten μl of the mutant M13 plasmid was added to 90 μl of water and mixed with competent TG1 cells in ice for 40 min. The TG1 cells were shocked by incubation at 42° C. for 45 sec. and immediately at 0° C. for 5 min. The transferred TG1 cells were allowed to return to room temperature, and mixed with 200 μl of growing non-transferred TG1 cells (sever as lawn cells). Three ml of motten Htop agar was added and mixed followed by immediate pouring the cells onto a L plate. The plate was incubated in 37° C. for overnight. Phage plaques formed were picked by sterile tooth pick and swirling in a tube containing 3 ml of 2×YT medium. After overnight culture, cells were collected by centrifugation, and the double-strand M13 plasmid from the cells was purified by using Promega DNA purification kit (Wizard plus Minipreps).

The supernatant from centrifugation was used to purify single-strand M13 DNA. The mutation was confirmed by DNA sequencing of the single-strand M13 DNA using Sequenase Version 2.0 (Unites States Biochemical). The

TABLE 8

Oligonucleotides used for site-directed mutagenesis of human SAH hydrolases

| Mutant | Mutagenic oligonucleotide | Codon Change | SEQ ID |
|--------|--------------------------|--------------|--------|
| K186A | GACTTCGTCACCGCCAGCAAGTTTGGG | AAG→GCC | 83 |
| F302S | AACATTGGACACTCTGACGTGGAGATC | TTT→TCT | 84 |
| H301D | TGTAACATTGGAGACTTTGACGTGGAG | CAC→GAC | 85 |
| H353S | TGTGCCATGGGCTCCCCCAGCTTCGTG | CAC→TCC | 86 |
| R343A | CTGGCCGAGGGTGCGCTGGTCAACCTG | CGG→GCG | 87 |
| D190A | AAGAGCAAGTTTGCCAACCTCTATGGC | GAC→GCC | 88 |
| F82A | AGCTGCAACATCGCCTCCACCCAGGAC | TTC→GCC | 89 |
| N181D | AACCTCTATGGCGACCGGGAGTCCCTC | AAT→GAC | 90 |
| R431A | CCGGATCACTACGCCTACTGAGAATTC | CGC→GCC | 91 |
| K426R | TGTGATGGCTTCCGCCCGGATCACTAC | AAG→CGC | 92 |
| C195S | AACCTCTATGGCTCCCGGGAGTCCCTC | TGC→TCC | 93 |
| Δ432 | GATCACTACCGCTGATGAGAATTCGAG | ATC→TGA | 94 |

The mutagenized codon is underlined, and the nucleotides changed are in boldface type.

The 5'-phosphorylated oligonucleotides DNA was annealed with single-stranded DNA (M13 phage containing wild type human SAH hydrolase gene, 1 μg/μl) in a ratio of oligonucleotide: template of 2:1 in annealing buffer. The annealing reaction was performed by incubating the annealing mixture at 70° C. for 3 min. followed by 30 min. at 37° C. or followed by transferring the micro centrifuge tube to a 55° C. beaker and then allow to cool to room temperature. To the annealing mixture (17 μl), 19 μl of dNTP A (α-S) mix, double-strand M13 DNA containing correct mutation sequence was selected, and digested with EcoR I. The EcoR I fragment containing the mutant SAH hydrolase gene was purified by agarose electrophoresis followed by gene cleaning using Qlaquick Gel Extraction kit (Qiagen, Valencia, Calif.). The purified EcoR I fragment was subcloned into pKK223-3 expression vector using T4 ligase. Two μl of EcoR 1 treated and 5'-dephosphorylated pKK223-3 vector backbone was incubated with 10 μl of the purified mutant insert DNA in a backbone to insert ratio of 2:1. The ligation reaction was carried out in One-phore-All buffer containing 0.01 M ATP at 16C. overnight. The ligated vector containing mutant SAH hydrolase gene was transferred into competent E. Coli JM109 cells by heat shock method. The transformed cells were selected against 100 µl/ml ampicillin. Ampicillin-resistant clones were picked and grown in 10 ml of 2×YT medium containing 35 µl/ml ampicillin for 2 hours at 37° C. and then induced with 1 mM isopropyl-1-thio-β-D-galactopyranoside (IPTG) and grown overnight at 37° C. The cells were harvested by centrifugation, and suspended in 0.8 ml of 50 mM Tri-HCl, pH 7.5, containing 2 mM EDTA. Cells were lysed by rapid freezing and thawing. After centrifugation at 13,500 rpm for 1 hour at 4° C., the supernatant was collected for SDS-PAGE analysis for over-expression of SAH hydrolase mutant protein. A heavy protein band at molecular size of 47,000 Da indicates the overexpression of mutant SAH hydrolase protein.

c. PCR-based Mutagenesis Method

PCR-based mutagenesis was performed using the ExSite PCR-based Site-Directed Mutagenesis Kit (Stratagene, La Jolla, Calif.). The ExSite method uses increased template concentration and <10 PCR cycles. The resulting mixture of template DNA, newly synthesized DNA and hybrid parental/newly synthesized DNA is treated with Dpn I and Pfu DNA polymerase. Dpn I digests the in vivo methylated parental template and hybrid DNA, and Pfu DNA polymerase polishes the ends to create a blunt-ended PCR product. The end-polished PCR product is then intramolecularly ligated together and transformed into E. coli cells. The detailed experimental procedure is described as follows:

To a microcentrifuge tube were added 0.5 pmol of template DNA, 2.5 µl of 10×mutagenesis buffers, 1 µl of 25 mM dNTP mix, 15 pmol of each primer, and ddH$_2$O to a final volume of 24 µl. To the reaction mixture was then added 1 µl of ExSite DNA polymerase blend (5 U/µl). The reaction solution was overlayed with 20 µl of mineral oil and thermal cycle the DNA using 7012 amplification cycles. The cycling parameters are listed in Table 9.

TABLE 9

Mutagenesis Cycling Parameters

| Segment | Cycles | Temperature | Time |
|---------|--------|-------------|------|
| 1 | 1 | 94° C. | 4 min. |
|   |   | 50° C. | 2 min. |
|   |   | 72° C. | 2 min. |
| 2 | 8 | 94° C. | 1 min. |
|   |   | 56° C. | 2 min. |
|   |   | 72° C. | 1 min. |
|   |   | 72° C. | 5 min. |
| 3 |   | 72° C. | 5 min. |

Following amplification, the reaction tube was placed on ice for 2 min. to cool the reaction to <37° C. To the reaction tube were added 1 µl of the Dpn I restriction enzyme (10 U/µl) and 0.5 µl of cloned Pfu DNA polymerase (2.5 U/µl) followed by incubation at 37° C. for 30 min. The reaction was stopped by heating at 72° C. for 30 min. For ligating the product, to the reaction tube were added 100 µl of ddH$_2$O, 10 µl of 10×mutagenesis buffer, and 5 µl of 10 mM rATP. Transfer 10 µl of the above reaction mixture to a new micocentrifuge tube and add 1 µl of T4 DNA ligase (4 U/µl). The ligation was incubated at 37° C. for 1 hour. 2 µl of the ligated DNA was added to 80 µl of Epicurian Coli XL1-Blue supercompetent cells on ice and incubated for 30 min. followed by 45 seconds at 42° C. and 2 min. on ice. The transformed cells were immediately plated on LB-ampicillin agar plates which had been spread with 20 µl of 10% X-gal prepared in DMF and 20 µl of 100 M IPTG in H$_2$O. The plate was incubated overnight at 37° C. The blue colonies were selected as colonies containing the mutagenized plasmid. The selected colonies were further confirmed by DNA sequencing. Protein overexpression and substrate trapping screening were performed as described above.

Double-strand pKK223-3 containing human SAH hydrolase (wild type) was purified from 50 ml of E. coli JM109 culture using Promega DNA purification kit (Wizard plus Minipreps). The purified plasmid was annealed with PCR primers containing the desired mutation sequence.

Deletion and insertion mutations were also performed according to the manufacture's protocol using ExSite PCR-based Site-directed Mutagenesis Kit. Double mutations or combinations of mutation and deletion or insertion were carried out using mutated or deleted DNA as template for secondary mutation or deletion using either M13-based mutagenesis or PCR-based mutagenesis methods.

d. Identification of Substrate Trapping SAH Hydrolase

The cell-free extracts from colonies that inducibly over-expressed mutant SAH hydrolase proteins were chromatographed on a monoQ column (HR5/5) equipped with FPLC system. Proteins were eluted with a linear gradient of NaCl from 0 to 1 M in 10 mM sodium phosphate buffer, pH 7.0 over 35 min. The major protein peak that eluted at the same or close retention time as that of the wild type SAH hydrolase was collected. An aliquot collected mutant SAH hydrolase (1–10 µg) was incubated with [$^3$H]SAH (10 mCi/mmole, 200 µM) and 30 µM of 5,5'-dithiobis(2-nitrobenzoic acid) (DTNB) at room temperature for 5–30 min.

The reaction solution was filtered through a membrane of molecular weight cut-off at 30,000 by centrifugation. The filtrate was measured at 412 nm for Hcy formation (enzyme activity) and the [$^3$H] radioactivity on the membrane was measured by scintillation counting after membrane washing with 1 ml of 50 mM phosphate buffer, pH 7.0.

The mutant hydrolases that show high radioactivity on the membrane and low O.D. at 412 nm of the filtrate relative to the wild type enzyme were selected as candidates for further characterization including determination of Km or Kd and binding energy ($\Delta$G). Mutant SAH hydrolases with Km value lower than 10 µM toward SAH and kcat value lower than 0.1 per second were overexpressed in larger quantity (1–2 L of E. coli culture) and the enzyme proteins were purified to homogenous as judged by single band on SDA-PAGE.

Example 2

Large Scale Overexpression and Purification of Wild Type and Mutant Forms of SAH Hydrolases a. Purification The cell-free extract of IPTG-induced E. Coli JM109 (containing SAH hydrolase gene in pKK223-3 vector) culture was mixed with powder DEAE-cellulose (Sigma, St. Louis, Mo.) equilibrated with 0.1 M sodium phosphate buffer, pH 7.2 containing 1 mM EDTA (buffer A). The cell-free extract and DEAC-cellulose mixture was placed in a funnel and filtrated under vacuum. After washing with 3 volumes of buffer A, the filtrate was precipitated by solid ammonium sulfate (30–60%). The precipitated protein was collected by centrifugation at 13000 rpm, and resuspended in 50 mM sodium phosphate buffer, pH 7.2, containing 1 mM EDTA. The protein was chromatographed through a Sephacryl S-300 size exclusion column (2.5×100 cm) (Pharmacial Biotech, Piscataway, N.J.) followed by a DEAE-Sepharose ion exchange column (2.5×30 cm) eluted by a linear NaCl gradient. The major protein peak from DEAE-Sepharose was examined by SDS-PAGE. In most of the times, this purification procedure gave a single protein band on SDS-PAGE. Sometime, minor bands were observed on SDS-PAGE. In this case, rechromatography on DEAE-Sepharose column was performed to obtain pure protein. SAH hydrolase activity or [$^3$H]SAH binding affinity was also measured to confirm the protein peak.

b. Storage of the Purified SAH Hydrolase

The purified wild type and mutant SAH hydrolases were dialyzed against 5 mM sodium phosphate buffer, pH 7.0 for 6 hours at 4° C. The protein was then frozen in liquid nitrogen and lyophilized under vacuum. The lyophilized protein was stored at −70° C. The protein was stable for at least 2 years. The purified protein can also be stored in liquid containing 20% of glycerol at −20° C. For wild type enzyme, addition of 5 mole excess of adenosine (Ado) to the 20% glycerol solution stabilizes the enzyme activity even better.

c. Assays for Enzyme Activity

The assay of SAH hydrolase activity in the hydrolytic direction was performed as described in Yuan et al., *J. Biol. Chem.*, 271:28008–28016, 1996). The assay measures the hydrolysis of SAH into Ado and Hcy. The reaction product Hcy was derivatized by thiol specific reagent DTNB for colometric determination at 412 nm. The assay for SAH hydrolase in the synthetic direction was measured by the formation of SAH from substrate Ado and Hcy using HPLC (see, Yuan et al., *J. Biol. Chem.*, 268:17030–17037 (1993). One unit of the enzyme activity was defined as the amount of enzyme that can hydrolyze or synthesize 1 μmole of SAH/min/mg.

d. Assay for Binding Affinity (Kd)

For mutant enzyme that completely lacks activity, the binding constant (Kd) values were determined by an equilibrium dialysis technique using [$^3$H] SAH and Spectrum 5-cell Equilibrium Dialyzer) (Spectrum, Houston, Tex.). The membrane disc used had molecular cut-off of 25,000.

Example 3

Preparation of Reagents a. Preparation of fluorophore-labeled Ado and SAH Analogs 1) Method 1

Ado-5'-carboxylic acid (Sigma, St. Louis, Mo.) was derivatized with 9-(hydroxylmethyl)anthracene (HMA) (Fluka, Buchs, Switzerland). To 10 mg of Ado-5'-carboxylic acid dissolved in 100 ml of chloroform (10 min sonication) was added 50 mg 1-hydroxybenzotriazole (HOBT) (Janssen Chimica, Beerse, Belgium). After evaporation to dryness under nitrogen, 300 mg of N-ethyl-N'-(3-dimethylaminopropyl)carbodiimide hydrochloride in 300 ml chloroform and 5 ml of triethylamine were added. The resulting solution was kept at 0° C. for 30 min. To the above reaction mixture was added 200 mg HMA in 100 ml of chloroform. The mixture was allowed to stand at room temperature for 10 min. and then evaporated to dryness under a stream of nitrogen. The residue obtained was dissolved in 10 ml of HPLC mobile phase (methanol-water mixture, 90:10, w/w). One ml of the above solution was injected into a semi-prepative column (Econosphere, C18, 7×300 mm, Alltech, Dearfield, Ill.). The column was eluted with an isocratic method. The flow rate was 2 ml/min. The peaks were monitored at UV260 nm and fluorescence at Ex-365 nm, Em-415 nm. The peaks with UV and fluorescence absorbance were collected as HMA-labeled Ado-5'-ester.

2) Method 2

Ado-5'caroboxylic acid and 4-bromomethyl-7-methoxycoumarin (Br-Mmc) (Sigma, St. Louis, Mo.) were dissolved in ethyl acetate in a molar ratio of 1:3. The reaction volume was 25 ml. After addition of 2 g of finely powdered $K_2CO_3$ the solution was refluxed for 1 hour using a ml-reluxer. After cooling, the reaction solution was injected into a C18 column (Econosphere, C18, 7×300 mm, Alltech, Dearfield, Ill.) for HPLC separation. The elution was monitored by UV (260 nm) and fluorescence (Em 328 nm and Ex390 nm). The elution was performed in a linear gradient of methanol:water from 20 to 100% over 30 min. The flow rate was 2 ml/min.

3) Method 3

This method is depicted in FIG. 3. Adenosyl-L-cysteine (Ado-Cys) and 4-Bromomethyl-7-methoxycoumarin (Br-Mmc) were dissolved in ethyl acetate in a molar ration of 1:3. The final volume was 25 ml (ca, 1 mg Ado-Cys). After addition of 200 mg of finely powdered $K_2CO_3$, the solution was refluxed for 1 hour using a ml-refluxer at 80° C. After cooling, the reaction solution was injected into a C18 column (Econosphere, C18, 7×300 mm, Alltech, Dearfield, Ill.) for separation using HPLC. The fluorescently labeled Ado-Cys was eluted by a linear gradient of methanol; water from 20 to 100% in 30 min. The flow rate was 2 ml/min.

4) Method 4

Ado-Cys was dissolved in carbonate buffer, pH 9.0 in 1 mM concentration. Fluorescein isotiocyanate (FITC) (PcPierce, Rockford, Ill.) was dissolved in DMSO in 5 mM concentration, and diluted to 1 mM with carbonate buffer, pH 9.0. Equal volumes of Ado-Cys and FITC in carbonate buffer were mixed and incubated in room temperature for 1 our. The Ado-Cys-FITC conjugate was then isolated by HPLC using a C18 column (Econsphere, C18, Alltech, Dearfield, Ill.). The elution was monitored at UV 260 nm and fluorescence at Ex484 nm and Em520 nm. The mobile phases were water and methanol in a linear gradient from 0 to 80% of methanol in 35 min.

b. Coating Mutant SAH Hydrolase on Microtiter Well (96 Well Plate)

Mutant SAH hydrolase (F302S) was coated on flat-bottomed 96 well plate (Dynex Technologies, Chantilly, Va.). 200 μl of 20 μg/ml of F302S mutant hydrolase in 50 mM sodium phosphate buffer, pH 7.6. was added to each well. After incubation at 4° C. overnight, the plate was emptied by inversion. After blocking with 0.5% BSA, the plate was then washed three times with 10 mM PBS containing 0.1 NaCl and 0.05% of Tween 20. After inversion and tapping, the plate was stored at 4° C. before use.

c. Preparation of Standard Samples and Chemical Reagents

1) Construction of a Standard Hcy Curve

Human albumin (Fraction V powder, Sigma) was dissolved in PBS in a protein concentration equal to that of human plasma. To 10 ml of the albumin was added 4 ml of 1% tri-n-butylphosphine (TBP). The mixture was incubated at room temperature for 15 min. followed by gel filtration through a size exclusion column (Sephacryl-S100, 2×90 cm). The albumin protein concentration was normalized to human plasma concentration using protein concentrator (Bio-Rad). The protein concentration was determined by Bradford reagent (Bio-Rad). A series of known concentration of L-homocysteine and L-homocysteine were spiked into the TBP-treated human albumin in a final concentrations ranging from 0 to 50 μM. After incubation at 37° C. for 1 hour, the L-homocysteine spiked albumin and L-homocystine albumin were aliquoted in 70 μl/tube as standard samples, and stored at −20° C. before use.

2) Wild Type SAH Hydrolase Solution

The wild type SAH hydrolase (20 mU/50 μl) was dissolved in 50 mM phosphate buffer, Ph 7.2, containing 1 mM EDTA, 0.25 mM Ado and 1 mg/ml of BSA.

3) Tri-n-butylphosphine (TBP) Solution

Tri-n-btylphosphine (Sigma) was dissolved in dimethyl-formamide (DMF) to 1% concentration.

4) Fluorophore-labeled Ado-Cys Solution

Br-Mmc-labeled Ado-Cys or FITC-labeled Ado-Cys was dissolved in 50 mM phosphate buffer, pH 7.2, in a concentration of 0.5 mM.

5) SAH Hydrolase Inhibitor Solution

Neplanocin A (natural product), an inhibitor of SAH hydrolase, and a substrate of adenosine deaminase, was dissolved in 50 mM phosphate buffer, pH 7.2. The inhibitor solution (50 μM) was used in an enzyme to inhibitor ratio of 1:1.5.

6) Multi-enzyme Solution

Adenosine (0.2 U/μl), nucleoside phosphorylase (0.2 U/l) and xanthine oxidase (0.2 U/μl) were dissolved in 50 mM potassium phosphate buffer, pH 7.2. All the enzymes were from Sigma.

7) Washing Solution

The plate washing solution contains of 10 mM PBS, pH 7.2, 0.1 M NaCl, and 0.05% Tween 20.

Example 4

Assays of Hcy Using the Mutant SAH Enzyme a. Plasma Hcy Assay Procedure 1

1) Conversion of Hcy to SAH

To 50 μl of plasma sample in microcentrifuge tube or in uncoated 96-well plate was added 20 μl of 1% TBP and 50 μl of the wild type SAH hydrolase solution. After incubation at 25° C. for 15 min, 20 μl of the enzyme inhibitor solution was added to the reaction mixture, and incubated for 10 min. to inactivate SAH hydrolase.

2) Removal of Remaining Ado and Enzyme Inhibitor

To the solution in Step 1 was added 30 μl of the multi-enzyme solution, and incubated for 15 min at room temperature.

3) Trapping the Formed SAH onto the Mutant SAH Hydrolase

150 μl solution in Step 2 was transferred to a microtiter well pre-coated with mutant SAH hydrolase. After 30 min. incubation at room temperature, the solution was emptied by inversion.

4) Washing

The plate from Step 3 was washed three times with the washing solution followed by inversion and tapping.

5) Binding of Fluorophore-labeled Ado-Cys to the Mutant Enzyme

100 μl of the fluorophore-labeled Ado-Cys or fluorophore-labeled Ado-5' ester was added to the microtiter well in Step 4. After 20 min. incubation at room temperature, the plate was washed three times with the washing solution.

6) Detection of the Mutant SAH Hydrolase-bound Fluorophore-labeled Ado-Cys

To the microtiter well from Step 5, 200 μl of 50 mM phosphate buffer, pH 7.2, was added, and the plate was read for fluorescence using a plate reader (Molecular Devices, fmax). The plasma Hcy concentration was calculated from the standard curve constructed under the same conditions.

b. Alternative Hcy Assay

Alternatively, the Hcy assay can be performed by pre-coating SAH on microtiter well, and using fluorophore-labeled mutant SAH hydrolase for competition binding assay. The details are described as follows:

1) Pre-coating SAH on Microtiter Well

SAH was conjugated to polylysine by activate the carboxylic group of SAH with $PCl_3$ at 50° C. The SAH-polylysine conjugate was purified by HPLC, and dissolved in 0.1 M carbonate buffer, pH 9.6. 300 μl of 100 μg/ml SAH-polylysine solution was added to each well, and incubated at 37° C. for 6 hours. The plate was then washed three times with washing solution containing 10 mM PBS, 0.1 M NaCl and 0.05% Tween 20. After inversion and tapping, the plate was stored at 4° C. before use.

2) Fluorophore-labeled Mutant SAH Hydrolase

Mutant SAH hydrolase (e.g., F302S) was specifically fluorescence labels on Cys421, an non-essential cysteine residue which is located on the surface of the protein that is not involved in substrate binding and catalysis. Cys421 residue is readily accessible by thiol reactive molecules, and can be modified without effect the binding affinity of the enzyme. Thiol specific reactive probes such as 7-diethylamino-3(4'-maleimidylphenyl)-4-methylcoumarin (CPM) can specifically label protein thiols. Mutant SAH hydrolase (F302S) (0.5 mg/ml) in 50 mM phosphate buffer, pH 7.2, was incubated with 2 mM of adenine to protect other thiols in the substrate binding site, followed by addition of CPM to final concentration of 50 μM. The reaction mixture was incubated at room temperature for 30 min. followed by gel filtration on a size exclusion column (Sephacryl S-300, 4.5 mm×60 cm) to remove adenine and excess CPM. The CPM-labeled F302S mutant SAH hydrolase (2 mg/ml) was kept in 50 mM phosphate buffer containing 20% glycerol at −20° C. The comparison of Km (SAH) and Kcat (SAH) for wild type and mutant F302S is shown below in Table 10.

TABLE 10

Comparison of kinetic constants between mutant and wild type SAH hydrolases

| Enzyme | Km (SAH) | Kcat (SAH) |
| --- | --- | --- |
| wild type | 7.9 μM | 3.8 $S^{-1}$ |
| F302S | 1.0 μM | 0.1 $S^{-1}$ | c. Plasma Hcy Assay Procedure 2

1) Conversion of Hcy to SAH

To 50 μl of plasma sample in microcentrifuge tube or in uncoated 96-well plate was added 20 μl of 1% TBP and 50 μl of the enzyme inhibitor solution was added to the reaction mixture, and incubated for 10 min. to inactivate SAH hydrolase.

2) Removal of Remaining Ado and Enzyme Inhibitor

To the solution in Step 1 was added 30 μl of the multi-enzyme solution, and incubated for 15 min. at room temperature.

3) Competition Binding of SAH to the Mutant SAH Hydrolase

One hundred μl of the solution from Step 2 was transferred to a microtiter well pre-coated with polylysine-SAH conjugate to which 150 μl of the fluorophore-labeled mutant SAH hydrolase was added. After incubation at room temperature for 30 min., the plate was inverted and tapped followed by three times of washing with the washing solution.

4) Detection of the Fluorophore-labeled Mutant SAH Hydrolase Bound to the Microtiter Well To the plate from Step 3 was added 200 μl of 10 nM PBS, and the plate was read by a plate reader (Molecular Devices, fmax) at Ex390 nm and Em460 nm. The plasma concentration of Hcy was calculated from the standard curve constructed under the same conditions with the standard samples.

Since modifications will be apparent to those of skill in this art, it is intended that this invention be limited only by the scope of the appended claims.

What is claimed is:

1. A method for assaying for the activity of a S-adenosylmethionine (SAM)-dependent methyltransferase, comprising:
   a) contacting a SAM-dependent methyltransferase with a substrate of the methyltransferase in the presence of SAM, whereby a methyl group is transferred from the methyltransferase to the substrate and the SAM is converted into S-adenosylhomocysteine (SAH);
   b) contacting the resulting SAH with a mutant SAH hydrolase which substantially retains its binding affinity or has enhanced binding affinity for SAH but has attenuated catalytic activity; and
   c) detecting binding between the SAH and the mutant SAH hydrolase to detect or determine the presence or amount of the SAH, whereby the activity of the SAM-dependent methyltransferase is assessed.

2. The method of claim 1, wherein the SAM-dependent methyltransferase is selected from the group consisting of a protein methyltransferase, a nucleic acid methyltransferase, a lipid methyltransferase, a polysaccharide methyltransferase and a small molecule methyltransferase.

3. The method of claim 2, wherein the nucleic acid methyltransferase is a DNA methyltransferase or a RNA methyltransferase.

4. The method of claim 1, wherein the SAM-dependant methyltransferase comprises an amino acid consensus sequence selected from the group consisting of motif I ((V/I/L)(L/V)(D/E)(V/I)G(G/C)G(T/P)G), motif II ((P/G) (Q/T)(F/Y/A)DA(I/V/Y)(F/I)(C/V/L)) and motif III (LL(R/K)PGG(R/I/L)(L/I)(L/F/I/V)(I/L) of combinations thereof.

5. The method of claim 4, wherein the SAM-dependent methyltransferase comprises all the motifs I, II and III in the order of N'-I-II-III-C', the distance between the last amino acid residue of motif I and the first amino acid residue of motif II is from about 36 to about 90 amino acid residues, and the distance between the last amino acid residue of motif II and the first amino acid residue of motif III is from about 12 to about 38 amino acid residues.

6. The method of claim 4, wherein the SAM-dependent methyltransferase comprises the motif I only or comprises the motifs I and III only.

7. The method of claim 1, wherein the method for assaying for the activity of the methyltransferase is a diagnostic assay.

8. The method of claim 1, wherein the method for assaying for the activity of the methyltransferase is an assay for screening for compounds that modulate the activity of the methyltransferase.

9. The method of claim 1, further comprising comparing the activity of the methyltransferase to a control, whereby a change in the activity is detected.

10. The method of claim 1, wherein the mutant SAH hydrolase has attenuated hydrolytic activity but substantially retains its oxidative activity when compared to a wildtype SAH hydrolase from which the mutant SAH hydrolase is derived.

11. The method of claim 1, wherein the SAH is contacted with the mutant SAH hydrolase in the presence of a labeled SAH or a derivative or an analog thereof, whereby the amount of the labeled SAH bound to the mutant SAH hydrolase inversely relates to amount of the SAH produced in step a).

12. The method of claim 11, wherein the labeled SAH derivative or analog is fluorescenctly labeled.

13. The method of claim 1, wherein the mutant SAH hydrolase is a labeled mutant SAH hydrolase.

14. The method of claim 1, wherein the activities of a plurality of SAM-dependant methyltransferases are assayed simultaneously.

15. The method of claim 1, wherein the mutant SAH hydrolase is linked to a solid support.

16. The method of claim 15, wherein a plurality of SAH hydrolases are linked to the support.

17. The method of claim 16, wherein the mutant SAH hydrolases are arranged in an array on the solid support.

* * * * *

UNITED STATES PATENT AND TRADEMARK OFFICE
CERTIFICATE OF CORRECTION

PATENT NO. : 6,610,504 B1  Page 1 of 1
APPLICATION NO. : 09/546013
DATED : August 26, 2003
INVENTOR(S) : Chong-Sheng Yuan It is certified that error appears in the above-identified patent and that said Letters Patent is hereby corrected as shown below:

Title Pg, Item (54) Title, and Col. 1, Line 1, should read:

METHOD OF DETERMINING SAM-DEPENDENT METHYLTRANSFERASE ACTIVITY USING A MUTANT SAH HYDROLASE

Claim 1, column 155, beginning at line 48 should read as follows:

b)   contacting the resulting SAH with a mutant SAH hydrolase comprising the amino acid sequence set forth in SEQ ID No. 3 and comprising one or more mutations selected from the group consisting of Phe 302 to Ser (F302S), Lys 186 to Ala (K186A), His 301 to Asp (H301D), His353 to Ser (H353S), Arg 343 to Ala (R343A), Asp190 to Ala (D190A), Phe 82 to Ala (F82A), Thr157 to Leu (T157L), Cys195 to Asp (C195D), Asn181 to Asp (N181D), deletion of Tyr 432 ($\Delta$432) and a double mutation of Arg431 to Ala (R431A) and Lys 426 to Arg (K426R); and Signed and Sealed this Twenty-first Day of October, 2008

JON W. DUDAS
*Director of the United States Patent and Trademark Office*

SEQUENCE LISTING

<160> NUMBER OF SEQ ID NOS: 94

<210> SEQ ID NO 1
<211> LENGTH: 1135
<212> TYPE: DNA
<213> ORGANISM: Homo sapiens
<220> FEATURE:
<223> OTHER INFORMATION: Human S-Adenysylmethionine-Dependent
      Methyltransferase cDNA
<220> FEATURE:
<221> NAME/KEY: CDS
<222> LOCATION: (30)..(875)
<300> PUBLICATION INFORMATION:
<310> PATENT DOCUMENT NUMBER: 5,876,996
<311> PATENT FILING DATE: 1997-07-25
<312> PUBLICATION DATE: 1999-03-02

<400> SEQUENCE: 1

```
agtcgcaggt gtgctgctga ggcgtgaga atg gcg tcc cgc ggc cgg cgt ccg        53
                                 Met Ala Ser Arg Gly Arg Arg Pro
                                  1               5 gag cat ggc gga ccc cca gag ctg ttt tat gac gag aca gaa gcc cgg       101
Glu His Gly Gly Pro Pro Glu Leu Phe Tyr Asp Glu Thr Glu Ala Arg
     10              15                  20 aaa tac gtt cgc aac tca cgg atg att gat atc cag acc agg atg gct       149
Lys Tyr Val Arg Asn Ser Arg Met Ile Asp Ile Gln Thr Arg Met Ala
 25                  30                  35                  40 ggg cga gca ttg gag ctt ctt tat ctg cca gag aat aag ccc tgt tac       197
Gly Arg Ala Leu Glu Leu Leu Tyr Leu Pro Glu Asn Lys Pro Cys Tyr
                 45                  50                  55 ctg ctg gat att ggc tgt ggc act ggg ctg agt gga agt tat ctg tca       245
Leu Leu Asp Ile Gly Cys Gly Thr Gly Leu Ser Gly Ser Tyr Leu Ser
             60                  65                  70 gat gaa ggg cac tat tgg gtg ggc ctg gat atc agc cct gcc atg ctg       293
Asp Glu Gly His Tyr Trp Val Gly Leu Asp Ile Ser Pro Ala Met Leu
         75                  80                  85 gat gag gct gtg gac cga gag ata gag gga gac ctg ctg ctg ggg gat       341
Asp Glu Ala Val Asp Arg Glu Ile Glu Gly Asp Leu Leu Leu Gly Asp
     90                  95                 100 atg ggc cag ggc atc cca ttc aag cca ggc aca ttt gat ggt tgc atc       389
Met Gly Gln Gly Ile Pro Phe Lys Pro Gly Thr Phe Asp Gly Cys Ile
105                 110                 115                 120 agc att tct gct gtg cag tgg ctc tgt aat gct aac aag aag tct gaa       437
Ser Ile Ser Ala Val Gln Trp Leu Cys Asn Ala Asn Lys Lys Ser Glu
                125                 130                 135 aac cct gcc aag cgc ctg tac tgc ttt ttt gct tct ctt ttt tct gtt       485
Asn Pro Ala Lys Arg Leu Tyr Cys Phe Phe Ala Ser Leu Phe Ser Val
            140                 145                 150 ctc gtc cgg gga tcc cga gct gtc ctg cag ctg tac cct gag aac tca       533
Leu Val Arg Gly Ser Arg Ala Val Leu Gln Leu Tyr Pro Glu Asn Ser
        155                 160                 165 gag cag ttg gag ctg atc aca acc cag gcc aca aag gca ggc ttc tcc       581
Glu Gln Leu Glu Leu Ile Thr Thr Gln Ala Thr Lys Ala Gly Phe Ser
    170                 175                 180 ggt ggc atg gtg gta gac tac cct aac agt gcc aaa gca aag aaa ttc       629
Gly Gly Met Val Val Asp Tyr Pro Asn Ser Ala Lys Ala Lys Lys Phe
185                 190                 195                 200 tac ctc tgc ttg ttt tct ggg cct tcg acc ttt ata cca gag ggg ctg       677
Tyr Leu Cys Leu Phe Ser Gly Pro Ser Thr Phe Ile Pro Glu Gly Leu
                205                 210                 215 agt gaa aat cag gat gaa gtt gaa ccc agg gag tct gtg ttc acc aat       725
```

```
Ser Glu Asn Gln Asp Glu Val Glu Pro Arg Glu Ser Val Phe Thr Asn
            220                 225                 230 gag agg ttc cca tta agg atg tcg agg cgg gga atg gtg agg aag agt      773
Glu Arg Phe Pro Leu Arg Met Ser Arg Arg Gly Met Val Arg Lys Ser
        235                 240                 245 cgg gca tgg gtg ctg gag aag aag gag cgg cac agg cgc cag ggc agg      821
Arg Ala Trp Val Leu Glu Lys Lys Glu Arg His Arg Arg Gln Gly Arg
    250                 255                 260 gaa gtc aga cct gac acc cag tac acc ggc cgc aag cgc aag ccc cgc      869
Glu Val Arg Pro Asp Thr Gln Tyr Thr Gly Arg Lys Arg Lys Pro Arg
265                 270                 275                 280 ttc taa gtcaccacgc ggttctggaa aggcacttgc ctctgcactt ttctatattg       925
Phe ttcagctgac aaagtagtat tttagaaaag ttctaaagtt ataaaaatgt tttctgcagt    985
aaaaaaaaag ttctctgggc cgggcgtggt ggctcacacc tgtaatccca gcaccttggg   1045
aggctgaggt gggaggatca tttgaggcca ggagtttgag acctgcctgg caacataat    1105 gaaacttcct ttccagggag aaaaaaaaaa                                    1135
```

<210> SEQ ID NO 2
<211> LENGTH: 281
<212> TYPE: PRT
<213> ORGANISM: Homo sapiens

<400> SEQUENCE: 2

```
Met Ala Ser Arg Gly Arg Arg Pro Glu His Gly Gly Pro Pro Glu Leu
 1               5                  10                  15

Phe Tyr Asp Glu Thr Glu Ala Arg Lys Tyr Val Arg Asn Ser Arg Met
            20                  25                  30

Ile Asp Ile Gln Thr Arg Met Ala Gly Arg Ala Leu Glu Leu Leu Tyr
        35                  40                  45

Leu Pro Glu Asn Lys Pro Cys Tyr Leu Leu Asp Ile Gly Cys Gly Thr
    50                  55                  60

Gly Leu Ser Gly Ser Tyr Leu Ser Asp Glu Gly His Tyr Trp Val Gly
65                  70                  75                  80

Leu Asp Ile Ser Pro Ala Met Leu Asp Glu Ala Val Asp Arg Glu Ile
                85                  90                  95

Glu Gly Asp Leu Leu Leu Gly Asp Met Gly Gln Gly Ile Pro Phe Lys
            100                 105                 110

Pro Gly Thr Phe Asp Gly Cys Ile Ser Ile Ser Ala Val Gln Trp Leu
        115                 120                 125

Cys Asn Ala Asn Lys Lys Ser Glu Asn Pro Ala Lys Arg Leu Tyr Cys
    130                 135                 140

Phe Phe Ala Ser Leu Phe Ser Val Leu Val Arg Gly Ser Arg Ala Val
145                 150                 155                 160

Leu Gln Leu Tyr Pro Glu Asn Ser Glu Gln Leu Glu Leu Ile Thr Thr
                165                 170                 175

Gln Ala Thr Lys Ala Gly Phe Ser Gly Gly Met Val Val Asp Tyr Pro
            180                 185                 190

Asn Ser Ala Lys Ala Lys Lys Phe Tyr Leu Cys Leu Phe Ser Gly Pro
        195                 200                 205

Ser Thr Phe Ile Pro Glu Gly Leu Ser Glu Asn Gln Asp Glu Val Glu
    210                 215                 220

Pro Arg Glu Ser Val Phe Thr Asn Glu Arg Phe Pro Leu Arg Met Ser
225                 230                 235                 240
```

```
Arg Arg Gly Met Val Arg Lys Ser Arg Ala Trp Val Leu Glu Lys Lys
                245                 250                 255

Glu Arg His Arg Arg Gln Gly Arg Glu Val Arg Pro Asp Thr Gln Tyr
            260                 265                 270

Thr Gly Arg Lys Arg Lys Pro Arg Phe
        275                 280

<210> SEQ ID NO 3
<211> LENGTH: 432
<212> TYPE: PRT
<213> ORGANISM: Homo sapiens
<220> FEATURE:
<223> OTHER INFORMATION: Human S-adenosylhomocysteine hydrolase protein
      sequence
<300> PUBLICATION INFORMATION:
<308> DATABASE ACCESSION NUMBER: M61831/GenBank

<400> SEQUENCE: 3

Met Ser Asp Lys Leu Pro Tyr Lys Val Ala Asp Ile Gly Leu Ala Ala
 1               5                  10                  15

Trp Gly Arg Lys Ala Leu Asp Ile Ala Glu Asn Glu Met Pro Gly Leu
            20                  25                  30

Met Arg Met Arg Glu Arg Tyr Ser Ala Ser Lys Pro Leu Lys Gly Ala
        35                  40                  45

Arg Ile Ala Gly Cys Leu His Met Thr Val Glu Thr Ala Val Leu Ile
    50                  55                  60

Glu Thr Leu Val Thr Leu Gly Ala Glu Val Gln Trp Ser Ser Cys Asn
65                  70                  75                  80

Ile Phe Ser Thr Gln Asn His Ala Ala Ala Ile Ala Lys Ala Gly
                85                  90                  95

Ile Pro Val Tyr Ala Trp Lys Gly Glu Thr Asp Glu Glu Tyr Leu Trp
            100                 105                 110

Cys Ile Glu Gln Thr Leu Tyr Phe Lys Asp Gly Pro Leu Asn Met Ile
        115                 120                 125

Leu Asp Asp Gly Gly Asp Leu Thr Asn Leu Ile His Thr Lys Tyr Pro
    130                 135                 140

Gln Leu Leu Pro Gly Ile Arg Gly Ile Ser Glu Glu Thr Thr Thr Gly
145                 150                 155                 160

Val His Asn Leu Tyr Lys Met Met Ala Asn Gly Ile Leu Lys Val Pro
                165                 170                 175

Ala Ile Asn Val Asn Asp Ser Val Thr Lys Ser Lys Phe Asp Asn Leu
            180                 185                 190

Tyr Gly Cys Arg Glu Ser Leu Ile Asp Gly Ile Lys Arg Ala Thr Asp
        195                 200                 205

Val Met Ile Ala Gly Lys Val Ala Val Ala Gly Tyr Gly Asp Val
    210                 215                 220

Gly Lys Gly Cys Ala Gln Ala Leu Arg Gly Phe Gly Ala Arg Val Ile
225                 230                 235                 240

Ile Thr Glu Ile Asp Pro Ile Asn Ala Leu Gln Ala Ala Met Glu Gly
                245                 250                 255

Tyr Glu Val Thr Thr Met Asp Glu Ala Cys Gln Glu Gly Asn Ile Phe
            260                 265                 270

Val Thr Thr Thr Gly Cys Ile Asp Ile Ile Leu Gly Arg His Phe Glu
        275                 280                 285

Gln Met Lys Asp Asp Ala Ile Val Cys Asn Ile Gly His Phe Asp Val
    290                 295                 300
```

| | | | | | | | | | | | | | | |
|---|---|---|---|---|---|---|---|---|---|---|---|---|---|---|
|Glu|Ile|Asp|Val|Lys|Trp|Leu|Asn|Glu|Asn|Ala|Val|Glu|Lys|Val|Asn|
|305| | | | |310| | | | |315| | | | |320|

Ile Lys Pro Gln Val Asp Arg Tyr Arg Leu Lys Asn Gly Arg Arg Ile
                   325                    330                   335

Ile Leu Leu Ala Glu Gly Arg Leu Val Asn Leu Gly Cys Ala Met Gly
           340                   345                    350

His Pro Ser Phe Val Met Ser Asn Ser Phe Thr Asn Gln Val Met Ala
           355                   360                 365

Gln Ile Glu Leu Trp Thr His Pro Asp Lys Tyr Pro Val Gly Val His
370                    375                    380

Phe Leu Pro Lys Lys Leu Asp Glu Ala Val Ala Glu Ala His Leu Gly
385                    390                    395                    400

Lys Leu Asn Val Lys Leu Thr Lys Leu Thr Glu Lys Gln Ala Gln Tyr
           405                   410                    415

Leu Gly Met Ser Cys Asp Gly Pro Phe Lys Pro Asp His Tyr Arg Tyr
           420                   425                    430

<210> SEQ ID NO 4
<211> LENGTH: 2211
<212> TYPE: DNA
<213> ORGANISM: Homo sapiens
<220> FEATURE:
<223> OTHER INFORMATION: Human S-adenosylhomocysteine hydrolase cDNA
<300> PUBLICATION INFORMATION:
<308> DATABASE ACCESSION NUMBER: M61831/GenBank

<400> SEQUENCE: 4

```
ctgaggccca gcccccttcg cccgtttcca tcacgagtgc cgccagcatg tctgacaaac     60
tgccctacaa agtcgccgac atcggcctgg ctgcctgggg acgcaaggcc ctggacattg    120
ctgagaacga gatgccgggc ctgatgcgta tgcgggagcg gtactcggcc tccaagccac    180
tgaagggcgc ccgcatcgct ggctgcctgc acatgaccgt ggagacggcc gtcctcattg    240
agaccctcgt cacccggggt gctgaggtgc agtggtccag ctgcaacatc ttctccaccc    300
agaaccatgc ggcggctgcc attgccaagg ctggcattcc ggtgtatgcc tggaagggcg    360
aaacggacga ggagtacctg tggtgcattg agcagaccct gtacttcaag gacgggcccc    420
tcaacatgat tctggacgac gggggcgacc tcaccaacct catccacacc aagtacccgc    480
agcttctgcc aggcatccga ggcatctctg aggagaccac gactggggtc acaacctct    540
acaagatgat ggccaatggg atcctcaagg tgcctgccat caatgtcaat gactccgtca    600
ccaagagcaa gtttgacaac ctctatggct gccgggagtc cctcatagat ggcatcaagc    660
gggccacaga tgtgatgatt gccggcaagg tagcggtggt agcaggctat ggtgatgtgg    720
gcaagggctg tgcccaggcc ctgcggggtt cggagcccg cgtcatcatc accgagattg    780
acccatcaa cgcactgcag gctgccatgg agggctatga ggtgaccacc atggatgagg    840
cctgtcagga gggcaacatc tttgtcacca ccacaggctg tattgacatc atccttggcc    900
ggtaggtgcc agatgggggg tcccggggag tgagggagga gggcagagtt gggacagctt    960
tctgtccctg acaatctccc acggtcttgg gctgcctgac aggcactttg agcagatgaa   1020
ggatgatgcc attgtgtgta acattggaca ctttgacgtg gagatcgatg tcaagtggct   1080
caacgagaac gccgtggaga aggtgaacat caagccgcag gtggaccggt atcggttgaa   1140
gaatgggcgc cgcatcatcc tgctggccga gggtcggctg gtcaacctgg gttgtgccat   1200
gggccacccc agcttcgtga tgagtaactc cttcaccaac caggtgatgg cgcagatcga   1260
gctgtggacc catccagaca agtaccccgt tggggttcat ttcctgccca agaagctgga   1320
```

```
tgaggcagtg gctgaagccc acctgggcaa gctgaatgtg aagttgacca agctaactga    1380
gaagcaagcc cagtacctgg gcatgtcctg tgatggcccc ttcaagccgg atcactaccg    1440
ctactgagag ccaggtctgc gtttcaccct ccagctgctg tccttgccca ggccccacct    1500
ctcctcccta agagctaatg caccaactt tgtgattggt ttgtcagtgt cccccatcga     1560
ctctctgggg ctgatcactt agtttttggc ctctgctgca gccgtcatac tgttccaaat    1620
gtggcagcgg aacagagta ccctcttcaa gccccggtca tgatggaggt cccagccaca     1680
gggaaccatg agctcagtgg tcttggaaca gctcactaag tcagtccttc cttagcctgg    1740
aagtcagtag tggagtcaca aagcccatgt gttttgccat ctaggccttc acctggtctg    1800
tggacttata cctgtgtgct tggtttacag gtccagtggt tcttcagccc atgacagatg    1860 agaagggggct atattgaagg gcaaagagga actgttgttt gaattttcct gagagcctgg   1920
cttagtgctg ggccttctct taaacctcat tacaatgagg ttagtacttt tagtccctgt    1980
tttacagggg ttagaataga ctgttaaggg gcaactgaga aagaacagag aagtgacagc    2040 tagggggttga gaggggccag aaaaacatga atgcaggcag atttcgtgaa atctgccacc   2100
actttataac cagatggttc ctttcacaac cctgggtcaa aagagaata atttggccta     2160 taatgttaaa agaaagcagg aaggtgggta aataaaaatc ttggtgcctg g             2211

<210> SEQ ID NO 5
<211> LENGTH: 7
<212> TYPE: PRT
<213> ORGANISM: Saccharomyces cerevisiae
<220> FEATURE:
<223> OTHER INFORMATION: Peptide fragment of fusion protein comprising
      epitope tag: FLAG
<300> PUBLICATION INFORMATION:
<301> AUTHORS: Prickett et al.,
<303> JOURNAL: BioTechniques
<304> VOLUME: 7
<305> ISSUE: 6
<306> PAGES: 580-584
<307> DATE: 1989

<400> SEQUENCE: 5

Asp Tyr Lys Asp Asp Asp Lys
  1               5

<210> SEQ ID NO 6
<211> LENGTH: 9
<212> TYPE: PRT
<213> ORGANISM: Haemophilus influenzae
<220> FEATURE:
<223> OTHER INFORMATION: Peptide fragment of fusion protein comprising
      epitope tag: HA
<300> PUBLICATION INFORMATION:
<301> AUTHORS: Xie et al.,
<303> JOURNAL: Endocrinology
<304> VOLUME: 139
<305> ISSUE: 11
<306> PAGES: 4563-4567
<307> DATE: 1998

<400> SEQUENCE: 6

Tyr Pro Tyr Asp Val Pro Asp Tyr Ala
  1               5

<210> SEQ ID NO 7
<211> LENGTH: 11
<212> TYPE: PRT
<213> ORGANISM: Artificial Sequence
<220> FEATURE:
```

```
<223> OTHER INFORMATION: Peptide fragment of fusion protein comprising
      epitope tag: HA 1
<220> FEATURE:
<223> OTHER INFORMATION: Description of Artificial Sequence: Synthetic
      peptide corresponding to a sequence on an exposed
      loop region the X31 influenza HA1 protein
<300> PUBLICATION INFORMATION:
<301> AUTHORS: Nagelkerken et al.,
<303> JOURNAL: Electrophoresis
<304> VOLUME: 18
<306> PAGES: 2694-2698
<307> DATE: 1997

<400> SEQUENCE: 7

Cys Gln Asp Leu Pro Gly Asn Asp Asn Ser Thr
 1               5                  10

<210> SEQ ID NO 8
<211> LENGTH: 10
<212> TYPE: PRT
<213> ORGANISM: Homo sapiens
<220> FEATURE:
<223> OTHER INFORMATION: Peptide fragment of fusion protein comprising
      epitope tag: c-Myc
<220> FEATURE:
<300> PUBLICATION INFORMATION:
<301> AUTHORS: Xie et al.,
<303> JOURNAL: Endocrinology
<304> VOLUME: 139
<305> ISSUE: 11
<306> PAGES: 4563-4567
<307> DATE: 1998

<400> SEQUENCE: 8

Glu Gln Lys Leu Ile Ser Glu Glu Asp Leu
 1               5                  10

<210> SEQ ID NO 9
<211> LENGTH: 6
<212> TYPE: PRT
<213> ORGANISM: Artificial Sequence
<220> FEATURE:
<223> OTHER INFORMATION: Peptide fragment of fusion protein comprising
      epitope tag: 6-His
<220> FEATURE:
<223> OTHER INFORMATION: Description of Artificial Sequence: Histidine
      repeat epitope tag

<400> SEQUENCE: 9

His His His His His His
 1               5

<210> SEQ ID NO 10
<211> LENGTH: 5
<212> TYPE: PRT
<213> ORGANISM: Bovine papillomavirus
<220> FEATURE:
<223> OTHER INFORMATION: Peptide fragment of fusion protein comprising
      epitope tag: AU1

<400> SEQUENCE: 10

Asp Thr Tyr Arg Ile
 1               5

<210> SEQ ID NO 11
<211> LENGTH: 6
<212> TYPE: PRT
<213> ORGANISM: Homo sapiens
<220> FEATURE:
<223> OTHER INFORMATION: Peptide fragment of fusion protein comprising
      epitope tag: EE
```

```
<300> PUBLICATION INFORMATION:
<301> AUTHORS: Tolbert and Lameh,
<303> JOURNAL: J. Neurochem.
<304> VOLUME: 70
<306> PAGES: 113-119
<307> DATE: 1998

<400> SEQUENCE: 11

Glu Tyr Met Pro Met Glu
 1               5

<210> SEQ ID NO 12
<211> LENGTH: 11
<212> TYPE: PRT
<213> ORGANISM: Artificial Sequence
<220> FEATURE:
<223> OTHER INFORMATION: Peptide sequence of fusion protein comprising
      epitope tag: T7
<220> FEATURE:
<223> OTHER INFORMATION: Description of Artificial Sequence:  T-7 Tag
      Sequence
<300> PUBLICATION INFORMATION:
<301> AUTHORS: Chen and Katz
<303> JOURNAL: BioTechniques
<304> VOLUME: 25
<305> ISSUE: 1
<306> PAGES: 22-24
<307> DATE: 1998
<300> PUBLICATION INFORMATION:
<301> AUTHORS: Tseng and Verma,
<303> JOURNAL: Gene
<304> VOLUME: 169
<306> PAGES: 287-288
<307> DATE: 1996

<400> SEQUENCE: 12

Ala Ser Met Thr Gly Gly Gln Gln Met Gly Arg
 1               5                  10

<210> SEQ ID NO 13
<211> LENGTH: 10
<212> TYPE: PRT
<213> ORGANISM: Mus musculus
<220> FEATURE:
<223> OTHER INFORMATION: Peptide fragment of fusion protein comprising
      epitope tag: 4A6
<300> PUBLICATION INFORMATION:
<301> AUTHORS: Rudiger et al.,
<303> JOURNAL: BioTechniques
<304> VOLUME: 23
<305> ISSUE: 1
<306> PAGES: 96-97
<307> DATE: 1997

<400> SEQUENCE: 13

Ser Phe Pro Gln Phe Lys Pro Gln Glu Ile
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Peptide fragment of fusion protein comprising
      epitope tag: ε
<220> FEATURE:
<223> OTHER INFORMATION: Description of Artificial Sequence: peptide
      derived from last 12 amino acids of protein
      kinase C epsilon gene
<300> PUBLICATION INFORMATION:
<301> AUTHORS: Olah et al.,
<303> JOURNAL: Biochemistry
<304> VOLUME: 221
```

```
<306> PAGES: 94-102
<307> DATE: 1994

<400> SEQUENCE: 14

Lys Gly Phe Ser Tyr Phe Gly Glu Asp Leu Met Pro
 1               5                  10

<210> SEQ ID NO 15
<211> LENGTH: 6
<212> TYPE: PRT
<213> ORGANISM: Bluetongue virus
<220> FEATURE:
<223> OTHER INFORMATION: Peptide fragment of fusion protein comprising
      eptitope tag: B
<300> PUBLICATION INFORMATION:
<301> AUTHORS: Wang et al.
<303> JOURNAL: Gene
<304> VOLUME: 169
<305> ISSUE: 1
<306> PAGES: 53-58
<307> DATE: 1996

<400> SEQUENCE: 15

Gln Tyr Pro Ala Leu Thr
 1               5

<210> SEQ ID NO 16
<211> LENGTH: 11
<212> TYPE: PRT
<213> ORGANISM: Varicella Zoster Virus
<220> FEATURE:
<223> OTHER INFORMATION: Peptide sequence of fusion protein comprising
      eptiope tag: gE
<300> PUBLICATION INFORMATION:
<310> PATENT DOCUMENT NUMBER: 5,710,248
<311> PATENT FILING DATE: 1996-07-29
<312> PUBLICATION DATE: 1998-01-20

<400> SEQUENCE: 16

Gln Arg Gln Tyr Gly Asp Val Phe Lys Gly Asp
 1               5                  10

<210> SEQ ID NO 17
<211> LENGTH: 10
<212> TYPE: PRT
<213> ORGANISM: Saccharomyces cerevisiae
<220> FEATURE:
<223> OTHER INFORMATION: Peptide fragment of fusion protein comprising
      epitope tag: Ty1
<300> PUBLICATION INFORMATION:
<301> AUTHORS: Bastin et al.
<303> JOURNAL: Mol. Biochem. Parasitol.
<304> VOLUME: 77
<306> PAGES: 235-239
<307> DATE: 1996

<400> SEQUENCE: 17

Glu Val His Thr Asn Gln Asp Pro Leu Asp
 1               5                  10

<210> SEQ ID NO 18
<211> LENGTH: 890
<212> TYPE: PRT
<213> ORGANISM: Homo sapiens
<220> FEATURE:
<223> OTHER INFORMATION: T lymphocyte DNA binding protein: NF-At.sub.p
<300> PUBLICATION INFORMATION:
<310> PATENT DOCUMENT NUMBER: 5,656,452
<311> PATENT FILING DATE: 1993-10-29
<312> PUBLICATION DATE: 1997-08-12
```

```
<400> SEQUENCE: 18

Gly Ser Ser Ala Ser Phe Ile Ser Asp Thr Phe Ser Pro Tyr Thr Ser
  1               5                  10                  15

Pro Cys Val Ser Pro Asn Asn Ala Gly Pro Asp Asp Leu Cys Pro Gln
             20                  25                  30

Phe Gln Asn Ile Pro Ala His Tyr Ser Pro Arg Thr Ser Pro Ile Met
         35                  40                  45

Ser Pro Arg Thr Ser Leu Ala Glu Asp Ser Cys Leu Gly Arg His Ser
     50                  55                  60

Pro Val Pro Arg Pro Ala Ser Arg Ser Ser Pro Gly Ala Lys Arg
 65                  70                  75                  80

Arg His Ser Cys Ala Glu Ala Leu Val Ala Pro Leu Pro Ala Ala Ser
                 85                  90                  95

Pro Gln Arg Ser Arg Ser Pro Ser Pro Gln Pro Ser Pro His Val Ala
                100                 105                 110

Pro Gln Asp Asp Ser Ile Pro Ala Gly Tyr Pro Pro Thr Ala Gly Ser
            115                 120                 125

Ala Val Leu Met Asp Ala Leu Asn Thr Leu Ala Thr Asp Ser Pro Cys
130                 135                 140

Gly Ile Pro Ser Lys Ile Trp Lys Thr Ser Pro Asp Pro Thr Pro Val
145                 150                 155                 160

Ser Thr Ala Pro Ser Lys Ala Gly Leu Ala Arg His Ile Tyr Pro Thr
                165                 170                 175

Val Glu Phe Leu Gly Pro Cys Glu Gln Glu Arg Arg Asn Ser Ala
                180                 185                 190

Pro Glu Ser Ile Leu Leu Val Pro Pro Thr Trp Pro Lys Gln Leu Val
            195                 200                 205

Pro Ala Ile Pro Ile Cys Ser Ile Pro Val Thr Ala Ser Leu Pro Pro
210                 215                 220

Leu Glu Trp Pro Leu Ser Asn Gln Ser Gly Ser Tyr Glu Leu Arg Ile
225                 230                 235                 240

Glu Val Gln Pro Lys Pro His His Arg Ala His Tyr Glu Thr Glu Gly
                245                 250                 255

Ser Arg Gly Ala Val Lys Ala Pro Thr Gly Gly His Pro Val Val Gln
                260                 265                 270

Leu His Gly Tyr Met Glu Asn Lys Pro Leu Gly Leu Gln Ile Phe Ile
        275                 280                 285

Gly Thr Ala Asp Glu Arg Ile Leu Lys Pro His Ala Phe Tyr Gln Val
290                 295                 300

His Arg Ile Thr Gly Lys Thr Val Thr Thr Ser Tyr Glu Lys Ile
305                 310                 315                 320

Val Gly Asn Thr Lys Val Leu Glu Ile Pro Leu Glu Pro Lys Asn Asn
                325                 330                 335

Met Arg Ala Thr Ile Asp Cys Ala Gly Ile Leu Lys Leu Arg Asn Ala
                340                 345                 350

Asp Ile Glu Leu Arg Lys Gly Glu Thr Asp Ile Gly Arg Lys Asn Thr
        355                 360                 365

Arg Val Arg Leu Val Phe Arg Val His Val Pro Glu Pro Ser Gly Arg
370                 375                 380

Ile Val Ser Leu Gln Ala Ala Ser Asn Pro Ile Glu Cys Ser Gln Arg
385                 390                 395                 400

Ser Ala His Glu Leu Pro Met Val Glu Arg Gln Asp Met Asp Ser Cys
                405                 410                 415
```

```
Leu Val Tyr Gly Gly Gln Gln Met Ile Leu Thr Gly Gln Asn Phe Thr
            420                 425                 430

Ala Glu Ser Lys Val Val Phe Met Glu Lys Thr Thr Asp Gly Gln Gln
            435                 440                 445

Ile Trp Glu Met Glu Ala Thr Val Asp Lys Asp Lys Ser Gln Pro Asn
            450                 455                 460

Met Leu Phe Val Glu Ile Pro Glu Tyr Arg Asn Lys His Ile Arg Val
465                 470                 475                 480

Pro Val Lys Val Asn Phe Tyr Val Ile Asn Gly Lys Arg Lys Arg Ser
                485                 490                 495

Gln Pro Gln His Phe Thr Tyr His Pro Val Pro Ala Ile Lys Thr Glu
            500                 505                 510

Pro Ser Asp Glu Tyr Glu Pro Ser Leu Ile Cys Ser Pro Ala His Gly
            515                 520                 525

Gly Leu Gly Ser Gln Pro Tyr Tyr Pro Gln His Pro Met Leu Ala Glu
            530                 535                 540

Ser Pro Ser Cys Leu Val Ala Thr Met Ala Pro Cys Gln Gln Phe Arg
545                 550                 555                 560

Ser Gly Leu Ser Ser Pro Asp Ala Arg Tyr Gln Gln Gln Ser Pro Ala
                565                 570                 575

Ala Ala Leu Tyr Gln Arg Ser Lys Ser Leu Ser Pro Gly Leu Leu Gly
            580                 585                 590

Tyr Gln Gln Pro Ser Leu Leu Ala Ala Pro Leu Gly Leu Ala Asp Ala
            595                 600                 605

His Arg Ser Val Leu Val His Ala Gly Ser Gly Gln Gly Gln Gly
            610                 615                 620

Ser Thr Leu Arg His Thr Ser Ser Ala Ser Gln Gln Ala Ser Pro Val
625                 630                 635                 640

Ile His Tyr Ser Pro Thr Asn Gln Gln Leu Arg Gly Gly His Gln
                645                 650                 655

Glu Phe Gln His Ile Met Tyr Cys Glu Asn Phe Gly Pro Ser Ser Ala
            660                 665                 670

Arg Pro Gly Pro Pro Ile Asn Gln Gly Gln Arg Leu Ser Pro Gly
            675                 680                 685

Ala Tyr Pro Thr Val Ile Gln Gln Gln Thr Ala Pro Ser Gln Arg Ala
690                 695                 700

Ala Lys Asn Gly Pro Ser Asp Gln Lys Glu Ala Leu Pro Thr Gly Val
705                 710                 715                 720

Thr Val Lys Gln Glu Gln Asn Leu Asp Gln Thr Tyr Leu Asp Asp Ala
                725                 730                 735

Ala Thr Ser Glu Ser Trp Val Gly Thr Glu Arg Tyr Ile Glu Arg Lys
            740                 745                 750

Phe Trp Lys Lys Thr Leu Val Gln Pro Gly Leu Leu Pro Ser Phe Leu
            755                 760                 765

Leu Leu Gly Ser Leu Ser Ala Gly Pro Arg Ser Gln Thr Pro Ser Glu
            770                 775                 780

Arg Lys Pro Ile Glu Glu Asp Val Pro Leu Ser Cys Ser Gln Ile Ala
785                 790                 795                 800

Trp Cys Cys Gln His Pro Leu Gly Thr Cys Pro Val Leu Pro Gly Pro
                805                 810                 815

Leu Ala Val Glu Trp Trp Glu Gly Gln Leu Gly Arg Gly Leu Glu Pro
            820                 825                 830
```

```
Ile Pro Trp Ala Pro Asp Ser Ala Gly Ser Leu His Glu Val Asp Ser
            835                 840                 845

Val Gly Leu Ala Gly Val Val Gly Met Val Leu Leu Thr Leu Met His
    850                 855                 860

His Phe Ser Met Asp Gln Asn Gln Thr Pro Ser Pro His Trp Gln Arg
865                 870                 875                 880

His Lys Glu Val Ala Ser Pro Gly Trp Ile
                885                 890

<210> SEQ ID NO 19
<211> LENGTH: 29
<212> TYPE: DNA
<213> ORGANISM: Muridae sp.
<220> FEATURE:
<223> OTHER INFORMATION: DNA sequence binding pair:  NF-AT site
<300> PUBLICATION INFORMATION:
<310> PATENT DOCUMENT NUMBER: 5,656,452
<311> PATENT FILING DATE: 1993-10-29
<312> PUBLICATION DATE: 1997-08-12

<400> SEQUENCE: 19
gcccaaagag gaaaatttgt ttcatacag                                           29

<210> SEQ ID NO 20
<211> LENGTH: 160
<212> TYPE: PRT
<213> ORGANISM: Homo sapiens
<220> FEATURE:
<223> OTHER INFORMATION: Human helix-loop-helix zipper protein DNA
      binding sequence: MAX
<300> PUBLICATION INFORMATION:
<310> PATENT DOCUMENT NUMBER: 5,693,487
<311> PATENT FILING DATE: 1994-04-01
<312> PUBLICATION DATE: 1997-12-02

<400> SEQUENCE: 20

Met Ser Asp Asn Asp Asp Ile Glu Val Glu Ser Asp Glu Glu Gln Pro
  1               5                  10                  15

Arg Phe Gln Ser Ala Ala Asp Lys Arg Ala His His Asn Ala Leu Glu
             20                  25                  30

Arg Lys Arg Arg Asp His Ile Lys Asp Ser Phe His Ser Leu Arg Asp
         35                  40                  45

Ser Val Pro Ser Leu Gln Gly Glu Lys Ala Ser Arg Ala Gln Ile Leu
     50                  55                  60

Asp Lys Ala Thr Glu Tyr Ile Gln Tyr Met Arg Arg Lys Asn His Thr
 65                  70                  75                  80

His Gln Gln Asp Ile Asp Asp Leu Lys Arg Gln Asn Ala Leu Leu Glu
                 85                  90                  95

Gln Gln Val Arg Ala Leu Glu Lys Ala Arg Ser Ser Ala Gln Leu Gln
            100                 105                 110

Thr Asn Tyr Pro Ser Ser Asp Asn Ser Leu Tyr Thr Asn Ala Lys Gly
        115                 120                 125

Ser Thr Ile Ser Ala Phe Asp Gly Gly Ser Asp Ser Ser Ser Glu Ser
    130                 135                 140

Glu Pro Glu Glu Pro Gln Ser Arg Lys Lys Leu Arg Met Glu Ala Ser
145                 150                 155                 160

<210> SEQ ID NO 21
<211> LENGTH: 533
<212> TYPE: PRT
<213> ORGANISM: Homo sapiens
<220> FEATURE:
```

```
<223> OTHER INFORMATION: Human Egr Dna binding protein: zinc finger
      domain
<300> PUBLICATION INFORMATION:
<310> PATENT DOCUMENT NUMBER: 5,866,325
<311> PATENT FILING DATE: 1995-06-06
<312> PUBLICATION DATE: 1999-02-02

<400> SEQUENCE: 21
```

| Met | Ala | Ala | Ala | Lys | Ala | Glu | Met | Gln | Leu | Met | Ser | Pro | Leu | Gln | Ile |
|---|---|---|---|---|---|---|---|---|---|---|---|---|---|---|---|
| 1 |  |  |  | 5 |  |  |  |  | 10 |  |  |  |  | 15 |  |

| Ser | Asp | Pro | Phe | Gly | Ser | Phe | Pro | His | Ser | Pro | Thr | Met | Asp | Asn | Tyr |
|---|---|---|---|---|---|---|---|---|---|---|---|---|---|---|---|
|  |  |  | 20 |  |  |  |  | 25 |  |  |  |  | 30 |  |  |

| Pro | Lys | Leu | Glu | Glu | Met | Met | Leu | Leu | Ser | Asn | Gly | Ala | Pro | Gln | Phe |
|---|---|---|---|---|---|---|---|---|---|---|---|---|---|---|---|
|  |  | 35 |  |  |  |  | 40 |  |  |  |  | 45 |  |  |  |

| Leu | Gly | Ala | Ala | Gly | Thr | Pro | Glu | Gly | Ser | Gly | Gly | Asn | Ser | Ser | Ser |
|---|---|---|---|---|---|---|---|---|---|---|---|---|---|---|---|
|  | 50 |  |  |  |  | 55 |  |  |  |  | 60 |  |  |  |  |

| Ser | Thr | Ser | Ser | Gly | Gly | Gly | Gly | Gly | Ser | Asn | Ser | Gly | Ser |
|---|---|---|---|---|---|---|---|---|---|---|---|---|---|
| 65 |  |  |  |  | 70 |  |  |  |  | 75 |  |  | 80 |

| Ser | Ala | Phe | Asn | Pro | Gln | Gly | Glu | Pro | Ser | Glu | Gln | Pro | Tyr | Glu | His |
|---|---|---|---|---|---|---|---|---|---|---|---|---|---|---|---|
|  |  |  |  | 85 |  |  |  |  | 90 |  |  |  |  | 95 |  |

| Leu | Thr | Thr | Glu | Ser | Phe | Ser | Asp | Ile | Ala | Leu | Asn | Asn | Glu | Lys | Ala |
|---|---|---|---|---|---|---|---|---|---|---|---|---|---|---|---|
|  |  |  | 100 |  |  |  |  | 105 |  |  |  |  | 110 |  |  |

| Met | Val | Glu | Thr | Ser | Tyr | Pro | Ser | Gln | Thr | Thr | Arg | Leu | Pro | Pro | Ile |
|---|---|---|---|---|---|---|---|---|---|---|---|---|---|---|---|
|  |  | 115 |  |  |  |  | 120 |  |  |  |  | 125 |  |  |  |

| Thr | Tyr | Thr | Gly | Arg | Phe | Ser | Leu | Glu | Pro | Ala | Pro | Asn | Ser | Gly | Asn |
|---|---|---|---|---|---|---|---|---|---|---|---|---|---|---|---|
|  | 130 |  |  |  |  | 135 |  |  |  |  | 140 |  |  |  |  |

| Thr | Leu | Trp | Pro | Glu | Pro | Leu | Phe | Ser | Leu | Val | Ser | Gly | Leu | Val | Ser |
|---|---|---|---|---|---|---|---|---|---|---|---|---|---|---|---|
| 145 |  |  |  |  | 150 |  |  |  |  | 155 |  |  |  |  | 160 |

| Met | Thr | Asn | Pro | Pro | Thr | Ser | Ser | Ser | Ala | Pro | Ser | Pro | Ala | Ala |
|---|---|---|---|---|---|---|---|---|---|---|---|---|---|---|
|  |  |  | 165 |  |  |  |  | 170 |  |  |  |  | 175 |  |

| Ser | Ser | Ser | Ser | Ser | Ala | Ser | Gln | Ser | Pro | Pro | Leu | Ser | Cys | Ala | Val |
|---|---|---|---|---|---|---|---|---|---|---|---|---|---|---|---|
|  |  |  | 180 |  |  |  |  | 185 |  |  |  |  | 190 |  |  |

| Pro | Ser | Asn | Asp | Ser | Ser | Pro | Ile | Tyr | Ser | Ala | Ala | Pro | Thr | Phe | Pro |
|---|---|---|---|---|---|---|---|---|---|---|---|---|---|---|---|
|  | 195 |  |  |  |  | 200 |  |  |  |  | 205 |  |  |  |  |

| Thr | Pro | Asn | Thr | Asp | Ile | Phe | Pro | Glu | Pro | Gln | Ser | Gln | Ala | Phe | Pro |
|---|---|---|---|---|---|---|---|---|---|---|---|---|---|---|---|
|  | 210 |  |  |  |  | 215 |  |  |  |  | 220 |  |  |  |  |

| Gly | Ser | Ala | Gly | Thr | Ala | Leu | Gln | Tyr | Pro | Pro | Pro | Ala | Tyr | Pro | Ala |
|---|---|---|---|---|---|---|---|---|---|---|---|---|---|---|---|
| 225 |  |  |  |  | 230 |  |  |  |  | 235 |  |  |  |  | 240 |

| Thr | Lys | Gly | Gly | Phe | Gln | Val | Pro | Met | Ile | Pro | Asp | Tyr | Leu | Phe | Pro |
|---|---|---|---|---|---|---|---|---|---|---|---|---|---|---|---|
|  |  |  | 245 |  |  |  |  | 250 |  |  |  |  | 255 |  |  |

| Gln | Gln | Gln | Gly | Asp | Leu | Ser | Leu | Gly | Thr | Pro | Asp | Gln | Lys | Pro | Phe |
|---|---|---|---|---|---|---|---|---|---|---|---|---|---|---|---|
|  |  |  | 260 |  |  |  |  | 265 |  |  |  |  | 270 |  |  |

| Gln | Gly | Leu | Glu | Asn | Arg | Thr | Gln | Gln | Pro | Ser | Leu | Thr | Pro | Leu | Ser |
|---|---|---|---|---|---|---|---|---|---|---|---|---|---|---|---|
|  |  | 275 |  |  |  |  | 280 |  |  |  |  | 285 |  |  |  |

| Thr | Ile | Lys | Ala | Phe | Ala | Thr | Gln | Ser | Gly | Ser | Gln | Asp | Leu | Lys | Ala |
|---|---|---|---|---|---|---|---|---|---|---|---|---|---|---|---|
|  | 290 |  |  |  |  | 295 |  |  |  |  | 300 |  |  |  |  |

| Leu | Asn | Thr | Thr | Tyr | Gln | Ser | Gln | Leu | Ile | Lys | Pro | Ser | Arg | Met | Arg |
|---|---|---|---|---|---|---|---|---|---|---|---|---|---|---|---|
| 305 |  |  |  |  | 310 |  |  |  |  | 315 |  |  |  |  | 320 |

| Lys | Tyr | Pro | Asn | Arg | Pro | Ser | Lys | Thr | Pro | Pro | His | Glu | Arg | Pro | Tyr |
|---|---|---|---|---|---|---|---|---|---|---|---|---|---|---|---|
|  |  |  | 325 |  |  |  |  | 330 |  |  |  |  | 335 |  |  |

| Ala | Cys | Pro | Val | Glu | Ser | Cys | Asp | Arg | Arg | Phe | Ser | Arg | Ser | Asp | Glu |
|---|---|---|---|---|---|---|---|---|---|---|---|---|---|---|---|
|  |  |  | 340 |  |  |  |  | 345 |  |  |  |  | 350 |  |  |

| Leu | Thr | Arg | His | Ile | Arg | Ile | His | Thr | Gly | Gln | Lys | Pro | Phe | Gln | Cys |
|---|---|---|---|---|---|---|---|---|---|---|---|---|---|---|---|
|  |  | 355 |  |  |  |  | 360 |  |  |  |  | 365 |  |  |  |

| Arg | Ile | Cys | Met | Arg | Asn | Phe | Ser | Arg | Ser | Asp | His | Leu | Thr | Thr | His |
|---|---|---|---|---|---|---|---|---|---|---|---|---|---|---|---|

-continued

```
                    370                 375                 380
Ile Arg Thr His Thr Gly Glu Lys Pro Phe Ala Cys Asp Ile Cys Gly
385                 390                 395                 400

Arg Lys Phe Ala Arg Ser Asp Glu Arg Lys Arg His Thr Lys Ile His
                405                 410                 415

Leu Arg Gln Lys Asp Lys Lys Ala Asp Lys Ser Val Val Ala Ser Pro
                420                 425                 430

Ala Ala Ser Ser Leu Ser Ser Tyr Pro Ser Pro Val Ala Thr Ser Tyr
                435                 440                 445

Pro Ser Pro Ala Thr Thr Ser Phe Pro Ser Pro Val Pro Thr Ser Tyr
        450                 455                 460

Ser Ser Pro Gly Ser Ser Thr Tyr Pro Ser Pro Ala His Ser Gly Phe
465                 470                 475                 480

Pro Ser Pro Ser Val Ala Thr Thr Phe Ala Ser Val Pro Pro Ala Phe
                485                 490                 495

Pro Thr Gln Val Ser Ser Phe Pro Ser Ala Gly Val Ser Ser Ser Phe
                500                 505                 510

Ser Thr Ser Thr Gly Leu Ser Asp Met Thr Ala Thr Phe Ser Pro Arg
                515                 520                 525

Thr Ile Glu Ile Cys
        530
```

<210> SEQ ID NO 22
<211> LENGTH: 224
<212> TYPE: PRT
<213> ORGANISM: Homo sapiens
<220> FEATURE:
<223> OTHER INFORMATION: Human S 1-3 DNA binding protein: zinc finger
      domain
<300> PUBLICATION INFORMATION:
<310> PATENT DOCUMENT NUMBER: 5,905,146
<311> PATENT FILING DATE: 1996-03-15
<312> PUBLICATION DATE: 1999-05-18

<400> SEQUENCE: 22

```
Pro Ile Glu Val Cys Arg Ser Lys Leu Ser Lys Tyr Leu Gln Gly Val
 1               5                  10                  15

Val Phe Arg Cys Asp Lys Cys Thr Phe Thr Cys Ser Ser Asp Glu Ser
                20                  25                  30

Leu Gln Gln His Ile Glu Lys His Asn Glu Leu Lys Pro Tyr Lys Cys
            35                  40                  45

Gln Leu Cys Tyr Tyr Glu Thr Lys His Thr Glu Glu Leu Asp Ser His
        50                  55                  60

Leu Arg Asn Glu His Lys Val Ser Arg Asn Phe Glu Leu Val Gly Arg
65                  70                  75                  80

Val Asn Leu Asp Gln Leu Glu Gln Met Lys Glu Lys Met Glu Ser Ser
                85                  90                  95

Ser Ser Asp Asp Glu Asp Lys Glu Glu Glu Met Asn Ser Lys Ala Glu
                100                 105                 110

Asp Arg Glu Leu Met Arg Phe Ser Asp His Gly Ala Ala Leu Asn Thr
            115                 120                 125

Glu Lys Arg Phe Pro Cys Glu Phe Cys Gly Arg Ala Phe Ser Gln Ala
        130                 135                 140

Ser Glu Trp Glu Arg His Val Leu Arg His Gly Met Ala Leu Asn Asp
145                 150                 155                 160

Thr Lys Gln Val Ser Arg Glu Glu Ile His Pro Lys Glu Ile Met Glu
                165                 170                 175
```

```
Asn Ser Val Lys Met Pro Ser Ile Glu Glu Lys Glu Asp Asp Glu Ala
            180                 185                 190

Ile Gly Ile Asp Phe Ser Leu Lys Asn Glu Thr Val Ala Ile Cys Val
        195                 200                 205

Val Thr Ala Asp Lys Ser Leu Leu Glu Asn Ala Glu Ala Lys Lys Glu
        210                 215                 220

<210> SEQ ID NO 23
<211> LENGTH: 272
<212> TYPE: RNA
<213> ORGANISM: Rattus sp.
<220> FEATURE:
<223> OTHER INFORMATION: Untranslated region (UTR) of rat glucose
      transporter mRNA (GLUT1)
<300> PUBLICATION INFORMATION:
<310> PATENT DOCUMENT NUMBER: 5,859,227
<311> PATENT FILING DATE: 1997-02-20
<312> PUBLICATION DATE: 1999-01-12

<400> SEQUENCE: 23
ggggcgggcc aauggcggcg guccuauaaa aaggcagcuc cgcgcgcucu cuuccuaaga      60
acacaagaau cccuugugga gugucgguuu agguugcagg gucuuaagug agucagggcg    120
cggagguccg gcgggagacg cauagucaca gaacguccau ucuccguuuc acagcccgca    180
cagcuugagc cucgagcgca gcgcggccau ggagcccagc agcaagaagg ugacgggccg    240
ccuuauguug gccgugggag gggcagugcu cg                                   272

<210> SEQ ID NO 24
<211> LENGTH: 108
<212> TYPE: RNA
<213> ORGANISM: Homo sapiens
<220> FEATURE:
<223> OTHER INFORMATION: 5' untranslated region (UTR) of human
      3-hydroxy-3-methyl-3-glutaryl CoA reductase
      (HMG,CoA Red)
<300> PUBLICATION INFORMATION:
<310> PATENT DOCUMENT NUMBER: 5,859,227
<311> PATENT FILING DATE: 1997-02-20
<312> PUBLICATION DATE: 1999-01-12

<400> SEQUENCE: 24
uccuuccgcu ccgcgacugc guuaacugga gccaggcuca gcgucggcgc cgggguucgg      60
uggccucuag ugagaucugg aggauccaag gauucguag cuacaaug                  108

<210> SEQ ID NO 25
<211> LENGTH: 107
<212> TYPE: RNA
<213> ORGANISM: Homo sapiens
<220> FEATURE:
<223> OTHER INFORMATION: 5' untranslated region (UTR) of human C4b-
      binding protein- alpha chain
<300> PUBLICATION INFORMATION:
<310> PATENT DOCUMENT NUMBER: 5,859,227
<311> PATENT FILING DATE: 1997-02-20
<312> PUBLICATION DATE: 1999-01-12

<400> SEQUENCE: 25
gcugcuuuau uucugcuguu aaucauucau ugggcccguc aaaaguuucu gcccaucuau      60
uuccaucaac cguccuugac cagccaacca cauggcugaa auucagg                  107

<210> SEQ ID NO 26
<211> LENGTH: 174
<212> TYPE: RNA
<213> ORGANISM: Homo sapiens
```

```
<220> FEATURE:
<223> OTHER INFORMATION: 5' untranslated region (UTR) of human CD45
<300> PUBLICATION INFORMATION:
<310> PATENT DOCUMENT NUMBER: 5,859,227
<311> PATENT FILING DATE: 1997-02-20
<312> PUBLICATION DATE: 1999-01-12

<400> SEQUENCE: 26
cugacaucau caccuagcag uucaugcagc uagcaagugg uuuguucuua ggguaacaga      60
ggaggaaauu guuccucguc ugauaagaca acaguggaga aaggacgcau gcaguuucuu     120
agggacacgg cugacuucca gauaugacca uguauuugug gcuuaaacuc uugg           174

<210> SEQ ID NO 27
<211> LENGTH: 25
<212> TYPE: PRT
<213> ORGANISM: Artificial Sequence
<220> FEATURE:
<223> OTHER INFORMATION: Description of Artificial Sequence: Peptide G25
      representing the putative lipid-binding region (G
      region) of the erythrocyte Ca2+ pump

<400> SEQUENCE: 27

Lys Lys Ala Val Lys Val Pro Lys Lys Glu Lys Ser Val Leu Gln Gly
 1               5                  10                  15

Lys Leu Thr Arg Leu Ala Val Gln Ile
            20                  25

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Primer
      oligonucleotide
<220> FEATURE:
<223> OTHER INFORMATION: The NNS triplet degeneracy is repeated
      depending on the desired length of the complementarity determining
      region (CDR).
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 28
gtgtattatt gtgcgagann stggggccaa gggaccacg                             39

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: synthetic
      peptide representing metal-binding protein surface
      domains from human histadine rich glycoprotien
      (HRG).
<300> PUBLICATION INFORMATION:
<303> JOURNAL: J. Chromatogr.
<304> VOLUME: 604
<305> ISSUE: 1
<306> PAGES: 125-132
<307> DATE: 1992

<400> SEQUENCE: 29

Gly His His Pro His
 1               5

<210> SEQ ID NO 30
<211> LENGTH: 16
```

```
<212> TYPE: PRT
<213> ORGANISM: Artificial Sequence
<220> FEATURE:
<223> OTHER INFORMATION: Description of Artificial Sequence:  Mg (II)
      ion binding protein sequence
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 30

Ser Arg Arg Ser Arg His His Pro Arg Met Trp Asn Gly Leu Asp Val
 1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence:  Mg (II)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 31

Gly Arg Phe Lys Arg Val Arg Asp Arg Trp Val Val Ile Phe Asp Phe
 1               5                  10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence:  Mg (II)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 32

Gly Val Ala Arg Ser Lys Lys Met Arg Gly Leu Trp Arg Leu Asp Val
 1               5                  10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence:  Mg (II)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 33

Gly Leu Ala Val Arg Ser Lys Arg Gly Arg Phe Phe Leu Phe Asp Val
 1               5                  10                  15

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: CU (II) ion
      binding protein sequence.
<300> PUBLICATION INFORMATION:
<310> PATENT DOCUMENT NUMBER: 5,679,548
```

```
<311> PATENT FILING DATE: 1993-06-14
<312> PUBLICATION DATE: 1997-10-21

<400> SEQUENCE: 34

Gly Arg Val His His His Ser Leu Asp Val
 1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequenc : CU (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 35

Ser Trp Lys His His Ala His Trp Asp Val
 1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Cu (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 36

Gly Ser Trp Asp His Arg Gly Cys Asp Gly
 1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Cu (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 37

Gly His His Met Tyr Gly Gly Trp Asp His
 1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Cu (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 38

Gly His Trp Gly Arg His Ser Leu Asp Thr
 1               5                   10
```

```
<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Cu (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 39

Gly His Ile Leu His His Gln Leu Asp Leu
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Cu (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 40

Ser Ser Gln Arg Leu Met Leu Gly Asp Asn
 1               5                  10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Cu (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 41

Ser His His Gly His His Tyr Leu Asn His
 1               5                  10

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Cu (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 42

Gly Lys Leu Met Met Ser Trp Cys Arg Asp Thr Glu Gly Cys Asp His
 1               5                  10                  15

<210> SEQ ID NO 43
<211> LENGTH: 16
<212> TYPE: PRT
<213> ORGANISM: Artificial Sequence
<220> FEATURE:
```

```
<223> OTHER INFORMATION: Description of Artificial Sequence: Cu (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 43

Gly Asp Thr His Arg Gly His Leu Arg His His Leu Pro His Asp Trp
 1               5                  10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Cu (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 44

Gly Trp Gly Leu Trp Met Lys Pro Phe Val Trp Arg Ala Trp Asp Met
 1               5                  10                  15

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Zn (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 45

Gly Arg Val His His His Ser Leu Asp Val
 1               5                  10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence:  Zn (II)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 46

Ser His Thr His Ala Leu Pro Leu Asp Phe
 1               5                  10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Zn (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21
```

```
<400> SEQUENCE: 47

Gly Gln Ser Ser Gly Gly Asp Thr Asp Asp
 1               5                  10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Zn (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 48

Gly Gln Trp Thr Pro Arg Gly Asp Asp Phe
 1               5                  10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Zn (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 49

Gly Arg Cys Cys Pro Ser Ser Cys Asp Glu
 1               5                  10

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Zn (II) ion
      binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 50

Gly Pro Ala Lys His Arg His Arg His Val Gly Gln Met His Asp Ser
 1               5                  10                  15

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Pb (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 51

Gly Asn Leu Arg Arg Lys Thr Ser Asp Ile
 1               5                  10

<210> SEQ ID NO 52
```

```
<211> LENGTH: 10
<212> TYPE: PRT
<213> ORGANISM: Artificial Sequence
<220> FEATURE:
<223> OTHER INFORMATION: Description of Artificial Sequence: Pb (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 52

Gly Glu Ser Asp Ser Lys Arg Glu Asp Gly
  1               5                  10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Pb (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 53

Gly Gly Pro Ser Leu Ala Val Gly Asp Trp
  1               5                  10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Pb (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 54

Gly Pro Leu Gln His Thr Tyr Pro Asp Tyr
  1               5                  10

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Pb (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 55

Gly Trp Lys Val Thr Ala Glu Asp Ser Thr Glu Gly Leu Phe Asp Leu
  1               5                  10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Pb (III)
      ion binding protein sequence.
<300> PUBLICATION INFORMATION:
```

```
<310> PATENT DOCUMENT NUMBER: 5,679,548
<311> PATENT FILING DATE: 1993-06-14
<312> PUBLICATION DATE: 1997-10-21

<400> SEQUENCE: 56

Gly Thr Arg Val Trp Arg Val Cys Gln Trp Asn His Glu Glu Asp Gly
 1               5                  10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Pb (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 57

Gly Glu Trp Trp Cys Ser Phe Ala Met Cys Pro Ala Arg Trp Asp Phe
 1               5                  10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Pb (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 58

Gly Asp Thr Ile Phe Gly Val Thr Met Gly Tyr Tyr Ala Met Asp Val
 1               5                  10                  15

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 59

Gly Gln Val Met Gln Glu Leu Gly Asp Ala
 1               5                  10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 60

Gly Leu Thr Glu Gln Gln Leu Gln Asp Gly
```

-continued

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 61

Gly Tyr Ser Tyr Ser Val Ser Pro Asp Ala
 1               5                  10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 62

Gly Arg Leu Gly Leu Val Met Thr Asp Glu
 1               5                  10

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 63

Ser Thr Trp Pro Gly Arg Gln Arg Leu Gly Gln Ala Leu Ser Asp Ser
 1               5                  10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 64

Gly Tyr Glu Leu Ser Trp Gly Val Asp Gln Gln Glu Trp Trp Asp Ile
 1               5                  10                  15

<210> SEQ ID NO 65
<211> LENGTH: 16
<212> TYPE: PRT
<213> ORGANISM: Artificial Sequence

```
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 65

Gly Pro Val Arg Gly Leu Asp Gln Ser Lys Gly Val Arg Tyr Asp Asn
 1               5                  10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 66

Gly Leu Ser Gln His Ile Val Ser Glu Thr Gln Ser Ser Gly Asp Leu
 1               5                  10                  15

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 67

Gly Leu Glu Ser Leu Lys Val Leu Gly Val Gln Leu Gly Gly Asp Leu
 1               5                  10                  15

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 68

Gly Asn Met Ile Leu Gly Gly Pro Gly Cys Trp Ser Ser Ala Asp Ile
 1               5                  10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21
```

```
<400> SEQUENCE: 69

Gly Cys Trp Asn Val Gln Arg Leu Val Val Tyr His Pro Pro Asp Gly
 1               5                  10                  15

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Ce (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 70

Gly Phe Glu Val Thr Cys Ser Trp Phe Gly His Trp Gly Arg Asp Ser
 1               5                  10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Fe (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 71

Ser Ala Ser Met Arg Ser Ala Ile Gly Leu Trp Arg Thr Met Asp Tyr
 1               5                  10                  15

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Fe (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 72

Gly Asp Arg Glu Ile Phe His Met Gln Trp Pro Leu Arg Val Asp Val
 1               5                  10                  15

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Fe (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 73

Ser Gln Asn Pro Gln Gln Val Cys Gly Val Arg Cys Gly Gln Asp Lys
 1               5                  10                  15
```

```
<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Fe (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 74

Gly Asn Arg Leu Ser Ser Gly His Leu Leu Lys Gln Gly Gln Asp Gly
 1               5                  10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Fe (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 75

Gly Gly Ser Asp Trp Gln Ile Gly Ala Cys Cys Arg Glu Asp Asp Leu
 1               5                  10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Fe (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 76

Gly Met Val Ser Met Met Gly Gln Ser Arg Pro Thr Gln Cys Asp Cys
 1               5                  10                  15

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Fe (III)
      ion binding protein sequence.
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 77

Gly Val Ile Lys Trp Ile Arg Arg Trp Val Arg Thr Ala Arg Asp Val
 1               5                  10                  15

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Fe (III)
      ion binding protein sequence.
```

```
<300> PUBLICATION INFORMATION:
<310> PATENT DOCUMENT NUMBER: 5,679,548
<311> PATENT FILING DATE: 1993-06-14
<312> PUBLICATION DATE: 1997-10-21

<400> SEQUENCE: 78

Gly Trp Phe Trp Arg Leu Leu Pro Thr Pro Arg Ala Pro Ser Asp Val
  1               5                  10                  15

<210> SEQ ID NO 79
<211> LENGTH: 909
<212> TYPE: DNA
<213> ORGANISM: Homo sapiens
<220> FEATURE:
<221> NAME/KEY: CDS
<222> LOCATION: (74)..(541)
<220> FEATURE:
<223> OTHER INFORMATION: Human glutathione S-transferase cDNA
<300> PUBLICATION INFORMATION:
<308> DATABASE ACCESSION NUMBER: J03746/GenBank

<400> SEQUENCE: 79
gaattcaagt cctaaagcct acagttttga atactactga aatgacaagt tattccagac      60
caaaattgaa aaa atg gtt gac ctc acc cag gta atg gat gat gaa gta       109
            Met Val Asp Leu Thr Gln Val Met Asp Asp Glu Val
              1               5                  10 ttc atg gct ttt gca tcc tat gca aca att att ctt tca aaa atg atg     157
Phe Met Ala Phe Ala Ser Tyr Ala Thr Ile Ile Leu Ser Lys Met Met
         15                  20                  25 ctt atg agt act gca act gca ttc tat aga ttg aca aga aag gtt ttt     205
Leu Met Ser Thr Ala Thr Ala Phe Tyr Arg Leu Thr Arg Lys Val Phe
     30                  35                  40 gcc aat cca gaa gac tgt gta gca ttt ggc aaa gga gaa aat gcc aag     253
Ala Asn Pro Glu Asp Cys Val Ala Phe Gly Lys Gly Glu Asn Ala Lys
 45                  50                  55                  60 aag tat ctt cga aca gat gac aga gta gaa cgt gta cgc aga gcc cac     301
Lys Tyr Leu Arg Thr Asp Asp Arg Val Glu Arg Val Arg Arg Ala His
                 65                  70                  75 ctg aat gac ctt gaa aat att att cca ttt ctt gga att ggc ctc ctg     349
Leu Asn Asp Leu Glu Asn Ile Ile Pro Phe Leu Gly Ile Gly Leu Leu
             80                  85                  90 tat tcc ttg agt ggt ccc gac ccc tct aca gcc atc ctg cac ttc aga     397
Tyr Ser Leu Ser Gly Pro Asp Pro Ser Thr Ala Ile Leu His Phe Arg
         95                  100                 105 cta ttt gtc gga gca cgg atc tac cac acc att gca tat ttg aca ccc     445
Leu Phe Val Gly Ala Arg Ile Tyr His Thr Ile Ala Tyr Leu Thr Pro
     110                 115                 120 ctt ccc cag cca aat aga gct ttg agt ttt ttt gtt gga tat gga gtt     493
Leu Pro Gln Pro Asn Arg Ala Leu Ser Phe Phe Val Gly Tyr Gly Val
125                 130                 135                 140 act ctt tcc atg gct tac agg ttg ctg aaa agt aaa ttg tac ctg taa     541
Thr Leu Ser Met Ala Tyr Arg Leu Leu Lys Ser Lys Leu Tyr Leu
                 145                 150                 155 agaaaatcat acaactcaac atccagttgg ctttttaaga attctgtact tccaatttat      601
aatgaatact ttcttagatt ttaggtagga ggggagcaga ggaattatga actggggtaa      661
acccattttg aatattagca ttgccaatat cctgtattct tgttttacat ttggattaga      721
aatttaacat agtaattctt aagtcttttg tctgattttt aaagtacttt cttataaatt      781
tggatcatgt tatgatttgt aacattcaca caacacctca cttttgaatc tataaaagaa      841
ttgcacgtat gagaaaccta tatttcaata ctgctgaaac agacatgaaa taagaatttt      901
``` aaagaatg                                                                909

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Tetrapep-
      tide prior to cleavage site of Factor Xa recognition sequence.
<300> PUBLICATION INFORMATION:
<303> JOURNAL: Nature
<304> VOLUME: 309
<305> ISSUE: 810
<307> DATE: 1984

<400> SEQUENCE: 80

Ile Glu Gly Arg
  1

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: PreScission
      Protease recognition sequence.
<220> FEATURE:
<223> OTHER INFORMATION: PreScission Protease cleaves between Gln and
      Gly.
<300> PUBLICATION INFORMATION:
<303> JOURNAL: J. Biol. Chem.
<304> VOLUME: 265
<306> PAGES: 9062
<307> DATE: 1990

<400> SEQUENCE: 81

Leu Glu Val Leu Phe Gln Gly Pro
  1               5

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant K426D)
<220> FEATURE:
<221> NAME/KEY: mutation
<222> LOCATION: (10)..(12)
<223> OTHER INFORMATION: Codon change from AAG to GAG
<300> PUBLICATION INFORMATION:
<308> DATABASE ACCESSION NUMBER: Z99115/GenBank

<400> SEQUENCE: 82
ggccccttcg agccggatca ctaccgc                                            27

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (Mutant K186A)
<220> FEATURE:
<221> NAME/KEY: mutation
<222> LOCATION: (13)..(15)
<223> OTHER INFORMATION: Codon change from AAG to GCC

<400> SEQUENCE: 83

```
gacttcgtca ccgccagcaa gtttggg                                          27
```

```
<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant F302S)
<220> FEATURE:
<221> NAME/KEY: mutation
<222> LOCATION: (13)..(15)
<223> OTHER INFORMATION: Codon change from TTT-TCT

<400> SEQUENCE: 84
aacattggac actctgacgt ggagatc                                          27
```

```
<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant H301D)
<220> FEATURE:
<221> NAME/KEY: mutation
<222> LOCATION: (13)..(15)
<223> OTHER INFORMATION: Codon change from CAC to GAC

<400> SEQUENCE: 85
tgtaacattg gagactttga cgtggag                                          27
```

```
<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant H353S)
<220> FEATURE:
<221> NAME/KEY: mutation
<222> LOCATION: (13)..(15)
<223> OTHER INFORMATION: Codon change from CAC to TCC

<400> SEQUENCE: 86
tgtgccatgg gctcccccag cttcgtg                                          27
```

```
<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant R343A)
<220> FEATURE:
<221> NAME/KEY: mutation
<222> LOCATION: (13)..(15)
<223> OTHER INFORMATION: Codon change from CGG to GCG

<400> SEQUENCE: 87
ctggccgagg gtgcgctggt caacctg                                          27
```

```
<210> SEQ ID NO 88
<211> LENGTH: 27
<212> TYPE: DNA
<213> ORGANISM: Artificial Sequence
```

```
<220> FEATURE:
<223> OTHER INFORMATION: Description of Artificial Sequence:
      Oligonucleotide used for site-directed mutagenesis
      of Human SAH hydrolase (mutant D190A)
<220> FEATURE:
<221> NAME/KEY: mutation
<222> LOCATION: (13)..(15)
<223> OTHER INFORMATION: Codon change from GAC to GCC

<400> SEQUENCE: 88
aagagcaagt tgccaacct ctatggc                                27

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant F82A)
<220> FEATURE:
<221> NAME/KEY: mutation
<222> LOCATION: (13)..(15)
<223> OTHER INFORMATION: Codon change from TTC to GCC

<400> SEQUENCE: 89
agctgcaaca tcgcctccac ccaggac                               27

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant N181D)
<220> FEATURE:
<221> NAME/KEY: mutation
<222> LOCATION: (13)..(15)
<223> OTHER INFORMATION: Codon change from AAT to GAC

<400> SEQUENCE: 90
aacctctatg gcgaccggga gtccctc                               27

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant R431A)
<220> FEATURE:
<221> NAME/KEY: mutation
<222> LOCATION: (13)..(15)
<223> OTHER INFORMATION: Codon change from CGC to GCC

<400> SEQUENCE: 91
ccggatcact acgcctactg agaattc                               27

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant K426R)
<220> FEATURE:
<221> NAME/KEY: mutation
<222> LOCATION: (13)..(15)
```

-continued

```
<223> OTHER INFORMATION: Codon change from AAG to CGC

<400> SEQUENCE: 92
tgtgatggct tccgcccgga tcactac                                27

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant C195S)
<220> FEATURE:
<221> NAME/KEY: mutation
<222> LOCATION: (13)..(15)
<223> OTHER INFORMATION: Codon change from TGC to TCC

<400> SEQUENCE: 93
aacctctatg gctcccggga gtccctc                                27

<210> SEQ ID NO 94
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant: deletion 432)
<220> FEATURE:
<221> NAME/KEY: mutation
<222> LOCATION: (13)..(15)
<223> OTHER INFORMATION: Codon change from ATC to TGA

<400> SEQUENCE: 94
gatcactacc gctgatgaga attcgag                                27
```